United States Patent
Koike et al.

(10) Patent No.: US 9,440,990 B2
(45) Date of Patent: *Sep. 13, 2016

(54) 1-ARYLCARBONYL-4-OXY-PIPERIDINE COMPOUNDS USEFUL FOR THE TREATMENT OF NEURODEGENERATIVE DISEASES

(71) Applicant: TAKEDA PHARMACEUTICAL COMPANY LIMITED, Osaka (JP)

(72) Inventors: Tatsuki Koike, Kanagawa (JP); Masato Yoshikawa, Kanagawa (JP); Haruhi Ando, Kanagawa (JP); William John Farnaby, Cambridge (GB); Toshiya Nishi, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/847,703

(22) Filed: Sep. 8, 2015

(65) Prior Publication Data

US 2015/0376205 A1 Dec. 31, 2015

Related U.S. Application Data

(62) Division of application No. 14/349,201, filed as application No. PCT/JP2012/076257 on Oct. 3, 2012, now Pat. No. 9,193,709.

(30) Foreign Application Priority Data

Oct. 7, 2011 (JP) ................. 2011/222741

(51) Int. Cl.
| | | |
|---|---|---|
| C07D 498/08 | (2006.01) | |
| C07D 401/14 | (2006.01) | |
| C07D 405/14 | (2006.01) | |
| C07D 413/14 | (2006.01) | |
| C07D 401/10 | (2006.01) | |
| C07D 413/10 | (2006.01) | |
| C07D 417/14 | (2006.01) | |

(52) U.S. Cl.
CPC ........... *C07D 498/08* (2013.01); *C07D 401/10* (2013.01); *C07D 401/14* (2013.01); *C07D 405/14* (2013.01); *C07D 413/10* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | | | |
|---|---|---|---|---|
| 8,648,079 B2* | 2/2014 | Koike | ................. | C07D 401/14 514/252.03 |
| 8,865,717 B2* | 10/2014 | Koike | ................. | C07D 401/14 514/252.03 |
| 8,871,766 B2* | 10/2014 | Koike | ................. | C07D 401/14 514/252.03 |
| 2003/0158238 A1 | 8/2003 | Hale et al. | | |
| 2003/0195192 A1 | 10/2003 | Haviv et al. | | |
| 2003/0195195 A1 | 10/2003 | Haviv et al. | | |
| 2004/0014744 A1 | 1/2004 | Haviv et al. | | |
| 2005/0272789 A1 | 12/2005 | Hale et al. | | |
| 2006/0030557 A1 | 2/2006 | Haviv et al. | | |
| 2006/0167044 A1 | 7/2006 | Arnaiz et al. | | |
| 2007/0123515 A1 | 5/2007 | Nettekoven et al. | | |
| 2007/0142435 A1 | 6/2007 | Gao et al. | | |
| 2008/0021022 A1 | 1/2008 | Bartberger et al. | | |
| 2008/0255045 A1 | 10/2008 | Cujec et al. | | |
| 2010/0075991 A1 | 3/2010 | Pikuleva et al. | | |
| 2010/0168138 A1 | 7/2010 | DeGoey et al. | | |
| 2010/0305111 A1 | 12/2010 | Heimbach et al. | | |
| 2011/0021489 A1 | 1/2011 | Heimbach et al. | | |
| 2011/0172401 A1 | 7/2011 | Cujec et al. | | |
| 2011/0201647 A1 | 8/2011 | Choi-Sledeski et al. | | |
| 2012/0028954 A1 | 2/2012 | Goff et al. | | |
| 2012/0135985 A1 | 5/2012 | Heimbach et al. | | |
| 2012/0220563 A1 | 8/2012 | Heimbach et al. | | |
| 2012/0283445 A1 | 11/2012 | Choi-Sledeski et al. | | |
| 2013/0150564 A1 | 6/2013 | Cujec et al. | | |
| 2013/0252948 A1 | 9/2013 | Heimbach et al. | | |

FOREIGN PATENT DOCUMENTS

| | | |
|---|---|---|
| WO | 02/064558 | 8/2002 |
| WO | 02/088097 | 11/2002 |
| WO | 03/086398 | 10/2003 |

(Continued)

OTHER PUBLICATIONS

Opposition dated Mar. 6, 2015 in corresponding Ecuador Patent Application No. SP2014-13329 with English translation.

(Continued)

*Primary Examiner* — Timothy R Rozof
(74) *Attorney, Agent, or Firm* — Wenderoth, Lind & Ponack, L.L.P.

(57) ABSTRACT

The present invention provides a compound useful as an agent for the prophylaxis or treatment of neurodegenerative disease and the like, or a salt thereof. The present invention relates to a compound represented by the formula (I) wherein each symbol is as defined in the specification, or a salt thereof.

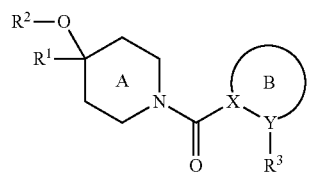

(I)

8 Claims, No Drawings

(56) References Cited

FOREIGN PATENT DOCUMENTS

| WO | 2004/055201 | 7/2004 |
|---|---|---|
| WO | 2006/066948 | 6/2006 |
| WO | 2006/137465 | 12/2006 |
| WO | 2007/062999 | 6/2007 |
| WO | 2007/076354 | 7/2007 |
| WO | 2008/011453 | 1/2008 |
| WO | 2008/121563 | 10/2008 |
| WO | 2008/134547 | 11/2008 |
| WO | 2008/153722 | 12/2008 |
| WO | 2009/117421 | 9/2009 |
| WO | 2010/075376 | 7/2010 |
| WO | 2012/016217 | 2/2012 |
| WO | 2012/080729 | 6/2012 |

OTHER PUBLICATIONS

International Search Report issued Jan. 3, 2013 in International (PCT) Application No. PCT/JP2012/076257.
Chinese Office Action issued Sep. 7, 2015 in corresponding Chinese Application No. 201280049068.8 with English translation of Experimental Report.

* cited by examiner ered as "CH24H") inhibi-
1-ARYLCARBONYL-4-OXY-PIPERIDINE COMPOUNDS USEFUL FOR THE TREATMENT OF NEURODEGENERATIVE DISEASES

TECHNICAL FIELD

The present invention relates to a heterocyclic compound having a cholesterol 24-hydroxylase (in the present specification, sometimes to be abbreviated as "CH24H") inhibitory action, pharmaceutical composition comprising same, and the like.

BACKGROUND OF THE INVENTION

Alzheimer's disease is a progressive neurodegenerative disease characterized by the deposition of amyloid β protein (Aβ), accumulation of phosphorylated tau in a nerve cell (neurofibrillary tangle), and nerve cell death. In recent years, the number of patients with Alzheimer is increasing because of aging, but an effective treatment method has not been developed as yet. The therapeutic drugs for Alzheimer's disease which are currently used in the medical front are mainly acetylcholinesterase (AchE) inhibitors. While AchE inhibitors provide a certain, confirmed level of usefulness, since they aim to supplement depressed acetylcholine, the treatment with AchE inhibitor is merely a symptomatic therapy. Thus, the prompt development of a basic remedy and prophylactic drug has been strongly desired.

It has been clarified that the presence of allele β4 of apolipoprotein E (ApoE) controlling the cholesterol metabolism is a strong risk factor of Alzheimer's disease [non-patent document 1: Science, vol. 261, 921-923, 1993]. After this finding, the correlation between plural gene polymorphisms bearing the expression of protein controlling the cholesterol metabolism and the onset frequency of Alzheimer's disease has been shown, suggesting the correlation between the cholesterol metabolism and Alzheimer's disease [non-patent document 2: Neurobiol. Aging, vol. 24, 421-426, 2003, non-patent document 3: Mol. Psychiatry, vol. 8, 635-638, 2003]. Moreover, it has been reported that Cyp46 (same as "cholesterol 24-hydroxylase (CH24H)"), which is cholesterol oxidase specifically expressed in the brain, is a risk factor of Alzheimer's disease [non-patent document 4: Neurosci. Lett., vol. 328, pages 9-12, 2002]. Furthermore, it has also been reported that Cyp46(CH24H) is expressed in periphery of deposited amyloid in Alzheimer patients [non-patent document 5: J. Biol. Chem., vol. 279, pages 34674-34681, 2004], 24S-hydroxycholesterol (24-HC), which is a metabolite thereof, increases in the brain spinal cord fluid (CSF) of Alzheimer patients [non-patent document 6: Neurosci. Lett., vol. 324, pages 83-85, 2002, non-patent document 7: Neurosci. Lett., vol. 397, pages 83-87, 2006] and that 24-HC induces cell death of SH-SY5Y cell, which is a human neuroblast line [non-patent document 8: Brain Res., vol. 818, pages 171-175, 1999], and rats treated with 24-HC into the cerebral ventricle showed impaired short-term memory, which is commonly observed in Alzheimer's disease, suggesting that hippocampal neurons were damaged by 24-HC [non-patent document 9: Neuroscience, vol. 164, pages 398-403, 2009]. These findings suggest that Cyp46(CH24H) is deeply involved in the pathology of Alzheimer's disease. Therefore, a compound that inhibits the activity of Cyp46 (CH24H) (i.e., Cyp46 (CH24H) inhibitor) suppresses nerve cell death, Aβ increase, intracerebral inflammation and the like observed in Alzheimer's disease, by decreasing intracerebral 24-HC, and is promising as a therapeutic or prophylactic drug showing not only an improvement of symptom but also a suppression of progression. Moreover, it has been reported that AchE inhibitor clinically used as a therapeutic drug for Alzheimer's disease shows an improving effect on memory disorders induced by Aβ in mouse [non-patent document 10: British Journal of Pharmacology, vol. 149, pages 998-1012, 2006], and Cyp46(CH24H) inhibitor showing an improvement effect for memory disorders in Aβ overexpression animal model (APP transgenic mouse, APP/PS1 double transgenic mouse etc.) is promising as a therapeutic drug for Alzheimer's disease.

As a concept of the prestage of Alzheimer's disease, a mild cognitive impairment has been proposed, and about half of those having this disorder is said to progress into the Alzheimer's disease in the future. In recent years, it has been reported that 24-HC increases not only in patients with to Alzheimer's disease but also in CSF of patients with mild cognitive impairment [non-patent document 7: Neurosci. Lett., vol. 397, pages 83-87, 2006]. This finding suggests that Cyp46(CH24H) is involved in the pathology of mild cognitive impairment, and therefore, a Cyp46(CH24H) inhibitor is promising as a new therapeutic drug for Alzheimer's disease or a prophylactic drug for the progression into the Alzheimer's disease.

In recent years, moreover, it has been reported that 24-HC in the blood increases before expression of the symptom in an autoimmune encephalomyelitis model, which is an animal model of multiple sclerosis which is one of the demyelination diseases in the central nervous system [non-patent document 11: J. Neurosci. Res., vol. 85, pages 1499-1505, 2007]. Multiple sclerosis is often developed in younger people of about 30 years old, and scarcely developed in the elderly of 60 years or older. It has also been reported that 24-HC increases in multiple sclerosis patients aging from 21 to 50 [non-patent document 12: Neurosci. Lett., vol. 331, pages 163-166, 2002]. These findings suggest that Cyp46 (CH24H) is involved in the pathology of multiple sclerosis, and therefore, Cyp46(CH24H) inhibitor is promising as a new therapeutic or prophylactic drug for multiple sclerosis.

Traumatic brain injury (also referred to as TBI in the present specification) is a condition exerting an extremely harmful influence on the health of individual, for which no effective cure has been established. In the repair process following tissue damage in TBI, reconstruction of nerve cell membrane and distribution of intracerebral cholesterol activated along with the growth of glial cell are suggested [non-patent document 13: Proc. Natl. Acad. Sci. USA, vol. 102, pages 8333-8338, 2005]. In a rat TBI model, an enhanced expression of Cyp46(CH24H) after trauma has been reported [non-patent document 14: J. Neurotrauma, vol. 25, pages 1087-1098, 2008]. Moreover, it has also been reported that 24-HC injures nerve cells [non-patent document 8: Brain Res., vol. 818, pages 171-175, 1999], and therefore, Cyp46(CH24H) inhibitor is promising as a new therapeutic or prophylactic drug for TBI.

As a pathological significance of 24-HC in neurodegenerative diseases, an inflammatory gene expression-enhancing action in nerve cells has been reported [non-patent document 15: NeuroReport, vol. 16, pages 909-913, 2005]. In addition, it is suggested that an intracerebral inflammation reaction accompanied by activation of glial cell is a pathological change characteristic of neurodegenerative diseases [non-patent document 16: Glia, vol. 50, pages 427-434, 2005]. In recent years, a therapeutic effect by suppression of intracerebral inflammation has also been reported for neurodegenerative diseases such as Huntington's disease, Parkinson's disease and amyotrophic lateral sclerosis and the like [non-patent document 17: Mol. Neurodegeneration, vol. 4, pages 47-59, 2009]. Therefore, suppression of intracerebral inflammation by decreasing 24-HC by the inhibition of Cyp46(CH24H) is promising as a new therapeutic or prophylactic drug for neurodegenerative diseases such as Huntington's disease, Parkinson's disease, cerebral infarction, glaucoma, amyotrophic lateral sclerosis and the like.

Glaucoma is the main cause of blindness, and is considered a serious social problem. However, normal intraocular pressure type field stenosis, which is the major symptom of the disease, has no effective cure. In recent years, it has also been reported that gene polymorphism of Cyp46(CH24H) associated with high blood 24-HC is related to the risk of the onset of glaucoma [non-patent document 18: Invest. Ophthalmol. Vis. Sci., vol. 50, pages 5712-5717, 2009], and Cyp46(CH24H) inhibitor is promising as a therapeutic or prophylactic drug for glaucoma.

Spasm is a disease that occurs in fits along with abnormal electric excitement of intracerebral nerve cells. Spasm is also one of the characteristic clinical findings in Alzheimer's disease [non-patent document 19: Epilepsia, vol. 47, pages 867-872, 2006], and it has been reported that spasm is highly frequently developed in APP/PS1 double transgenic mouse which is one kind of Alzheimer's disease models due to Aβ overexpression [non-patent document 20: J. Neurosci., vol. 29, pages 3453-3462, 2012]. It has been reported that carbamazepine, which is a therapeutic drug for spasm, shows a short term memory improving effect in a Y-maze test using mouse spasm model [non-patent document 21: J. Neurol. Neurosurg. Psychiatry, vol. 48, pages 459-468, 1985]. Thus, in animal model with spasm symptoms, Cyp46 (CH24H) inhibitor showing a short term memory improving effect is promising as a therapeutic or prophylactic drug for spasm.

Since schizophrenia shows a variety of psychological symptoms such as hallucination, delusion, excitation, manic-depressive state and the like, therapeutic drugs therefor have been developed from various angles. In recent years, it has been pointed out that changes in the cholesterol metabolism are involved in the abnormality of neural activity seen in schizophrenia [non-patent document 22: J. Psychiatry Neurosci., vol. 36, pages 47-55, 2011]. Since cytotoxic factors such as oxidative stress also contribute to the pathology of schizophrenia, nerve cell toxicity due to 24-HC may aggravate the symptoms [non-patent document 23: Psychoneuroendocrinology, vol. 28, pages 83-96, 2003]. Therefore, Cyp46(CH24H) inhibitor that inhibits metabolism of cholesterol into 24-HC in the brain is promising as a new therapeutic or prophylactic drug for schizophrenia.

Examples of the compound having a structure similar to the present compound include the following compounds.

Patent document 1 discloses the following compound:

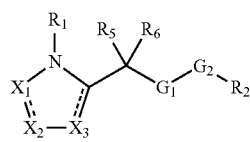

wherein
$X_1$, $X_2$ and $X_3$ are independently N, O, S, C or the like;
$G_1$ is $CR^aR^b$, $NR^7$, or optionally substituted nitrogen-containing heterocycloalkyl;
$G_2$ is a single bond, optionally substituted alkyl or the like;
$R^1$ is aryl, nitrogen-containing heteroaryl or the like;
$R^2$ is optionally substituted alkyl, optionally substituted aryl, optionally substituted heteroaryl or the like;
$R^3$ and $R^4$ are independently H, halogen, optionally substituted alkyl or the like;
$R^5$, $R^6$, $R^7$ and $R^8$ are independently H, halogen, optionally substituted alkyl or the like;
$R^5$ and $R^6$ in combination optionally form oxo; and
$R^a$ and $R^b$ are independently H, halogen, optionally substituted alkyl or the like,
as an agent for the treatment of inflammation disease, Alzheimer's disease and the like.

Patent document 2 discloses the following compound:

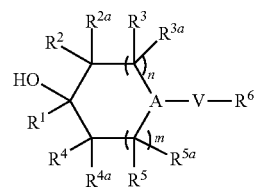

wherein
V is carbonyl or the like;
A is N or C(H);
$R^1$ is H, optionally substituted alkyl, optionally substituted alkenyl, optionally substituted alkynyl or the like;
$R^2$, $R^{2a}$, $R^3$, $R^{3a}$, $R^4$, $R^{4a}$, $R^5$ and $R^{5a}$ are independently H, halogen, optionally substituted alkyl or the like;
$R^6$ is $-R^8-OR^{10}$, optionally substituted alkyl, optionally substituted cycloalkyl, optionally substituted aryl, optionally substituted heterocycloalkyl, optionally substituted heteroaryl or the like;
$R^8$ is a single bond, alkynylene or alkenylene; and
$R^9$ and $R^{10}$ are independently H, halogen, optionally substituted alkyl or the like,
as an agent for the treatment of autoimmune diseases, Alzheimer's disease, age-related dementia and the like.

Patent document 3 discloses the following compound:

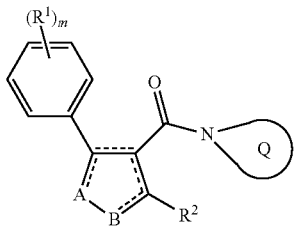

wherein
A-B is N—O, O—N or N(H)—N;
$R^1$ is H, $C_{1-8}$ alkyl, $C_{1-8}$ alkoxy, hydroxy, halogen or the like;
$R^2$ is H, aryl, heteroaryl, $C_{1-6}$ alkyl or the like;
Q is a nitrogen-containing ring (the following formula (IIb) etc.)

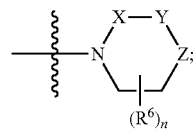

IIb $R^6$ is H, hydroxy, aryl or the like;
X, Y and Z are independently O, $NR^7$ or $CR^7{}_2$;
$R^7$ is, H, $C_{1-8}$ alkyl, $C_{2-8}$ alkenyl, $C_{1-4}$ alkoxy, heteroaryl-$C_{1-6}$ alkyl, aryl-$C_{1-6}$ alkyl or the like; and
n is 0-3,
as an agent for the treatment of diseases associated with immune disease, dementia, hypertension, diabetes and the like (e.g., Alzheimer's disease etc.)

Patent document 4 discloses the following compound:

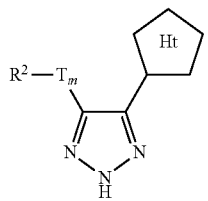

wherein
Ht is a heterocyclic group (pyrrol-3-yl, [1,2,4]triazol-3-yl, [1,2,3]triazol-4-yl or tetrazol-5-yl, the pyrrol-3-yl has $R^3$ and Qn-$R^4$, and the [1,2,4]triazol-3-yl or [1,2,3]triazol-4-yl has $R^3$ or Qn-$R^4$);
T and Q are independently —C(O)— or the like;
m and n are independently 0-1;
$R^2$ is R or the like;
$R^3$ is $R^7$, halogen, cyano or the like;
R is a $C_{1-6}$ hydrocarbon group, $C_{6-10}$ aryl, $C_{6-10}$ heteroaryl, $C_{3-10}$ heterocycloalkyl or the like; and
$R^7$ is H, an optionally substituted $C_{1-6}$ hydrocarbon group or the like,
as an agent for the treatment of autoimmune diseases, Alzheimer's disease and the like.

DOCUMENT LIST

Patent Document

Patent Document 1: WO 2009/117421
Patent Document 2: WO 2008/134547
Patent Document 3: WO 2008/011453
Patent Document 4: WO 02/088097

Non-Patent Document

Non-Patent Document 1: Science, vol. 261, 921-923, 1993
Non-Patent Document 2: Neurobiol. Aging, vol. 24, 421-426, 2003
Non-Patent Document 3: Mol. Psychiatry, vol. 8, 635-638, 2003
Non-Patent Document 4: Neurosci. Lett., vol. 328, pages 9-12, 2002
Non-Patent Document 5: J. Biol. Chem., vol. 279, pages 34674-34681, 2004
Non-Patent Document 6: Neurosci. Lett., vol. 324, pages 83-85, 2002
Non-Patent Document 7: Neurosci. Lett., vol. 397, pages 83-87, 2006
Non-Patent Document 8: Brain Res., vol. 818, pages 171-175, 1999
Non-Patent Document 9: Neuroscience, vol. 164, pages 398-403, 2009
Non-Patent Document 10: British Journal of Pharmacology, vol. 149, pages 998-1012, 2006
Non-Patent Document 11: J. Neurosci. Res., vol. 85, pages 1499-1505, 2007
Non-Patent Document 12: Neurosci. Lett., vol. 331, pages 163-166, 2002
Non-Patent Document 13: Proc. Natl. Acad. Sci. USA, vol. 102, pages 8333-8338, 2005
Non-Patent Document 14: J. Neurotrauma, vol. 25, pages 1087-1098, 2008
Non-Patent Document 15: NeuroReport, vol. 16, pages 909-913, 2005
Non-Patent Document 16: Glia, vol. 50, pages 427-434, 2005
Non-Patent Document 17: Mol. Neurodegeneration, vol. 4, pages 47-59, 2009
Non-Patent Document 18: Invest. Opthalmol. Vis. Sci., vol. 50, pages 5712-5717, 2009
Non-Patent Document 19: Epilepsia, vol. 47, pages 867-872, 2006
Non-Patent Document 20: J. Neurosci., vol. 29, pages 3453-3462, 2012
Non-Patent Document 21: J. Neurol. Neurosurg. Psychiatry, vol. 48, pages 459-468, 1985
Non-Patent Document 22: J. Psychiatry Neurosci., vol. 36, pages 47-55, 2011
Non-Patent Document 23: Psychoneuroendocrinology, vol. 28, pages 83-96, 2003

SUMMARY OF THE INVENTION

Problems to be Solved by the Invention

An object of the present invention is to provide a compound having a superior CH24H inhibitory action, which is useful as an agent for the prophylaxis or treatment of neurodegenerative disease (e.g., Alzheimer's disease, mild cognitive impairment, Huntington's disease, Parkinson's disease, amyotrophic lateral sclerosis, traumatic brain injury, cerebral infarction, glaucoma, multiple sclerosis and the like), epilepsy, schizophrenia and the like.

Means of Solving the Problems

The present inventors have conducted intensive studies in an attempt to solve the above-mentioned problem and found that a compound represented by the following formula (I) has a superior CH24H inhibitory action, which resulted in the completion of the present invention.

Accordingly, the present invention provides the following. [1] A compound represented by the formula (I):

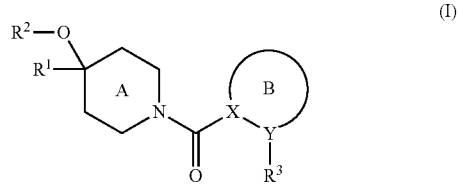

wherein
$R^1$ is an optionally substituted $C_{1-6}$ alkyl group;
$R^2$ is a hydrogen atom or an optionally substituted $C_{1-6}$ alkyl group;
$R^3$ is an optionally substituted 5- or 6-membered aromatic heterocyclic group;

ring A is a further optionally substituted piperidine ring (the piperidine ring is optionally bridged); and
ring B is a further optionally substituted 5- or 6-membered aromatic ring (X and Y are independently a carbon atom or a nitrogen atom),
or a salt thereof.

[2] The compound or salt of the above-mentioned [1], wherein $R^3$ is an optionally substituted 5- or 6-membered nitrogen-containing aromatic heterocyclic group.

[3] The compound or salt of the above-mentioned [1], wherein $R^3$ is a 5- or 6-membered nitrogen-containing aromatic heterocyclic group optionally substituted by 1 to 3 halogen atoms.

[4] The compound or salt of the above-mentioned [1], wherein $R^3$ is a group represented by

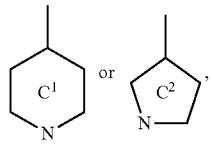

wherein
ring $C^1$ is an optionally substituted 6-membered nitrogen-containing aromatic heterocycle containing at least one nitrogen atom; and
ring $C^2$ is an optionally substituted 5-membered nitrogen-containing aromatic heterocycle containing at least one nitrogen atom,
each of which is optionally substituted by 1 to 3 halogen atoms.

[5] The compound or salt of the above-mentioned [1], wherein ring B is benzene, thiazole, isoxazole, pyrazole, pyridine or pyrazine (X and Y are independently a carbon atom or a nitrogen atom), each of which is, in addition to $R^3$ and —C(=O)— ring A, optionally substituted by 1 to 3 substituents selected from
(1) a halogen atom,
(2) a $C_{1-6}$ alkyl group optionally substituted by 1 to 3 halogen atoms,
(3) a $C_{1-6}$ alkoxy group, and
(4) a $C_{1-6}$ alkylenedioxy group.

[6] The compound or salt of the above-mentioned [1], wherein ring B is

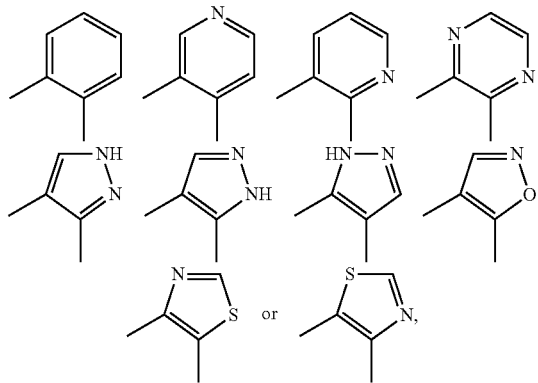

each of which is, in addition to $R^3$ and —C(=O)-ring A, optionally substituted by 1 to 3 substituents selected from (1) a halogen atom,
(2) a $C_{1-6}$ alkyl group optionally substituted by 1 to 3 halogen atoms,
(3) a $C_{1-6}$ alkoxy group, and
(4) a $C_{1-6}$ alkylenedioxy group.

[7] The compound or salt of the above-mentioned [1], wherein $R^2$ is a hydrogen atom.

[8] The compound or salt of the above-mentioned [1], wherein $R^1$ is a $C_{1-6}$ alkyl group optionally substituted by 1 to 3 substituents selected from
(1) a $C_{6-14}$ aryl group optionally substituted by 1 to 3 substituents selected from
(a) a halogen atom,
(b) a cyano group, and
(c) a $C_{1-6}$ alkoxy group optionally substituted by 1 to 3 halogen atoms
(2) a 5- or 6-membered monocyclic aromatic heterocyclic group optionally substituted by 1 to 3 substituents selected from
(a) a halogen atom,
(b) a cyano group, and
(c) a $C_{1-6}$ alkoxy group optionally substituted by 1 to 3 halogen atoms, and
(3) a 3- to 8-membered monocyclic non-aromatic heterocyclic group optionally substituted by 1 to 3 substituents selected from
(a) a halogen atom,
(b) a cyano group, and
(c) a $C_{1-6}$ alkoxy group optionally substituted by 1 to 3 halogen atoms;
$R^2$ is a hydrogen atom or a $C_{1-6}$ alkyl group;
$R^3$ is a 5- or 6-membered nitrogen-containing aromatic heterocyclic group optionally substituted by 1 to 3 halogen atoms;
ring A is a piperidine ring having no substituent other than $R^1$, $R^2$—O— and —C(=O)-ring B, or an oxa-9-azabicyclo[3.3.1]nonane ring having no substituent other than $R^1$, $R^2$—O— and —O(=O)-ring B; and
ring B is a 5- or 6-membered aromatic ring which is, in addition to $R^3$ and —C(=O)-ring A, optionally substituted by 1 to 3 substituents selected from
(1) a halogen atom,
(2) a $C_{1-6}$ alkyl group optionally substituted by 1 to 3 halogen atoms,
(3) a $C_{1-6}$ alkoxy group and
(4) a $C_{1-6}$ alkylenedioxy group.

[9] (4-benzyl-4-hydroxypiperidin-1-yl)(2,4'-bipyridin-3-yl)methanone or a salt thereof.

[10] 2,4'-bipyridin-3-yl(4-(4-fluorobenzyl)-4-hydroxypiperidin-1-yl)methanone or a salt thereof.

[11] 2,4'-bipyridin-3-yl(4-(2,4-difluorobenzyl)-4-hydroxypiperidin-1-yl)methanone or a salt thereof.

[12] (4-(4-fluorobenzyl)-4-hydroxypiperidin-1-yl)(2-(pyrimidin-4-yl)pyridin-3-yl)methanone or a salt thereof.

[13] A medicament comprising the compound or salt of the above-mentioned [1].

[14] The medicament of the above-mentioned [13], which is a cholesterol 24-hydroxylase inhibitor.

[15] The medicament of the above-mentioned [13], which is an agent for the prophylaxis or treatment of neurodegenerative disease.

[16] The medicament of the above-mentioned [15], wherein the neurodegenerative disease is Alzheimer's disease, mild cognitive impairment, Huntington's disease, Parkinson's disease or multiple sclerosis.

[17] The compound or salt of the above-mentioned [1] for use in the prophylaxis or treatment of neurodegenerative disease.

[18] The compound or salt of the above-mentioned [17], wherein the neurodegenerative disease is Alzheimer's disease, mild cognitive impairment, Huntington's disease, Parkinson's disease or multiple sclerosis.

[19] A method of inhibiting a cholesterol 24-hydroxylase in a mammal, which comprises administering an effective amount of the compound or salt of the above-mentioned [1] to a mammal.

[20] A method for the prophylaxis or treatment of neurodegenerative disease in a mammal, which comprises administering an effective amount of the compound or salt of the above-mentioned [1] to a mammal.

[21] The method of the above-mentioned [20], wherein the neurodegenerative disease is Alzheimer's disease, mild cognitive impairment, Huntington's disease, Parkinson's disease or multiple sclerosis.

[22] Use of the compound or salt of the above-mentioned [1] for the production of an agent for the prophylaxis or treatment of neurodegenerative disease.

[23] Use of the above-mentioned [22], wherein the neurodegenerative disease is Alzheimer's disease, mild cognitive impairment, Huntington's disease, Parkinson's disease or multiple sclerosis.

Effect of the Invention

Compound (I) has a superior CH24H inhibitory action, which is useful as an agent for the prophylaxis or treatment of neurodegenerative disease (e.g., Alzheimer's disease, mild cognitive impairment, Huntington's disease, Parkinson's disease, amyotrophic lateral sclerosis, traumatic brain injury, cerebral infarction, glaucoma, multiple sclerosis and the like), epilepsy, schizophrenia and the like.

DETAILED DESCRIPTION OF THE INVENTION

In the present specification, the "halogen atom" means a fluorine atom, a chlorine atom, a bromine atom or an iodine m atom.

In the present specification, the "$C_{1-6}$ alkyl (group)" means, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{2-6}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

In the present specification, the "$C_{2-6}$ alkynyl (group)" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, S-hexynyl or the like.

In the present specification, the "$C_{1-6}$ alkoxy (group)" means, for example, methoxy, ethoxy, propoxy, isopropoxy, butoxy, isobutoxy, sec-butoxy, tert-butoxy, pentyloxy, isopentyloxy, hexyloxy or the like.

In the present specification, the "$C_{2-6}$ alkenyloxy (group)" means, for example, vinyloxy, 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 3-hexenyloxy, 5-hexenyloxy or the like.

In the present specification, the "$C_{2-6}$ alkynyloxy (group)" means, for example, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1,1-dimethylprop-2-yn-1-yloxy, 1-hexynyloxy, 2-hexynyloxy, 3-hexynyloxy, 4-hexynyloxy, 5-hexynyloxy or the like.

In the present specification, the "$C_{1-6}$ alkylenedioxy (group)" means, for example, methylenedioxy, ethylenedioxy or the like.

In the present specification, the "$C_{1-6}$ alkoxy-carbonyl (group)" means, for example, methoxycarbonyl, ethoxycarbonyl, propoxycarbonyl, isopropoxycarbonyl, butoxycarbonyl, isobutoxycarbonyl, tert-butoxycarbonyl or the like.

In the present specification, the "$C_{1-6}$ alkyl-carbonyl (group)" means, for example, acetyl, propanoyl, butanoyl, 2-methylpropanoyl or the like.

In the present specification, the "mono-$C_{1-6}$ alkylamino (group)" means, for example, methylamino, ethylamino, propylamino, isopropylamino, butylamino, isobutylamino, tert-butylamino or the like.

In the present specification, the "di-$C_{1-6}$ alkylamino (group)" means, for example, dimethylamino, diethylamino, dipropylamino, diisopropylamino, dibutylamino, diisobutylamino, di-tert-butylamino or the like.

In the present specification, the "$C_{3-8}$ cycloalkyl (group)" means, for example, cyclopropyl, cyclobutyl, cyclopentyl, cyclohexyl, cycloheptyl, cyclooctyl or the like.

In the present specification, the "$C_{3-6}$ cycloalkyl (group)" means, for example, cycloalkyl having 3 to 6 carbon atoms, from among the above-mentioned $C_{3-5}$ cycloalkyl (group).

In the present specification, the "$C_{3-8}$ cycloalkyloxy (group)" means, for example, cyclopropyloxy, cyclobutyloxy, cyclopentyloxy, cyclohexyloxy, cycloheptyloxy, cyclooctyloxy or the like.

In the present specification, the "$C_{3-6}$ cycloalkyloxy (group)" means, for example, cyclopropyloxy, cyclobutyloxy, cyclopentyloxy, cyclohexyloxy or the like.

In the present specification, the "$C_{3-8}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) or the like.

In the present specification, the "$C_{3-8}$ cycloalkenyloxy (group)" means, for example, cyclopropenyloxy (e.g., 2-cyclopropen-1-yloxy), cyclobutenyloxy (e.g., 2-cyclobuten-1-yloxy), cyclopentenyloxy (e.g., 2-cyclopenten-1-yloxy, 3-cyclopenten-1-yloxy), cyclohexenyloxy (e.g., 2-cyclohexen-1-yloxy, 3-cyclohexen-1-yloxy) or the like.

In the present specification, the "$C_{6-14}$ aryl (group)" means, for example, phenyl, 1-naphthyl, 2-naphthyl or the like.

In the present specification, the "$C_{6-14}$ aryloxy (group)" means, for example, phenoxy, 1-naphthyloxy, 2-naphthyloxy or the like.

In the present specification, the "$C_{7-14}$ aralkyl (group)" means, for example, benzyl, phenethyl or the like.

In the present specification, the "$C_{7-14}$ aralkyloxy (group)" means, for example, benzyloxy, phenethyloxy or the like.

In the present specification, the "heterocyclic group" means an aromatic heterocyclic group or a non-aromatic heterocyclic group.

In the present specification, the "aromatic heterocyclic group" means a monocyclic aromatic heterocyclic group or a fused aromatic heterocyclic group.

In the present specification, examples of the "monocyclic aromatic heterocyclic group" include a 5- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized). Examples thereof include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

In the present specification, examples of the "fused aromatic heterocyclic group" include a 8- to 12-membered fused aromatic heterocyclic group, specifically, a group derived from a fused ring wherein a ring corresponding to the 5- to 7-membered monocyclic aromatic heterocyclic group is fused with a $C_{6-14}$ aromatic hydrocarbon; and a group derived from a fused ring wherein rings corresponding to the 5- to 7-membered monocyclic aromatic heterocyclic groups are fused. Examples thereof include quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl, 2H-imidazo[1,2-a]pyridin-3-yl), thienopyridyl (e.g., thieno[2,3-b]pyridin-3-yl), imidazopyrazinyl (e.g., 1H-imidazo[4,5-b]pyrazin-2-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

In the present specification, the "non-aromatic heterocyclic group" means a monocyclic non-aromatic heterocyclic group or a fused non-aromatic heterocyclic group.

In the present specification, examples of the "monocyclic non-aromatic heterocyclic group" include a 3- to 8-membered (preferably 5- or 6-membered) monocyclic non-aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized). Examples thereof include azetidinyl (e.g., 1-azetidinyl, 2-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), oxetanyl (e.g., oxetan-2-yl, oxetan-3-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), azepanyl (e.g., 1-azepanyl, 2-azepanyl, 3-azepanyl, 4-azepanyl), dihydropyridyl (e.g., dihydropyridin-1-yl, dihydropyridin-2-yl, dihydropyridin-3-yl, dihydropyridin-4-yl), tetrahydropyridyl (e.g., 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl) and the like.

In the present specification, examples of the "fused non-aromatic heterocyclic group" include a 8- to 12-membered fused non-aromatic heterocyclic group, specifically, a group derived from a fused ring wherein a ring corresponding to the 3- to 8-membered monocyclic non-aromatic heterocyclic group is fused with a $C_{6-14}$ aromatic hydrocarbon; a group derived from a fused ring wherein rings corresponding to the 3- to 8-membered monocyclic non-aromatic heterocyclic groups are fused; a group derived from a fused ring wherein a ring corresponding to the 3- to 8-membered monocyclic non-aromatic heterocyclic group is fused with a ring corresponding to the 5- to 7-membered monocyclic aromatic heterocyclic group; and a group wherein the above-mentioned group is partially saturated. Examples thereof include dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), dihydrobenzodioxinyl (e.g., 2,3-dihydro-1,4-benzodioxin-2-yl), dihydrobenzodioxepinyl (e.g., 3,4-dihydro-2H-1,5-benzodioxepin-2-yl), chromenyl (e.g., 4H-chromen-2-yl, 2H-chromen-3-yl), dihydrochromenyl (e.g., 3,4-dihydro-2H-chromen-2-yl), dihydroquinolyl (e.g., 1,2-dihydroquinolin-4-yl), tetrahydroquinolyl (e.g., 1,2,3,4-tetrahydroquinolin-4-yl), dihydroisoquinolyl (e.g., 1,2-dihydroisoquinolin-4-yl), tetrahydroisoquinolyl (e.g., 1,2,3,4-tetrahydroisoquinolin-4-yl), dihydrophthalazinyl (e.g., 1,4-dihydrophthalazin-4-yl) and the like.

In the present specification, examples of the "5- or 6-membered aromatic heterocyclic group" include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

In the present specification, examples of the "5- or 6-membered nitrogen-containing aromatic heterocyclic group" include a 5- or 6-membered nitrogen-containing aromatic heterocyclic group containing, as a ring-constituting atom besides carbon atoms, at least one nitrogen atom, and optionally containing 1 or 2 hetero atoms selected from an oxygen atom, a sulfur atom and a nitrogen atom. Examples thereof include pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

In the present specification, the "$C_{6-14}$ aromatic hydrocarbon" means, for example, benzene, naphthalene or the like.

In the present specification, the "5- or 6-membered aromatic ring" means, for example, benzene, a 5- or 6-membered aromatic heterocycle or the like.

In the present specification, examples of the "5- or 6-membered aromatic heterocycle" include a 5- or 6-membered monocyclic aromatic heterocycle containing, as a ring-constituting atom besides carbon atoms, 1 to 4 hetero atoms selected from an oxygen atom, a sulfur atom (optionally oxidized) and a nitrogen atom (optionally oxidized). Examples thereof include furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine and the like.

In the present specification, examples of the "5- or 6-membered nitrogen-containing aromatic heterocycle" include a 5- or 6-membered nitrogen-containing aromatic heterocycle containing, as a ring-constituting atom besides carbon atoms, at least one nitrogen atom, and optionally containing 1 or 2 hetero atoms selected from an oxygen atom, a sulfur atom and a nitrogen atom. Examples thereof include pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine and the like.

Each symbol of the formula (I) is explained below.

In the formula (I), $R^1$ is an optionally substituted $C_{1-6}$ alkyl group.

In the formula (I), $R^2$ is a hydrogen atom or an optionally substituted $C_{1-6}$ alkyl group.

The "$C_{1-6}$ alkyl group" of "optionally substituted $C_{1-6}$ alkyl group" for $R^1$ or $R^2$ optionally has 1 to 5 (preferably 1 to 3) substituents at substitutable positions. Examples of the substituent include substituents selected from the following Substituent Group A. When the number of substituents is two or more, the substituents may be the same or different.

Substituent Group A:
(1) a halogen atom;
(2) a cyano group;
(3) a nitro group;
(4) a hydroxy group;
(5) a $C_{3-8}$ cycloalkyl group optionally substituted by 1 to 3 substituents selected from
  (a) a halogen atom,
  (b) a cyano group
  (c) a $C_{1-6}$ alkyl group optionally substituted by 1 to 3 halogen atoms, and
  (d) a $C_{1-6}$ alkoxy group optionally substituted by 1 to 3 halogen atoms;
(6) a $C_{6-14}$ aryl group optionally substituted by 1 to 3 substituents selected from
  (a) a halogen atom,
  (b) a cyano group,
  (c) a $C_{1-6}$ alkyl group optionally substituted by 1 to 3 halogen atoms, and
  (d) a $C_{1-6}$ alkoxy group optionally substituted by 1 to 3 halogen atoms;
(7) a $C_{1-6}$ alkoxy group optionally substituted by 1 to 3 substituents selected from
  (a) a halogen atom,
  (b) a cyano group,
  (c) a $C_{3-8}$ cycloalkyl group optionally having 1 to 3 halogen atoms,
  (d) a $C_{3-8}$ cycloalkenyl group optionally having 1 to 3 halogen atoms,
  (e) a $C_{6-14}$ aryl group optionally having 1 to 3 halogen atoms, and
  (f) a 5- or 6-membered monocyclic aromatic heterocyclic group;
(8) a $C_{2-6}$ alkenyloxy group (e.g., vinyloxy, propenyloxy, butenyloxy, pentenyloxy, hexenyloxy) optionally having 1 to 3 halogen atoms;
(9) a $C_{2-6}$ alkynyloxy group (e.g., ethynyloxy, propynyloxy, butynyloxy, pentynyloxy, hexynyloxy) optionally having 1 to 3 halogen atoms;
(10) a $C_{3-8}$ cycloalkyloxy group (e.g., cyclopropyloxy, cyclobutyloxy, cyclopentyloxy, cyclohexyloxy) optionally having 1 to 3 halogen atoms;
(11) a $C_{3-8}$ cycloalkenyloxy group (e.g., cyclopropenyloxy, cyclobutenyloxy, cyclopentenyloxy, cyclohexenyloxy) optionally having 1 to 3 halogen atoms;
(12) a $C_{6-14}$ aryloxy group optionally having 1 to 3 halogen atoms;
(13) a $C_{7-14}$ aralkyloxy group optionally having 1 to 3 halogen atoms;
(14) a carbamoyl group optionally mono- or di-substituted by substituent(s) selected from
  (a) a $C_{1-6}$ alkyl group,
  (b) a $C_{3-6}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) a 8- to 12-membered fused aromatic heterocyclic group,
  (g) a 3- to 8-membered monocyclic non-aromatic heterocyclic group, and (h) a 8- to 12-membered fused non-aromatic heterocyclic group;

(15) a sulfamoyl group optionally mono- or di-substituted by substituent(s) selected from
  (a) a $C_{1-6}$ alkyl group,
  (b) a $C_{3-6}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) a 8- to 12-membered fused aromatic heterocyclic group,
  (g) a 3- to 8-membered monocyclic non-aromatic heterocyclic group, and
  (h) a 8- to 12-membered fused non-aromatic heterocyclic group;

(16) a formyl group;
(17) a $C_{1-6}$ alkyl-carbonyl group;
(18) a $C_{2-6}$ alkenyl-carbonyl group (e.g., acryloyl, butenoyl, pentenoyl, hexenoyl, heptenoyl);
(19) a $C_{2-6}$ alkynyl-carbonyl group (e.g., propioloyl, propynylcarbonyl, butynylcarbonyl, pentynylcarbonyl, hexynylcarbonyl);
(20) a $C_{3-8}$ cycloalkyl-carbonyl group (e.g., cyclopropylcarbonyl, cyclobutylcarbonyl, cyclopentylcarbonyl, cyclohexylcarbonyl);
(21) a $C_{3-8}$ cycloalkenyl-carbonyl group (e.g., cyclopropenylcarbonyl, cyclobutenylcarbonyl, cyclopentenylcarbonyl, cyclohexenylcarbonyl);
(22) a $C_{6-14}$ aryl-carbonyl group (e.g., benzoyl, 1-naphthylcarbonyl, 2-naphthylcarbonyl);
(23) a $C_{3-8}$ cycloalkyl-$C_{1-6}$ alkyl-carbonyl group (e.g., cyclopropylacetyl, 3-cyclopropylpropionyl, cyclobutylacetyl, cyclopentylacetyl, cyclohexylacetyl, cyclohexylpropionyl);
(24) a $C_{3-8}$ cycloalkenyl-$C_{1-6}$ alkyl-carbonyl group (e.g., cyclopentenylacetyl, cyclohexenylacetyl, 3-cyclohexenylpropionyl, 3-cyclohexenylpropionyl);
(25) a $C_{7-14}$ aralkyl-carbonyl group (e.g., phenylacetyl, phenylpropionyl);
(26) a 5- or 6-membered monocyclic aromatic heterocyclylcarbonyl group (e.g., furylcarbonyl, thienylcarbonyl, pyrrolylcarbonyl, oxazolylcarbonyl, isooxazolylcarbonyl, thiazolylcarbonyl, isothiazolylcarbonyl, imidazolylcarbonyl, pyridylcarbonyl, pyrazolylcarbonyl);
(27) a 8- to 12-membered fused aromatic heterocyclylcarbonyl group (e.g., benzofuranylcarbonyl, isobenzofuranylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(28) a 3- to 8-membered monocyclic non-aromatic heterocyclylcarbonyl group (e.g., oxiranylcarbonyl, azetidinylcarbonyl, oxetanylcarbonyl, thietanylcarbonyl, pyrrolidinylcarbonyl, tetrahydrofurylcarbonyl, thioranylcarbonyl, piperidylcarbonyl);
(29) a 8- to 12-membered fused non-aromatic heterocyclylcarbonyl group (e.g., dihydrobenzofuranyl);
(30) an amino group optionally mono- or di-substituted by substituent(s) selected from
  (a) a $C_{1-8}$ alkyl group optionally having 1 to 3 halogen atoms,
  (b) a $C_{1-8}$ alkyl-carbonyl group optionally having 1 to 3 halogen atoms,
  (c) a $C_{3-8}$ cycloalkyl-carbonyl group,
  (d) a $C_{8-14}$ aryl-carbonyl group optionally having 1 to 3 halogen atoms,
  (e) a 5- or 6-membered monocyclic aromatic heterocyclylcarbonyl group,
  (f) a 8- to 12-membered fused aromatic heterocyclylcarbonyl group,
  (g) a 3- to 8-membered monocyclic non-aromatic heterocyclylcarbonyl group, and
  (h) a 8- to 12-membered fused non-aromatic heterocyclylcarbonyl group;

(31) a sulfanyl group;
(32) a $C_{1-6}$ alkylsulfanyl group (e.g., methylsulfanyl, ethylsulfanyl);
(33) a $C_{2-6}$ alkenylsulfanyl group (e.g., vinylsulfanyl, propenylsulfanyl);
(34) a $C_{2-6}$ alkynylsulfanyl group (e.g., ethynylsulfanyl, propynylsulfanyl);
(35) a $C_{3-8}$ cycloalkylsulfanyl group (e.g., cyclopropylsulfanyl, cyclobutylsulfanyl);
(36) a $C_{3-8}$ cycloalkenylsulfanyl group (e.g., cyclopropenylsulfanyl, cyclobutenylsulfanyl);
(37) a $C_{6-14}$ arylsulfanyl group (e.g., phenylsulfanyl);
(38) a $C_{3-8}$ cycloalkyl-$C_{1-6}$ alkylsulfanyl group (e.g., cyclopropylmethylsulfanyl);
(39) a $C_{3-8}$ cycloalkenyl-$C_{1-6}$ alkylsulfanyl group (e.g., cyclopentenylmethylsulfanyl);
(40) a $C_{1-6}$ alkylsulfinyl group (e.g., methylsulfinyl, ethylsulfinyl);
(41) a $C_{2-6}$ alkenylsulfinyl group (e.g., vinylsulfinyl, propenylsulfinyl);
(42) a $C_{2-6}$ alkynylsulfinyl group (e.g., ethynylsulfinyl, propynylsulfinyl); (43) a $C_{3-8}$ cycloalkylsulfinyl group (e.g., cyclopropylsulfinyl, cyclobutylsulfinyl);
(44) a $C_{3-8}$ cycloalkenylsulfinyl group (e.g., cyclopropenylsulfinyl, cyclobutenylsulfinyl);
(45) a $C_{6-14}$ arylsulfinyl group (e.g., phenylsulfinyl);
(46) a $C_{3-8}$ cycloalkyl-$C_{1-6}$ alkylsulfinyl group (e.g., cyclopropylmethylsulfinyl);
(47) a $C_{3-8}$ cycloalkenyl-$C_{1-6}$ alkylsulfinyl group (e.g., cyclopentenylmethylsulfinyl);
(48) a $C_{1-6}$ alkylsulfonyl group (e.g., methylsulfonyl, ethylsulfonyl);
(49) a $C_{2-6}$ alkenylsulfonyl group (e.g., vinylsulfonyl, propenylsulfonyl);
(50) a $C_{2-6}$ alkynylsulfonyl group (e.g., ethynylsulfonyl, propynylsulfonyl);
(51) a $C_{3-8}$ cycloalkylsulfonyl group (e.g., cyclopropylsulfonyl, cyclobutylsulfonyl);
(52) a $C_{3-8}$ cycloalkenylsulfonyl group (e.g., cyclopropenylsulfonyl, cyclobutenylsulfonyl);
(53) a $C_{6-14}$ arylsulfonyl group (e.g., phenylsulfonyl);
(54) a $C_{3-8}$ cycloalkyl-$C_{1-6}$ alkylsulfonyl group (e.g., cyclopropylmethylsulfonyl);
(55) a $C_{3-8}$ cycloalkenyl-$C_{1-6}$ alkylsulfonyl group (e.g., cyclopentenylmethylsulfonyl);
(56) a $C_{6-14}$ aryl-$C_{1-6}$ alkylsulfonyl group (e.g., benzylsulfonyl);
(57) a 5- or 6-membered monocyclic aromatic heterocyclylsulfonyl group (e.g., furylsulfonyl, thienylsulfonyl, pyridylsulfonyl);
(58) a 8- to 12-membered fused aromatic heterocyclylsulfonyl group (e.g., benzofuranylsulfonyl, isobenzofuranylsulfonyl);
(59) a 3- to 8-membered monocyclic non-aromatic heterocyclylsulfonyl group (e.g., oxiranylsulfonyl, azetidinylsulfonyl);
(60) a 8- to 12-membered fused non-aromatic heterocyclylsulfonyl group (e.g., dihydrobenzofuranylsulfonyl);

(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl, morpholinyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(62) a 8- to 12-membered fused aromatic heterocyclic group (e.g., benzofuranyl, isobenzofuranyl, benzothienyl, isobenzothienyl, indolyl, isoindolyl, indazolyl, benzimidazolyl, benzoxazolyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(63) a 3- to 8-membered monocyclic non-aromatic heterocyclic group (e.g., oxiranyl, azetidinyl, oxetanyl, thietanyl, pyrrolidinyl, tetrahydrofuryl, thiolanyl, piperidyl, piperazinyl, dihydrooxadiazolyl, thiazolinyl) optionally substituted by 1 to 3 substituents selected from
  (a) a halogen atom,
  (b) a $C_{1-6}$ alkyl group optionally substituted by 1 to 3 halogen atoms,
  (c) a $C_{1-6}$ alkoxy group optionally substituted by 1 to 3 halogen atoms, and
  (d) an oxo group;
(64) a 8- to 12-membered fused non-aromatic heterocyclic group (e.g., dihydrobenzofuranyl) optionally substituted by 1 to 3 substituents selected from
  (a) a halogen atom,
  (b) a $C_{1-6}$ alkyl group optionally substituted by 1 to 3 halogen atoms,
  (c) a $C_{1-6}$ alkoxy group optionally substituted by 1 to 3 halogen atoms, and
  (d) an oxo group;
(65) a 5- or 6-membered monocyclic aromatic heterocyclyloxy group (e.g., furyloxy, thienyloxy, pyrrolyloxy, oxazolyloxy, isooxazolyloxy, thiazolyloxy, isothiazolyloxy, imidazolyloxy, pyridyloxy, pyrazolyloxy);
(66) a 8- to 12-membered fused aromatic heterocyclyloxy group (e.g., benzofuranyloxy, isobenzofuranyloxy, benzothienyloxy, isobenzothienyloxy, indolyloxy, isoindolyloxy, indazolyloxy, benzimidazolyloxy, benzoxazolyloxy);
(67) a 3- to 8-membered monocyclic non-aromatic heterocyclyloxy group (e.g., oxiranyloxy, azetidinyloxy, oxetanyloxy, thietanyloxy, pyrrolidinyloxy, tetrahydrofuryloxy, thioranyloxy, piperidyloxy);
(68) a 8- to 12-membered fused non-aromatic heterocyclyloxy group (e.g., dihydrobenzofuranyloxy);
(69) a carboxy group;
(70) a $C_{1-6}$ alkoxy-carbonyl group;
(71) a $C_{2-6}$ alkenyloxy-carbonyl group (e.g., vinyloxycarbonyl, propenyloxycarbonyl, butenyloxycarbonyl, pentenyloxycarbonyl, hexenyloxycarbonyl);
(72) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl);
(73) a $C_{3-8}$ cycloalkyloxy-carbonyl group (e.g., cyclopropyloxycarbonyl, cyclobutyloxycarbonyl, cyclopentyloxycarbonyl, cyclohexyloxycarbonyl);
(74) a $C_{3-8}$ cycloalkenyloxy-carbonyl group (e.g., cyclopropenyloxycarbonyl, cyclobutenyloxycarbonyl, cyclopentenyloxycarbonyl, cyclohexenyloxycarbonyl);
(75) a $C_{6-14}$ aryloxy-carbonyl group (e.g., phenoxycarbonyl, 1-naphthyloxycarbonyl, 2-naphthyloxycarbonyl);
(76) a $C_{3-8}$ cycloalkyl-$C_{1-6}$ alkoxy-carbonyl group (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl);
(77) a $C_{3-8}$ cycloalkenyl-$C_{1-6}$ alkoxy-carbonyl group (e.g., cyclopentenylmethyloxycarbonyl, cyclohexenylmethyloxycarbonyl, cyclohexenylethyloxycarbonyl, cyclohexenylpropyloxycarbonyl);
(78) a $C_{7-14}$ aralkyloxy-carbonyl group (e.g., benzyloxycarbonyl, phenethyloxycarbonyl);
(79) a mono-$C_{1-6}$ alkylthiocarbamoyl group (e.g., methylthiocarbamoyl, ethylthiocarbamoyl, propylthiocarbamoyl);
(80) a di-$C_{1-6}$ alkylthiocarbamoyl group (e.g., dimethylthiocarbamoyl, diethylthiocarbamoyl, dipropylthiocarbamoyl);
(81) a $C_{1-6}$ alkyl-carbonyloxy group (e.g., acetyloxy, propanoyloxy, butanoyloxy, 2-methylpropanoyloxy);
(82) an imino group optionally substituted by a hydroxy group; and
(83) a $C_{1-6}$ alkylenedioxy group (e.g., methylenedioxy, ethylenedioxy).

In one preferable embodiment, $R^1$ is preferably a $C_{1-6}$ alkyl group (preferably a $C_{1-3}$ alkyl group (e.g., methyl, ethyl, propyl, isopropyl)) optionally substituted by 1 to 3 substituents selected from
  (1) a $C_{6-14}$ aryl group (e.g., phenyl) optionally substituted by 1 to 3 substituents selected from
    (a) a halogen atom (e.g., a fluorine atom),
    (b) a cyano group, and
    (c) a $C_{1-6}$ alkoxy group (e.g., methoxy) optionally substituted by 1 to 3 halogen atoms (e.g., a fluorine atom),
  (2) a 5- or 6-membered monocyclic aromatic heterocyclic group (e.g., pyridyl), and
  (3) a 3- to 8-membered monocyclic non-aromatic heterocyclic group (e.g., thiazolinyl).

In another preferable embodiment, $R^1$ is preferably a $C_{1-6}$ alkyl group (preferably a alkyl group (e.g., methyl, ethyl, propyl, isopropyl)) optionally substituted by 1 to 3 substituents selected from
  (1) a $C_{6-14}$ aryl group (e.g., phenyl) optionally substituted by 1 to 3 substituents selected from
    (a) a halogen atom (e.g., a fluorine atom),
    (b) a cyano group, and
    (c) a $C_{1-6}$ alkoxy group (e.g., methoxy) optionally substituted by 1 to 3 halogen atoms (e.g., a fluorine atom),
  (2) a 5- or 6-membered monocyclic aromatic heterocyclic group (e.g., pyridyl) optionally substituted by 1 to 3 substituents selected from
    (a) a halogen atom (e.g., a fluorine atom),
    (b) a cyano group, and
    (c) a $C_{1-6}$ alkoxy group (e.g., methoxy) optionally substituted by 1 to 3 halogen atoms (e.g., a fluorine atom), and
  (3) a 3- to 8-membered monocyclic non-aromatic heterocyclic group (e.g., thiazolinyl) optionally substituted by 1 to 3 substituents selected from
    (a) a halogen atom (e.g., a fluorine atom),
    (b) a cyano group, and (c) a $C_{1-6}$ alkoxy group (e.g., methoxy) optionally substituted by 1 to 3 halogen atoms (e.g., a fluorine atom).

$R^1$ is more preferably a $C_{1-6}$ alkyl group (preferably a $C_{1-3}$ alkyl group (e.g., methyl, ethyl, propyl, isopropyl)) optionally substituted by 1 to 3 substituents selected from
(1) a $C_{6-14}$ aryl group (e.g., phenyl) optionally substituted by 1 to 3 substituents selected from
  (a) a halogen atom (e.g., a fluorine atom),
  (b) a cyano group, and
  (c) a $C_{1-6}$ alkoxy group (e.g., methoxy) optionally substituted by 1 to 3 halogen atoms (e.g., a fluorine atom),
(2) a 5- or 6-membered monocyclic aromatic heterocyclic group (e.g., pyridyl), and
(3) a 3- to 8-membered monocyclic non-aromatic heterocyclic group (e.g., thiazolinyl).

$R^2$ is preferably a hydrogen atom or a $C_{1-6}$ alkyl group (preferably a $C_{1-3}$ alkyl group (e.g., methyl)), particularly preferably a hydrogen atom.

In the formula (I), $R^3$ is an optionally substituted 5- or 6-membered aromatic heterocyclic group.

The "5- or 6-membered aromatic heterocyclic group" of the "optionally substituted 5- or 6-membered aromatic heterocyclic group" for $R^3$ is preferably a 5- or 6-membered nitrogen-containing aromatic heterocyclic group (preferably pyridyl, pyrimidinyl, pyridazinyl or oxazolyl), more preferably a group represented by

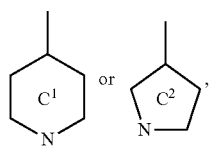

wherein
ring $C^1$ is an optionally substituted 6-membered nitrogen-containing aromatic heterocycle containing at least one nitrogen atom; and
ring $C^2$ is an optionally substituted 5-membered nitrogen-containing aromatic heterocycle containing at least one nitrogen atom,
(preferably pyridyl, pyrimidinyl, pyridazinyl or oxazolyl).

The "5- or 6-membered aromatic heterocyclic group" of the "optionally substituted 5- or 6-membered aromatic heterocyclic group" for $R^3$ optionally has 1 to 5 (preferably 1 to 3) substituents at substitutable positions. Examples of the substituent include substituents selected from the following Substituent Group B. When the number of substituents is two or more, the substituents may be the same or different.

Substituent Group B:
(1) the above-mentioned Substituent Group A;
(2) a $C_{1-8}$ alkyl group optionally substituted by 1 to 3 substituents selected from
  (a) a halogen atom,
  (b) a cyano group,
  (c) a hydroxy group,
  (d) a $C_{3-8}$ cycloalkyl group optionally substituted by 1 to 3 substituents selected from
    (i) a halogen atom,
    (ii) a cyano group, and
    (iii) a $C_{1-6}$ alkyl group optionally substituted by 1 to 3 halogen atoms;
  (e) a $C_{6-14}$ aryl group optionally substituted by 1 to 3 substituents selected from
    (i) a halogen atom,
    (ii) a cyano group, and
    (iii) a $C_{1-6}$ alkyl group optionally substituted by 1 to 3 halogen atoms,
  (f) a $C_{1-8}$ alkoxy group optionally substituted by 1 to 3 halogen atoms,
  (g) an amino group optionally mono- or di-substituted by $C_{1-6}$ alkyl group(s),
  (h) a 5- or 6-membered monocyclic aromatic heterocyclic group,
  (i) a 8- to 12-membered fused aromatic heterocyclic group,
  (j) a 3- to 8-membered monocyclic non-aromatic heterocyclic group,
  (k) a 8- to 12-membered fused non-aromatic heterocyclic group,
  (l) a carboxy group, and
  (m) a $C_{1-8}$ alkoxy-carbonyl group optionally substituted by 1 to 3 halogen atoms;
(3) a $C_{2-6}$ alkenyl group optionally substituted by 1 to 3 substituents selected from
  (a) a halogen atom,
  (b) a hydroxy group,
  (c) a $C_{1-6}$ alkoxy group,
  (d) an amino group optionally mono- or di-substituted by $C_{1-6}$ alkyl group(s),
  (e) a carboxy group, and
  (f) a $C_{2-6}$ alkoxy-carbonyl group;
(4) a $C_{7-24}$ aralkyl group optionally substituted by 1 to 3 substituents selected from
  (a) a halogen atom,
  (b) a hydroxy group,
  (c) a $C_{2-6}$ alkoxy group, and
  (d) a $C_{2-6}$ alkyl group optionally substituted by 1 to 3 halogen atoms; and
(5) an oxo group.

In one preferable embodiment, $R^3$ is preferably a 5- or 6-membered aromatic heterocyclic group (preferably pyridyl, pyrimidinyl, pyridazinyl or oxazolyl) optionally substituted by 1 to 3 halogen atoms (e.g., a fluorine atom).

In another preferable embodiment, $R^3$ is preferably an optionally substituted 5- or 6-membered nitrogen-containing aromatic heterocyclic group (preferably pyridyl, pyrimidinyl, pyridazinyl or oxazolyl).

$R^3$ is more preferably a 5- or 6-membered nitrogen-containing aromatic heterocyclic group (preferably pyridyl, pyrimidinyl, pyridazinyl or oxazolyl) optionally substituted by 1 to 3 halogen atoms (e.g., a fluorine atom).

$R^3$ is particularly preferably a group represented by

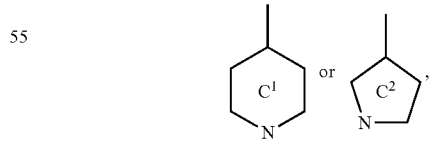

wherein
ring $C^1$ is an optionally substituted 6-membered nitrogen-containing aromatic heterocycle containing at least one nitrogen atom; and
ring $C^2$ is an optionally substituted 5-membered nitrogen-containing aromatic heterocycle containing at least one nitrogen atom, (preferably pyridyl, pyrimidinyl, pyridazinyl or oxazolyl), each of which is optionally substituted by 1 to 3 halogen atoms (e.g., a fluorine atom).

In the formula (I), ring A is a further optionally substituted piperidine ring (the piperidine ring is optionally bridged).

The "piperidine ring" of the "further optionally substituted piperidine ring" for ring A is optionally bridged. Examples of the bridged piperidine ring include oxa-9-azabicyclo[3.3.1]nonane and the like.

The "piperidine ring" of the "further optionally substituted piperidine ring" for ring A optionally has, besides $R^1$, $R^2$—O— and —C(=O)-ring B, 1 to 4 (preferably 1 to 3) substituents at substitutable positions. Examples of the substituent include substituents selected from the above-mentioned Substituent Group B. When the number of substituents is two or more, the substituents may be the same or different.

Ring A is preferably a piperidine ring having no substituent other than $R^1$, $R^2$—O— and —C(=O)-ring B, or an oxa-9-azabicyclo[3.3.1]nonane ring having no substituent other than $R^1$, $R^2$—O— and —C(=O)-ring B.

Ring A is more preferably a piperidine ring having no substituent other than $R^1$, $R^2$—O— and —C(=O)-ring B.

In the formula (I), ring B is a further optionally substituted 5- or 6-membered aromatic ring (X and Y are independently a carbon atom or a nitrogen atom).

In one preferable embodiment, the "5- or 6-membered aromatic ring" of the "further optionally substituted 5- or 6-membered aromatic ring" for ring B is preferably benzene, thiazole, isoxazole, pyrazole, pyridine or pyrazine (X and Y are independently a carbon atom or a nitrogen atom), more preferably

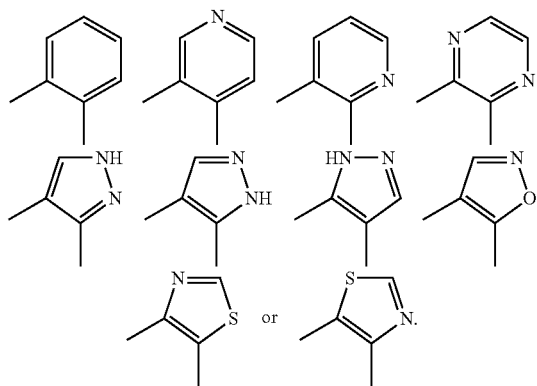

In another preferable embodiment, the "5- or 6-membered aromatic ring" of the "further optionally substituted 5- or 6-membered aromatic ring" for ring B is preferably a 6-membered aromatic ring (X and Y are independently a carbon atom or a nitrogen atom), more preferably benzene, pyridine or pyrazine.

The "5- or 6-membered aromatic ring" of the "further optionally substituted 5- or 6-membered aromatic ring" for ring B optionally has, besides $R^3$ and —C(=O)-ring A, 1 to 4 (preferably 1 to 3) substituents at substitutable positions. Examples of the substituent include substituents selected from the above-mentioned Substituent Group B. When the number of substituents is two or more, the substituents may be the same or different.

In one preferable embodiment, ring B is preferably a 5- or 6-membered aromatic ring (preferably benzene, thiazole, isoxazole, pyrazole, pyridine or pyrazine) (X and Y are independently a carbon atom or a nitrogen atom), which is, in addition to $R^3$ and —C(=O)-ring A, optionally substituted by 1 to 3 substituents selected from (1) a halogen atom (e.g., a fluorine atom, a chlorine atom),
(2) a $C_{1-6}$ alkyl group (e.g., methyl, tert-butyl) optionally substituted by 1 to 3 halogen atoms (e.g., a fluorine atom),
(3) a $C_{1-6}$ alkoxy group (e.g., methoxy), and
(4) a $C_{1-6}$ alkylenedioxy group (e.g., methylenedioxy), more preferably benzene, thiazole, isoxazole, pyrazole, pyridine or pyrazine (X and Y are independently a carbon atom or a nitrogen atom), each of which is, in addition to $R^3$ and —C(=O)-ring A, optionally substituted by 1 to 3 substituents selected from (1) a halogen atom (e.g., a fluorine atom, a chlorine atom),
(2) a $C_{1-6}$ alkyl group (e.g., methyl, tert-butyl) optionally substituted by 1 to 3 halogen atoms (e.g., a fluorine atom),
(3) a $C_{1-6}$ alkoxy group (e.g., methoxy), and
(4) a $C_{1-6}$ alkylenedioxy group (e.g., methylenedioxy), particularly preferably

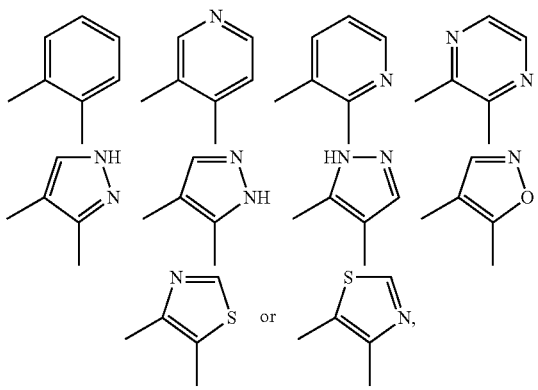

each of which is, in addition to $R^3$ and —C(=O)-ring A, optionally substituted by 1 to 3 substituents selected from
(1) a halogen atom (e.g., a fluorine atom, a chlorine atom),
(2) a $C_{1-6}$ alkyl group (e.g., methyl, tert-butyl) optionally substituted by 1 to 3 halogen atoms (e.g., a fluorine atom),
(3) a $C_{1-6}$ alkoxy group (e.g., methoxy), and
(4) a $C_{1-6}$ alkylenedioxy group (e.g., methylenedioxy).

In another preferable embodiment, ring B is preferably a 6-membered aromatic ring (X and Y are independently a carbon atom or a nitrogen atom, preferably benzene, pyridine or pyrazine), which is, in addition to $R^3$ and —C(=O)-ring A, optionally substituted by 1 to 3 substituents selected from (1) a halogen atom (e.g., a fluorine atom, a chlorine atom),
(2) a $C_{1-6}$ alkyl group (e.g., methyl, tert-butyl) optionally substituted by 1 to 3 halogen atoms (e.g., a fluorine atom),
(3) a $C_{1-6}$ alkoxy group (e.g., methoxy), and
(4) a $C_{1-6}$ alkylenedioxy group (e.g., methylenedioxy).

Preferable examples of compound (I) include the following compounds.

[Compound A]
Compound (I) wherein
$R^1$ is a $C_{1-6}$ alkyl group (preferably a $C_{1-3}$ alkyl group (e.g., methyl, ethyl, propyl, isopropyl)) optionally substituted by 1 to 3 substituents selected from (1) a $C_{6-14}$ aryl group (e.g., phenyl) optionally substituted by 1 to 3 substituents selected from
   (a) a halogen atom (e.g., a fluorine atom),
   (b) a cyano group, and
   (c) a $C_{1-6}$ alkoxy group (e.g., methoxy) optionally substituted by 1 to 3 halogen atoms (e.g., a fluorine atom),
(2) a 5- or 6-membered monocyclic aromatic heterocyclic group (e.g., pyridyl), and
(3) a 3- to 8-membered monocyclic non-aromatic heterocyclic group (e.g., thiazolinyl);

$R^2$ is a hydrogen atom or a $C_{1-6}$ alkyl group (preferably a $C_{1-3}$ alkyl group (e.g., methyl));
$R^3$ is a 5- or 6-membered aromatic heterocyclic group (preferably pyridyl, pyrimidinyl, pyridazinyl or oxazolyl) optionally substituted by 1 to 3 halogen atoms (e.g., a fluorine atom);
ring A is a piperidine ring having no substituent other than $R^1$, $R^2$—O— and —C(=O)-ring B; and
ring B is a 5- or 6-membered aromatic ring (preferably benzene, thiazole, isoxazole, pyrazole, pyridine or pyrazine) (X and Y are independently a carbon atom or a nitrogen atom), which is, in addition to $R^3$ and —C(=O)-ring A, optionally substituted by 1 to 3 substituents selected from
   (1) a halogen atom (e.g., a fluorine atom, a chlorine atom),
   (2) a $C_{1-6}$ alkyl group (e.g., methyl, tert-butyl) optionally substituted by 1 to 3 halogen atoms (e.g., a fluorine atom),
   (3) a $C_{1-6}$ alkoxy group (e.g., methoxy), and
   (4) a $C_{1-6}$ alkylenedioxy group (e.g., methylenedioxy), or a salt thereof.

[Compound B1]
Compound (I) wherein
$R^1$ is a $C_{1-6}$ alkyl group (preferably a $C_{1-3}$ alkyl group (e.g., methyl, ethyl, propyl, isopropyl)) optionally substituted by 1 to 3 substituents selected from
   (1) a $C_{6-14}$ aryl group (e.g., phenyl) optionally substituted by 1 to 3 substituents selected from
      (a) a halogen atom (e.g., a fluorine atom),
      (b) a cyano group, and
      (c) a $C_{1-6}$ alkoxy group (e.g., methoxy) optionally substituted by 1 to 3 halogen atoms (e.g., a fluorine atom),
   (2) a 5- or 6-membered monocyclic aromatic heterocyclic group (e.g., pyridyl), and
   (3) a 3- to 8-membered monocyclic non-aromatic heterocyclic group (e.g., thiazolinyl);
$R^2$ is a hydrogen atom or a $C_{1-6}$ alkyl group (preferably a $C_{1-3}$ alkyl group (e.g., methyl)) (preferably a hydrogen atom);
$R^3$ is a 5- or 6-membered nitrogen-containing aromatic heterocyclic group (preferably pyridyl, pyrimidinyl, pyridazinyl or oxazolyl) optionally substituted by 1 to 3 halogen atoms (e.g., a fluorine atom);
ring A is a piperidine ring having no substituent other than $R^1$, $R^2$—O— and —C(=O)-ring B; and
ring B is benzene, thiazole, isoxazole, pyrazole, pyridine or pyrazine (X and Y are independently a carbon atom or a nitrogen atom), each of which is, in addition to $R^3$ and —C(=O)-ring A, optionally substituted by 1 to 3 substituents selected from
   (1) a halogen atom (e.g., a fluorine atom, a chlorine atom),
   (2) a $C_{1-6}$ alkyl group (e.g., methyl, tert-butyl) optionally substituted by 1 to 3 halogen atoms (e.g., a fluorine atom),
   (3) a $C_{1-6}$ alkoxy group (e.g., methoxy), and
   (4) a $C_{1-6}$ alkylenedioxy group (e.g., methylenedioxy), or a salt thereof.

[Compound B2]
Compound (I) wherein
$R^1$ is a $C_{1-6}$ alkyl group (preferably a $C_{1-3}$ alkyl group (e.g., methyl, ethyl, propyl, isopropyl)) optionally substituted by 1 to 3 substituents selected from
   (1) a $C_{6-14}$ aryl group (e.g., phenyl) optionally substituted by 1 to 3 substituents selected from
      (a) a halogen atom (e.g., a fluorine atom),
      (b) a cyano group, and
      (c) a $C_{1-6}$ alkoxy group (e.g., methoxy) optionally substituted by 1 to 3 halogen atoms (e.g., a fluorine atom),
   (2) a 5- or 6-membered monocyclic aromatic heterocyclic group (e.g., pyridyl), and
   (3) a 3- to 8-membered monocyclic non-aromatic heterocyclic group (e.g., thiazolinyl);
$R^2$ is a hydrogen atom or a $C_{1-6}$ alkyl group (preferably a $C_{1-3}$ alkyl group (e.g., methyl)) (preferably a hydrogen atom);
$R^3$ is a 5- or 6-membered nitrogen-containing aromatic heterocyclic group (preferably pyridyl, pyrimidinyl, pyridazinyl or oxazolyl) optionally substituted by 1 to 3 halogen atoms (e.g., a fluorine atom);
ring A is a piperidine ring having no substituent other than $R^1$, $R^2$—O— and —C(=O)-ring B; and
ring B is a 6-membered aromatic ring (X and Y are independently a carbon atom or a nitrogen atom, preferably benzene, pyridine or pyrazine), which is, in addition to $R^3$ and —C(=O)-ring A, optionally substituted by 1 to 3 substituents selected from
   (1) a halogen atom (e.g., a fluorine atom, a chlorine atom),
   (2) a $C_{1-6}$ alkyl group (e.g., methyl, tert-butyl) optionally substituted by 1 to 3 halogen atoms (e.g., a fluorine atom),
   (3) a $C_{1-6}$ alkoxy group (e.g., methoxy), and
   (4) a $C_{1-6}$ alkylenedioxy group (e.g., methylenedioxy), or a salt thereof.

[Compound C]
Compound (I) wherein
$R^1$ is a $C_{1-6}$ alkyl group (preferably a $C_{1-3}$ alkyl group (e.g., methyl, ethyl, propyl, isopropyl)) optionally substituted by 1 to 3 substituents selected from
   (1) a $C_{6-14}$ aryl group (e.g., phenyl) optionally substituted by 1 to 3 substituents selected from
      (a) a halogen atom (e.g., a fluorine atom),
      (b) a cyano group, and
      (c) a $C_{1-6}$ alkoxy group (e.g., methoxy) optionally substituted by 1 to 3 halogen atoms (e.g., a fluorine atom),
   (2) a 5- or 6-membered monocyclic aromatic heterocyclic group (e.g., pyridyl), and
   (3) a 3- to 8-membered monocyclic non-aromatic heterocyclic group (e.g., thiazolinyl);
$R^2$ is a hydrogen atom or a $C_{1-6}$ alkyl group (preferably a $C_{1-3}$ alkyl group (e.g., methyl)) (preferably a hydrogen atom);
$R^3$ is a group represented by

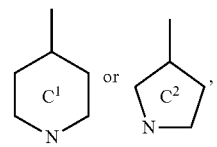

wherein
ring C¹ is an optionally substituted 6-membered nitrogen-containing aromatic heterocycle containing at least one nitrogen atom; and
ring C² is an optionally substituted 5-membered nitrogen-containing aromatic heterocycle containing at least one nitrogen atom,
(preferably pyridyl, pyrimidinyl, pyridazinyl or oxazolyl), each of which is optionally substituted by 1 to 3 halogen atoms (e.g., a fluorine atom);
ring A is a piperidine ring having no substituent other than R¹, R²—O— and —C(═O)-ring B; and
ring B is

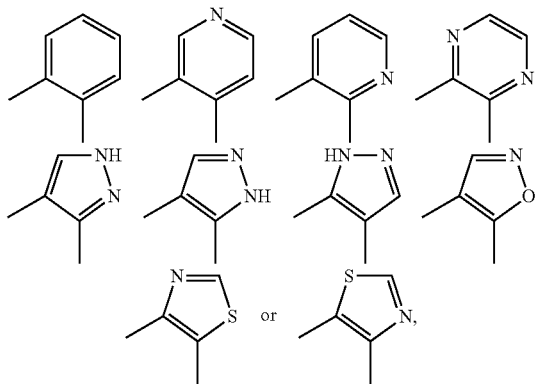

each of which is, in addition to R³ and —C(═O)-ring A, optionally substituted by 1 to 3 substituents selected from
(1) a halogen atom (e.g., a fluorine atom, a chlorine atom),
(2) a C₁₋₆ alkyl group (e.g., methyl, tert-butyl) optionally substituted by 1 to 3 halogen atoms (e.g., a fluorine atom),
(3) a C₁₋₆ alkoxy group (e.g., methoxy), and
(4) a C₁₋₆ alkylenedioxy group (e.g., methylenedioxyl), or a salt thereof.

[Compound D1]
Compound (I) wherein
R¹ is a C₁₋₆ alkyl group (preferably a C₁₋₃ alkyl group (e.g., methyl, ethyl, propyl, isopropyl)) optionally substituted by 1 to 3 substituents selected from
(1) a C₆₋₁₄ aryl group (e.g., phenyl) optionally substituted by 1 to 3 substituents selected from
    (a) a halogen atom (e.g., a fluorine atom),
    (b) a cyano group, and
    (c) a C₁₋₆ alkoxy group (e.g., methoxy) optionally substituted by 1 to 3 halogen atoms (e.g., a fluorine atom),
(2) a 5- or 6-membered monocyclic aromatic heterocyclic group (e.g., pyridyl) optionally substituted by 1 to 3 substituents selected from
    (a) a halogen atom (e.g., a fluorine atom),
    (b) a cyano group, and
    (c) a C₁₋₆ alkoxy group (e.g., methoxy) optionally substituted by 1 to 3 halogen atoms (e.g., a fluorine atom), and
(3) a 3- to 8-membered monocyclic non-aromatic heterocyclic group (e.g., thiazolinyl) optionally substituted by 1 to 3 substituents selected from
    (a) a halogen atom (e.g., a fluorine atom),
    (b) a cyano group, and
    (c) a C₁₋₆ alkoxy group (e.g., methoxy) optionally substituted by 1 to 3 halogen atoms (e.g., a fluorine atom);
R² is a hydrogen atom or a C₁₋₆ alkyl group (preferably a C₁₋₃ alkyl group (e.g., methyl)) (preferably a hydrogen atom);
R³ is a 5- or 6-membered nitrogen-containing aromatic heterocyclic group (preferably pyridyl, pyrimidinyl, pyridazinyl or oxazolyl) optionally substituted by 1 to 3 halogen atoms (e.g., a fluorine atom);
ring A is a piperidine ring having no substituent other than R¹, R²—O— and —C(═O)-ring B, or an oxa-9-azabicyclo [3.3.1]nonane ring having no substituent other than R¹, R²—O— and —C(═O)-ring B; and
ring B is a 5- or 6-membered aromatic ring (preferably benzene, thiazole, isoxazole, pyrazole, pyridine or pyrazine) (X and Y are independently a carbon atom or a nitrogen atom), which is, in addition to R³ and —C(═O)-ring A, optionally substituted by 1 to 3 substituents selected from
(1) a halogen atom (e.g., a fluorine atom, a chlorine atom),
(2) a C₁₋₆ alkyl group (e.g., methyl, tert-butyl) optionally substituted by 1 to 3 halogen atoms (e.g., a fluorine atom),
(3) a C₁₋₆ alkoxy group (e.g., methoxy), and
(4) a C₁₋₆ alkylenedioxy group (e.g., methylenedioxy), or a salt thereof.

[Compound D2]
Compound (I) wherein
R¹ is a C₁₋₆ alkyl group (preferably a C₁₋₃ alkyl group (e.g., methyl, ethyl, propyl, isopropyl)) optionally substituted by 1 to 3 substituents selected from
(1) a C₆₋₁₄ aryl group (e.g., phenyl) optionally substituted by 1 to 3 substituents selected from
    (a) a halogen atom (e.g., a fluorine atom),
    (b) a cyano group, and
    (c) a C₁₋₆ alkoxy group (e.g., methoxy) optionally substituted by 1 to 3 halogen atoms (e.g., a fluorine atom),
(2) a 5- or 6-membered monocyclic aromatic heterocyclic group (e.g., pyridyl), and
(3) a 3- to 8-membered monocyclic non-aromatic heterocyclic group (e.g., thiazolinyl);
R² is a hydrogen atom or a C₁₋₆ alkyl group (preferably a C₁₋₃ alkyl group (e.g., methyl)) (preferably a hydrogen atom);
R³ is a 5- or 6-membered nitrogen-containing aromatic heterocyclic group (preferably pyridyl, pyrimidinyl, pyridazinyl or oxazolyl) optionally substituted by 1 to 3 halogen atoms (e.g., a fluorine atom);
ring A is a piperidine ring having no substituent other than R¹, R²—O— and —C(═O)-ring B; and
ring B is a 5- or 6-membered aromatic ring (preferably benzene, thiazole, isoxazole, pyrazole, pyridine or pyrazine) (X and Y are independently a carbon atom or a nitrogen atom), which is, in addition to R³ and —C(═O)-ring A, optionally substituted by 1 to 3 substituents selected from
(1) a halogen atom (e.g., a fluorine atom, a chlorine atom),
(2) a C₁₋₆ alkyl group (e.g., methyl, tert-butyl) optionally substituted by 1 to 3 halogen atoms (e.g., a fluorine atom),
(3) a C₁₋₆ alkoxy group (e.g., methoxy) and
(4) a C₁₋₆ alkylenedioxy group (e.g., methylenedioxy), or a salt thereof.

[Compound E1]
Compound (I) wherein
$R^1$ is a $C_{1-6}$ alkyl group (preferably a $C_{1-3}$ alkyl group (e.g., methyl, ethyl, propyl, isopropyl)) optionally substituted by 1 to 3 substituents selected from
(1) a $C_{6-14}$ aryl group (e.g., phenyl) optionally substituted by 1 to 3 substituents selected from
  (a) a halogen atom (e.g., a fluorine atom),
  (b) a cyano group, and
  (c) a $C_{1-6}$ alkoxy group (e.g., methoxy) optionally substituted by 1 to 3 halogen atoms (e.g., a fluorine atom),
(2) a 5- or 6-membered monocyclic aromatic heterocyclic group (e.g., pyridyl) optionally substituted by 1 to 3 substituents selected from
  (a) a halogen atom (e.g., a fluorine atom),
  (b) a cyano group, and
  (c) a $C_{1-6}$ alkoxy group (e.g., methoxy) optionally substituted by 1 to 3 halogen atoms (e.g., a fluorine atom), and
(3) a 3- to 8-membered monocyclic non-aromatic heterocyclic group (e.g., thiazolinyl) optionally substituted by 1 to 3 substituents selected from
  (a) a halogen atom (e.g., a fluorine atom),
  (b) a cyano group, and
  (c) a $C_{1-6}$ alkoxy group (e.g., methoxy) optionally substituted by 1 to 3 halogen atoms (e.g., a fluorine atom);
$R^2$ is a hydrogen atom or a $C_{2-6}$ alkyl group (preferably a $C_{1-3}$ alkyl group (e.g., methyl)) (preferably a hydrogen atom);
$R^3$ is a 5- or 6-membered nitrogen-containing aromatic heterocyclic group (preferably pyridyl, pyrimidinyl, pyridazinyl or oxazolyl) optionally substituted by 1 to 3 halogen atoms (e.g., a fluorine atom);
ring A is a piperidine ring having no substituent other than $R^1$, $R^2$—O— and —C(=O)-ring B, or an oxa-9-azabicyclo[3.3.1]nonane ring having no substituent other than $R^1$, $R^2$—O— and —C(=O)-ring B; and
ring B is benzene, thiazole, isoxazole, pyrazole, pyridine or pyrazine (X and Y are independently a carbon atom or a nitrogen atom), each of which is, in addition to $R^3$ and —C(=O)-ring A, optionally substituted by 1 to 3 substituents selected from
(1) a halogen atom (e.g., a fluorine atom, a chlorine atom),
(2) a $C_{1-6}$ alkyl group (e.g., methyl, tert-butyl) optionally substituted by 1 to 3 halogen atoms (e.g., a fluorine atom),
(3) a $C_{1-6}$ alkoxy group (e.g., methoxy), and
(4) a $C_{1-6}$ alkylenedioxy group (e.g., methylenedioxy), or a salt thereof.

[Compound E2]
Compound (I) wherein
$R^1$ is a $C_{1-6}$ alkyl group (preferably a $C_{1-3}$ alkyl group (e.g., methyl, ethyl, propyl, isopropyl)) optionally substituted by 1 to 3 substituents selected from
(1) a $C_{6-14}$ aryl group (e.g., phenyl) optionally substituted by 1 to 3 substituents selected from
  (a) a halogen atom (e.g., a fluorine atom),
  (b) a cyano group, and
  (c) a $C_{1-6}$ alkoxy group (e.g., methoxy) optionally substituted by 1 to 3 halogen atoms (e.g., a fluorine atom),
(2) a 5- or 6-membered monocyclic aromatic heterocyclic group (e.g., pyridyl), and
(3) a 3- to 8-membered monocyclic non-aromatic heterocyclic group (e.g., thiazolinyl);
$R^2$ is a hydrogen atom or a $C_{1-6}$ alkyl group (preferably a $C_{1-3}$ alkyl group (e.g., methyl)) (preferably a hydrogen atom);
$R^3$ is a 5- or 6-membered nitrogen-containing aromatic heterocyclic group (preferably pyridyl, pyrimidinyl, pyridazinyl or oxazolyl) optionally substituted by 1 to 3 halogen atoms (e.g., a fluorine atom);
ring A is a piperidine ring having no substituent other than $R^1$, $R^2$—O— and —C(=O)-ring B; and
ring B is benzene, thiazole, isoxazole, pyrazole, pyridine or pyrazine (X and Y are independently a carbon atom or a nitrogen atom), each of which is, in addition to $R^3$ and —C(=O)-ring A, optionally substituted by 1 to 3 substituents selected from
(1) a halogen atom (e.g., a fluorine atom, a chlorine atom),
(2) a $C_{1-6}$ alkyl group (e.g., methyl, tert-butyl) optionally substituted by 1 to 3 halogen atoms (e.g., a fluorine atom),
(3) a $C_{1-6}$ alkoxy group (e.g., methoxy), and
(4) a $C_{1-6}$ alkylenedioxy group (e.g., methylenedioxy), or a salt thereof.

[Compound E3]
Compound (I) wherein
$R^1$ is a $C_{1-6}$ alkyl group (preferably a $C_{1-3}$ alkyl group (e.g., methyl, ethyl, propyl, isopropyl)) optionally substituted by 1 to 3 substituents selected from
(1) a $C_{6-14}$ aryl group (e.g., phenyl) optionally substituted by 1 to 3 substituents selected from
  (a) a halogen atom (e.g., a fluorine atom),
  (b) a cyano group, and
  (c) a $C_{1-6}$ alkoxy group (e.g., methoxy) optionally substituted by 1 to 3 halogen atoms (e.g., a fluorine atom),
(2) a 5- or 6-membered monocyclic aromatic heterocyclic group (e.g., pyridyl), and
(3) a 3- to 8-membered monocyclic non-aromatic heterocyclic group (e.g., thiazolinyl);
$R^2$ is a hydrogen atom or a $C_{1-6}$ alkyl group (preferably a $C_{1-3}$ alkyl group (e.g., methyl)) (preferably a hydrogen atom);
$R^3$ is a 5- or 6-membered nitrogen-containing aromatic heterocyclic group (preferably pyridyl, pyrimidinyl, pyridazinyl or oxazolyl) optionally substituted by 1 to 3 halogen atoms (e.g., a fluorine atom);
ring A is a piperidine ring having no substituent other than $R^1$, $R^2$—O— and —C(=O)-ring B; and
ring B is

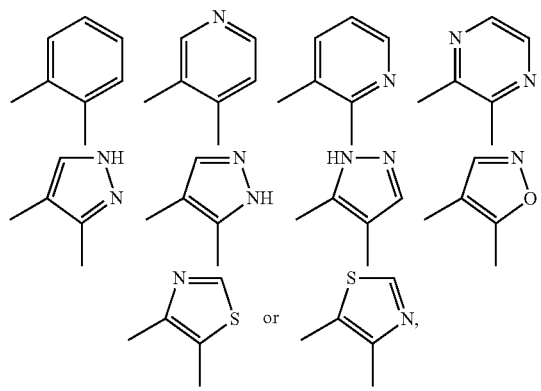

each of which is, in addition to $R^3$ and —C(=O)-ring A, optionally substituted by 1 to 3 substituents selected from (1) a halogen atom (e.g., a fluorine atom, a chlorine atom),
(2) a C$_{1-6}$ alkyl group (e.g., methyl, tert-butyl) optionally substituted by 1 to 3 halogen atoms (e.g., a fluorine atom),
(3) a C$_{1-6}$ alkoxy group (e.g., methoxy), and
(4) a C$_{1-6}$ alkylenedioxy group (e.g., methylenedioxy), or a salt thereof.

[Compound F1]
Compound (I) wherein
R$^1$ is a C$_{1-6}$ alkyl group (preferably a C$_{1-3}$ alkyl group (e.g., methyl, ethyl, propyl, isopropyl)) optionally substituted by 1 to 3 substituents selected from
  (1) a C$_{6-14}$ aryl group (e.g., phenyl) optionally substituted by 1 to 3 substituents selected from
    (a) a halogen atom (e.g., a fluorine atom),
    (b) a cyano group, and
    (c) a C$_{1-6}$ alkoxy group (e.g., methoxy) optionally substituted by 1 to 3 halogen atoms (e.g., a fluorine atom),
  (2) a 5- or 6-membered monocyclic aromatic heterocyclic group (e.g., pyridyl) optionally substituted by 1 to 3 substituents selected from
    (a) a halogen atom (e.g., a fluorine atom),
    (b) a cyano group, and
    (c) a C$_{1-6}$ alkoxy group (e.g., methoxy) optionally substituted by 1 to 3 halogen atoms (e.g., a fluorine atom), and
  (3) a 3- to 8-membered monocyclic non-aromatic heterocyclic group (e.g., thiazolinyl) optionally substituted by 1 to 3 substituents selected from
    (a) a halogen atom (e.g., a fluorine atom),
    (b) a cyano group, and
    (c) a C$_{1-6}$ alkoxy group (e.g., methoxy) optionally substituted by 1 to 3 halogen atoms (e.g., a fluorine atom);
R$^2$ is a hydrogen atom or a C$_{1-6}$ alkyl group (preferably a C$_{1-3}$ alkyl group (e.g., methyl)) (preferably a hydrogen atom);
R$^3$ is a group represented by

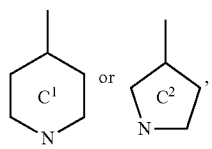

wherein
ring C$^1$ is an optionally substituted 6-membered nitrogen-containing aromatic heterocycle containing at least one nitrogen atom; and
ring C$^2$ is an optionally substituted 5-membered nitrogen-containing aromatic heterocycle containing at least one nitrogen atom,
(preferably pyridyl, pyrimidinyl, pyridazinyl or oxazolyl), each of which is optionally substituted by 1 to 3 halogen atoms (e.g., a fluorine atom);
ring A is a piperidine ring having no substituent other than R$^1$, R$^2$—O— and —C(=O)-ring B, or an oxa-9-azabicyclo[3.3.1]nonane ring having no substituent other than R$^1$, R$^2$—O— and —C(=O)-ring B; and
ring B is a 5- or 6-membered aromatic ring (preferably benzene, thiazole, isoxazole, pyrazole, pyridine or pyrazine) (X and Y are independently a carbon atom or a nitrogen atom), which is, in addition to R$^3$ and —C(=O)-ring A, optionally substituted by 1 to 3 substituents selected from
(1) a halogen atom (e.g., a fluorine atom, a chlorine atom),
(2) a C$_{1-6}$ alkyl group (e.g., methyl, tert-butyl) optionally substituted by 1 to 3 halogen atoms (e.g., a fluorine atom),
(3) a C$_{1-6}$ alkoxy group (e.g., methoxy), and
(4) a C$_{1-6}$ alkylenedioxy group (e.g., methylenedioxy), or a salt thereof.

[Compound F2]
Compound (I) wherein
R$^1$ is a C$_{1-6}$ alkyl group (preferably a C$_{1-3}$ alkyl group (e.g., methyl, ethyl, propyl, isopropyl)) optionally substituted by 1 to 3 substituents selected from
  (1) a C$_{6-14}$ aryl group (e.g., phenyl) optionally substituted by 1 to 3 substituents selected from
    (a) a halogen atom (e.g., a fluorine atom),
    (b) a cyano group, and
    (c) a C$_{1-6}$ alkoxy group (e.g., methoxy) optionally substituted by 1 to 3 halogen atoms (e.g., a fluorine atom),
  (2) a 5- or 6-membered monocyclic aromatic heterocyclic group (e.g., pyridyl), and
  (3) a 3- to 8-membered monocyclic non-aromatic heterocyclic group (e.g., thiazolinyl);
R$^2$ is a hydrogen atom or a C$_{1-6}$ alkyl group (preferably a C$_{1-3}$ alkyl group (e.g., methyl)) (preferably a hydrogen atom);
R$^3$ is a group represented by

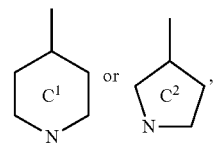

wherein
ring C$^1$ is an optionally substituted 6-membered nitrogen-containing aromatic heterocycle containing at least one nitrogen atom; and
ring C$^2$ is an optionally substituted 5-membered nitrogen-containing aromatic heterocycle containing at least one nitrogen atom,
(preferably pyridyl, pyrimidinyl, pyridazinyl or oxazolyl), each of which is optionally substituted by 1 to 3 halogen atoms (e.g., a fluorine atom);
ring A is a piperidine ring having no substituent other than R$^1$, R$^2$—O— and —C(=O)-ring B; and
ring B is a 5- or 6-membered aromatic ring (preferably benzene, thiazole, isoxazole, pyrazole, pyridine or pyrazine) (X and Y are independently a carbon atom or a nitrogen atom), which is, in addition to R$^3$ and —C(=O)-ring A, optionally substituted by 1 to 3 substituents selected from
(1) a halogen atom (e.g., a fluorine atom, a chlorine atom),
(2) a C$_{1-6}$ alkyl group (e.g., methyl, tert-butyl) optionally substituted by 1 to 3 halogen atoms (e.g., a fluorine atom),
(3) a C$_{1-6}$ alkoxy group (e.g., methoxy), and
(4) a C$_{1-6}$ alkylenedioxy group (e.g., methylenedioxy), or a salt thereof.

[Compound G1]
Compound (I) wherein
R$^1$ is a C$_{1-6}$ alkyl group (preferably a C$_{1-3}$ alkyl group (e.g., methyl, ethyl, propyl, isopropyl)) optionally substituted by 1 to 3 substituents selected from (1) a $C_{6-14}$ aryl group (e.g., phenyl) optionally substituted by 1 to 3 substituents selected from
  (a) a halogen atom (e.g., a fluorine atom),
  (b) a cyano group, and
  (c) a $C_{1-6}$ alkoxy group (e.g., methoxy) optionally substituted by 1 to 3 halogen atoms (e.g., a fluorine atom),
(2) a 5- or 6-membered monocyclic aromatic heterocyclic group (e.g., pyridyl) optionally substituted by 1 to 3 substituents selected from
  (a) a halogen atom (e.g., a fluorine atom),
  (b) a cyano group, and
  (c) a $C_{1-6}$ alkoxy group (e.g., methoxy) optionally substituted by 1 to 3 halogen atoms (e.g., a fluorine atom), and
(3) a 3- to 8-membered monocyclic non-aromatic heterocyclic group (e.g., thiazolinyl) optionally substituted by 1 to 3 substituents selected from
  (a) a halogen atom (e.g., a fluorine atom),
  (b) a cyano group, and
  (c) a $C_{1-6}$ alkoxy group (e.g., methoxy) optionally substituted by 1 to 3 halogen atoms (e.g., a fluorine atom);

$R^2$ is a hydrogen atom or a $C_{1-6}$ alkyl group (preferably a $C_{1-3}$ alkyl group (e.g., methyl)) (preferably a hydrogen atom);

$R^3$ is a group represented by

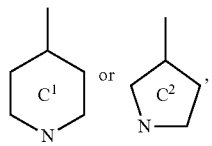

wherein ring $C^1$ is an optionally substituted 6-membered nitrogen-containing aromatic heterocycle containing at least one nitrogen atom; and ring $C^2$ is an optionally substituted 5-membered nitrogen-containing aromatic heterocycle containing at least one nitrogen atom, (preferably pyridyl, pyrimidinyl, pyridazinyl or oxazolyl), each of which is optionally substituted by 1 to 3 halogen atoms (e.g., a fluorine atom);

ring A is a piperidine ring having no substituent other than $R^1$, $R^2$—O— and —C(=O)-ring B, or an oxa-9-azabicyclo[3.3.1]nonane ring having no substituent other than $R^1$, $R^2$—O— and —C(=O)-ring B; and ring B is benzene, thiazole, isoxazole, pyrazole, pyridine or pyrazine (X and Y are independently a carbon atom or a nitrogen atom), each of which is, in addition to $R^3$ and —C(=O)-ring A, optionally substituted by 1 to 3 substituents selected from
  (1) a halogen atom (e.g., a fluorine atom, a chlorine atom),
  (2) a $C_{1-6}$ alkyl group (e.g., methyl, tert-butyl) optionally substituted by 1 to 3 halogen atoms (e.g., a fluorine atom),
  (3) a $C_{1-6}$ alkoxy group (e.g., methoxy), and
  (4) a $C_{1-6}$ alkylenedioxy group (e.g., methylenedioxy),
or a salt thereof.

[Compound G2]

Compound (I) wherein $R^1$ is a $C_{1-6}$ alkyl group (preferably a $C_{1-3}$ alkyl group (e.g., methyl, ethyl, propyl, isopropyl)) optionally substituted by 1 to 3 substituents selected from (1) a $C_{6-14}$ aryl group (e.g., phenyl) optionally substituted by 1 to 3 substituents selected from
  (a) a halogen atom (e.g., a fluorine atom),
  (b) a cyano group, and
  (c) a $C_{1-6}$ alkoxy group (e.g., methoxy) optionally substituted by 1 to 3 halogen atoms (e.g., a fluorine atom),
(2) a 5- or 6-membered monocyclic aromatic heterocyclic group (e.g., pyridyl), and
(3) a 3- to 8-membered monocyclic non-aromatic heterocyclic group (e.g., thiazolinyl);

$R^2$ is a hydrogen atom or a $C_{1-6}$ alkyl group (preferably a $C_{1-3}$ alkyl group (e.g., methyl)) (preferably a hydrogen atom);

$R^3$ is a group represented by

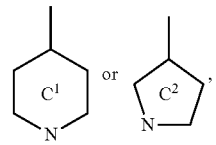

wherein ring $C^1$ is an optionally substituted 6-membered nitrogen-containing aromatic heterocycle containing at least one nitrogen atom; and ring $C^2$ is an optionally substituted 5-membered nitrogen-containing aromatic heterocycle containing at least one nitrogen atom, (preferably pyridyl, pyrimidinyl, pyridazinyl or oxazolyl), each of which is optionally substituted by 1 to 3 halogen atoms (e.g., a fluorine atom);

ring A is a piperidine ring having no substituent other than $R^1$, $R^2$—O— and —C(=O)-ring B; and ring B is

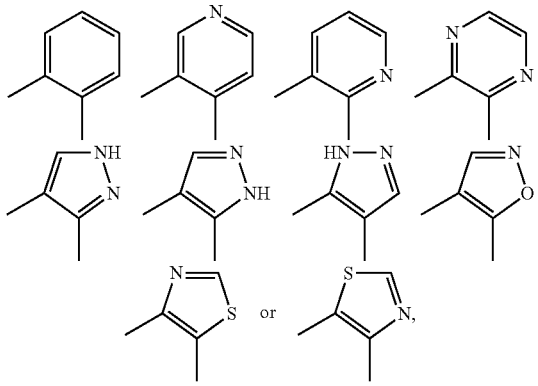

each of which is, in addition to $R^3$ and —C(=O)-ring A, optionally substituted by 1 to 3 substituents selected from
  (1) a halogen atom (e.g., a fluorine atom, a chlorine atom),
  (2) a $C_{1-6}$ alkyl group (e.g., methyl, tert-butyl) optionally substituted by 1 to 3 halogen atoms (e.g., a fluorine atom),
  (3) a $C_{1-6}$ alkoxy group (e.g., methoxy), and
  (4) a $C_{1-6}$ alkylenedioxy group (e.g., methylenedioxy),
or a salt thereof.

[Compound G3]
Compound (I) wherein
$R^1$ is a $C_{1-6}$ alkyl group (preferably a $C_{1-3}$ alkyl group (e.g., methyl, ethyl, propyl, isopropyl)) optionally substituted by 1 to 3 substituents selected from
(1) a $C_{6-14}$ aryl group (e.g., phenyl) optionally substituted by 1 to 3 substituents selected from
(a) a halogen atom (e.g., a fluorine atom),
(b) a cyano group, and
(c) a $C_{1-6}$ alkoxy group (e.g., methoxy) optionally substituted by 1 to 3 halogen atoms (e.g., a fluorine atom),
(2) a 5- or 6-membered monocyclic aromatic heterocyclic group (e.g., pyridyl), and
(3) a 3- to 8-membered monocyclic non-aromatic heterocyclic group (e.g., thiazolinyl);
$R^2$ is a hydrogen atom;
$R^3$ is a group represented by

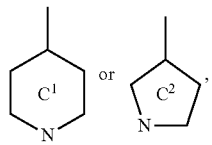

wherein
ring $C^1$ is an optionally substituted 6-membered nitrogen-containing aromatic heterocycle containing at least one nitrogen atom; and
ring $C^2$ is an optionally substituted 5-membered nitrogen-containing aromatic heterocycle containing at least one nitrogen atom,
(preferably pyridyl, pyrimidinyl, pyridazinyl or oxazolyl), each of which is optionally substituted by 1 to 3 halogen atoms (e.g., a fluorine atom);
ring A is a piperidine ring having no substituent other than $R^1$, $R^2$—O— and —C(=O)-ring B; and
ring B is

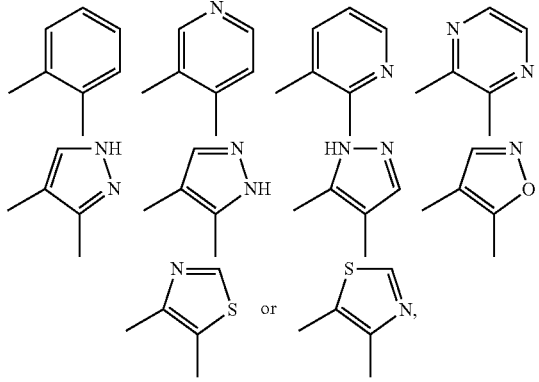

each of which is, in addition to $R^3$ and —C(=O)-ring A, optionally substituted by 1 to 3 substituents selected from
(1) a halogen atom (e.g., a fluorine atom, a chlorine atom),
(2) a $C_{1-6}$ alkyl group (e.g., methyl, tert-butyl) optionally substituted by 1 to 3 halogen atoms (e.g., a fluorine atom),
(3) a $C_{1-6}$ alkoxy group (e.g., methoxy), and
(4) a $C_{1-6}$ alkylenedioxy group (e.g., methylenedioxy), or a salt thereof.

[Compound G4]
Compound (I) selected from
(4-benzyl-4-hydroxypiperidin-1-yl)(2,4'-bipyridin-3-yl)methanone,
2,4'-bipyridin-3-yl(4-(4-fluorobenzyl)-4-hydroxypiperidin-1-yl)methanone,
2,4'-bipyridin-3-yl(4-(2,4-difluorobenzyl)-4-hydroxypiperidin-1-yl)methanone, and
(4-(4-fluorobenzyl)-4-hydroxypiperidin-1-yl)(2-(pyrimidin-4-yl)pyridin-3-yl)methanone
or a salt thereof.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic, acid and the like. Preferable examples of the salt with basic amino acid include salts with arginine, lysine, ornithine and the like. Preferable examples of the salt with acidic amino acid include salts with aspartic acid, glutamic acid and the like.

Of these, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The compound of the present invention and the starting compounds can be produced by a method known per se, for example, by method shown in the following scheme and the like. In the following, the "room temperature" generally means 0-40° C. and, unless otherwise specified, each symbol in the chemical formulas described in the schemes is as defined above. In the formulas, each compound includes salts, and examples of such salt include those similar to the salts of the compound of the present invention and the like. The compound obtained in each step can be used directly as the reaction mixture or as a crude product for the next reaction. It can also be isolated from a reaction mixture by a conventional method, and can be easily purified by a separation means such as recrystallization, distillation, chromatography and the like. When the compound in the formula is commercially available, a commercially available product can also be used directly. When each ring in the formula (1) has a substituent, the corresponding precursor also has a similar substituent.

When the starting compound has an amino group, a carboxyl group, a hydroxy group or a heterocyclic group, these groups may be protected by a protecting group generally used in peptide chemistry and the like. By removing the protecting group as necessary after the reaction, the objective compound can be obtained. The protection and deprotection can be performed according to a method known per se, for example, the method described in "Protective Groups in Organic Synthesis, 3rd Ed", John Wiley and Sons, Inc. (1999) (Theodora W. Greene, Peter G. M. Wuts). In the following schemes, $P^1$ is a carboxy-protecting group, and $P^2$ is a protecting group for the nitrogen atom of amine or amide, and the protecting group known per se can be used. For example, $P^1$ is preferably a benzyl group, a methyl group, an ethyl group, a tert-butyl group or the like, and $P^2$ is preferably a tert-butoxycarbonyl group, a benzyloxycarbonyl group, a benzyl group or the like.

Examples of the "leaving group" for $LG^1$-$LG^4$ include a halogen atom (e.g., a chlorine atom, a bromine atom, an iodine atom etc.), $C_{1-6}$ alkylsulfonyloxy optionally substituted by halogen atom(s) (e.g., a chlorine atom, a bromine atom, an iodine atom etc.) (e.g., methanesulfonyloxy, ethanesulfonyloxy, trifluoromethanesulfonyloxy etc.), $C_{6-10}$ arylsulfonyloxy optionally substituted by $C_{1-6}$ alkyl group(s) (e.g., methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl etc.) (e.g., benzenesulfonyloxy, p-toluenesulfonyloxy etc.), $C_{1-6}$ alkylsulfonyl (e.g., methanesulfonyl, ethanesulfonyl etc.) and the like. In addition, a substituent capable of converting to a leaving group is encompassed in $LG^1$-$LG^4$, and it can be converted to a leaving group by a reaction known per se in a desired step. For example, when $LG^1$-$LG^4$ is a methylthio group, it is converted to a methanesulfonyl group by oxidation reaction.

The following each step can be performed without solvent, or by dissolving or suspending starting material compound in a suitable solvent prior to the reaction. In this case, solvent may be used alone, or two or more kinds of these solvents may be mixed in an appropriate ratio and used. Specific examples of the solvent used for the production method of the compound of the present invention include the followings.
alcohols: methanol, ethanol, 1-propanol, 2-propanol, tert-butyl alcohol, 2-methoxyethanol etc.
ethers: diethyl ether, diisopropyl ether, diphenyl ether, tetrahydrofuran, 1,4-dioxane, 1,2-dimethoxyethane etc.
aromatic hydrocarbons: benzene, chlorobenzene, toluene, xylene etc.
saturated hydrocarbons: cyclohexane, hexane etc.
amides: N,N-dimethylformamide, N,N-dimethylacetamide, hexamethylphosphoric triamide etc. halogenated hydrocarbons: dichloromethane, chloroform, carbon tetrachloride, 1,2-dichloroethane etc.
nitriles: acetonitrile, propionitrile etc.
sulfoxides: dimethylsulfoxide etc.
aromatic organic bases: pyridine, lutidine etc.
acid anhydrides: acetic anhydride etc.
organic acids: formic acid, acetic acid, propionic acid, trifluoroacetic acid, methanesulfonic acid etc.
inorganic acids: hydrochloric acid, sulfuric acid etc.
esters: methyl acetate, ethyl acetate, butyl acetate etc.
ketones: acetone, methylethylketone etc.

Specific examples of the base or acid scavenger used for the production method of the compound of the present invention include the followings.
inorganic bases: sodium hydroxide, potassium hydroxide, magnesium hydroxide etc.
basic salts: sodium carbonate, potassium carbonate, cesium carbonate, calcium carbonate, sodium hydrogen carbonate etc.
organic bases: triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole etc.
metal alkoxides: sodium methoxide, sodium ethoxide, potassium tert-butoxide etc.
alkali metal hydrides: sodium hydride, potassium hydride etc.
metal amides: sodium amide, lithiumdiisopropylamide, lithiumhexamethyldisilazide etc.
organic lithium reagents: methyllithium, n-butyllithium, sec-butyllithium, tert-butyllithium etc.

Specific examples of the acid or acid catalyst used for the production method of the compound of the present invention include the followings.
inorganic acids: hydrochloric acid, sulfuric acid, nitric acid, hydrobromic acid, phosphoric acid etc.
organic acids: acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid etc.
Lewis acid: boron trifluoride ether complex, zinc iodide, anhydrous aluminum chloride, anhydrous zinc chloride, anhydrous iron chloride etc.

Compound (I) can be synthesized, for example, according to Production Method A, Production Method B or the like explained below.

The symbols in each scheme in the production method are as defined above, unless otherwise specified. In each reaction in Production Method A and B, $R^a$ is a hydrogen atom or an optionally substituted $C_{1-6}$ alkyl group (e.g., methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl etc.), or two $R^a$ in combination optionally form a ring such as 4,4,5,5-tetramethyl-1,3,2-dioxaborolane and the like.

[Production Method A]

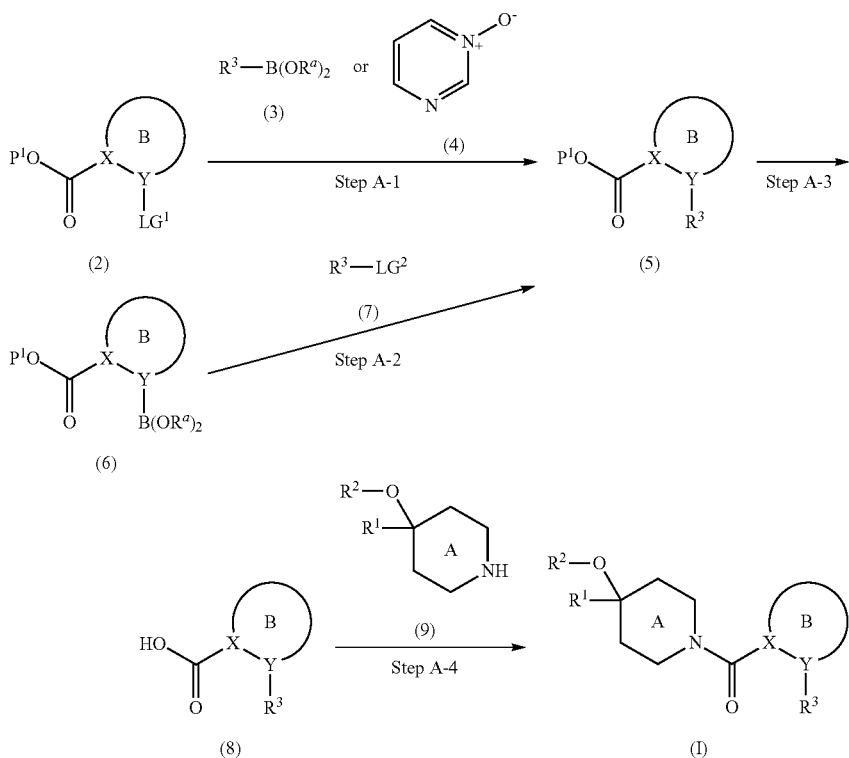

wherein each symbol is as defined above.

The compound of the present invention can be produced by a sequence of reaction steps of Step A-1 to Step A-4.

(Step A-1)

Compound (5) can be produced by reacting compound (2) with compound (3) or compound (4) ($R^3$=4-pyrimidinyl). The reaction is carried out in the presence of a metal catalyst. The metal catalyst is preferably a palladium compound [e.g., palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), a complex of palladium(II) acetate and 1,1'-bis(diphenylphosphino)ferrocene, etc.]. The amount of the metal catalyst to be used is about 0.000001-1.0 mol per 1 mol of compound (2). The metal catalyst can be used together with a phosphine ligand. The amount of the phosphine ligand to be used is about 0.01-mol per 1 mol of compound (2). Examples of the phosphine ligand include triphenylphosphine, 4,5-bis(diphenylphosphino)-9,9-dimethylxanthene, tri-tert-butylphosphine and the like. In addition, a salt such as tri-tert-butylphosphine tetrafluoroborate can be used. The reaction is generally carried out in the presence of a base. Examples of the base include inorganic bases, basic salts and the like. When desired, the reaction may be carried out by adding an additive such as copper(I) cyanide, copper(I) bromide and the like. The amount of compound (3) or compound (4) to be used is about 0.8-10 mol per 1 mol of compound (2). The amount of the base to be used is about 1-20 mol per 1 mol of compound (2). The amount of the additive to be used is about 0.000001-5.0 mol per 1 mol of compound (2). When a metal catalyst unstable to oxygen is used for the reaction, the reaction is preferably carried out in a stream of an inactive gas such as argon gas, nitrogen gas and the like. This reaction is advantageously carried out in a solvent inert to the reaction. While the solvent is not particularly limited as long as the reaction proceeds, preferable examples thereof include alcohols, ethers, aromatic hydrocarbons, saturated hydrocarbons, amides, halogenated hydrocarbons, nitriles, esters, water, mixed solvents thereof and the like. While the reaction time varies depending on the reagent or solvent to be used, it is generally 1 min-200 hr. The reaction temperature is preferably 0-150° C. In addition, the reaction can be carried out with irradiation of microwave in order to promote the reaction., (Step A-2)

Compound (5) can also be produced by reacting compound (6) with compound (7). The reaction is carried out in the same manner as in Step A-1.

When desired, compound (5) produced in Step A-1 or Step A-2 can be subjected to a reduction step. For example, when compound (5) contains N-oxido or a halogen atom, it is removed by a reduction reaction known per se using palladium carbon and the like.

(Step A-3)

Compound (8) can be produced by removing the protecting group $P^1$ of compound (5). The removal of the protecting group can be carried out according to a method known per se, for example, the method described in "Protective Groups in Organic Synthesis, 3rd Ed", John Wiley and Sons, Inc. (1999) (Theodora W. Greene, Peter G. M. Wuts), or the like.

Compound (8) can also be produced according to a method known per se, or a method analogous thereto.

(Step A-4)

Compound (I) can be produced by reacting carboxylic acid (8) or a reactive derivative thereof with compound (9). Examples of the reactive derivative of the carboxylic acid include acid halides such as acid chlorides, acid bromides and the like; acid amides with pyrazole, imidazole, benzotriazole and the like; mixed acid anhydrides with as acetic acid, propionic acid, butyric acid and the like; acid azides; activated esters such as diethoxyphosphate ester, diphenoxyphosphate ester, p-nitrophenyl ester, 2,4-dinitrophenyl ester, cyanomethyl ester, pentachlorophenyl ester, ester with N-hydroxysuccinimide, ester with N-hydroxyphthalimide, ester with 1-hydroxybenzotriazole, ester with 6-chloro-1-hydroxybenzotriazole, ester with 1-hydroxy-1H-2-pyridone, and the like; activated thioesters such as 2-pyridyl thioester, 2-benzothiazolyl thioester and the like, and the like. Compound (I) can also be produced by directly reacting carboxylic acid (8) with compound (9) in the presence of a suitable condensing agent, instead of using the reactive derivative. Examples of the condensing agent include N,N'-disubstituted carbodiimides such as N,N'-dicyclohexylcarbodiimide, 1-ethyl-3-(3-dimethylaminopropyl)carbodiimide (WSC) hydrochloride and the like; azolides such as N,N'-carbonyldiimidazole and the like; dehydrating agents such as N-ethoxycarbonyl-2-ethoxy-1,2-dihydroquinoline, phosphorus oxychloride, alkoxyacetylene and the like; 2-halogenopyridiniums such as 2-chloromethylpyridinium iodide, 2-fluoro-1-methylpyridinium iodide and the like; phosphorylcyanides such as diethylphosphorylcyanide and the like; 2-(7-azabenzotriazol-1-yl)-1,1,3,3-tetramethyluronium hexafluorophosphate (HATU), 0-(7-azabenzotriazol-1-yl)-N,N,N',N'-tetramethyluronium tetrafluoroborate (TATU) and the like. When a condensing agent is used, the reaction is considered to progress via a reactive derivative of carboxylic acid (8). The amount of carboxylic acid (8) or a reactive derivative thereof to be used is generally about 0.8-5 mol per 1 mol of compound (9). This reaction is advantageously carried out in a solvent inert to the reaction. While the solvent is not particularly limited as long as the reaction proceeds, preferable examples thereof include ethers, aromatic hydrocarbons, saturated hydrocarbons, amides, halogenated hydrocarbons, nitriles, sulfoxides, aromatic organic bases, mixed solvents thereof. The reaction can be carried out in the presence of a basic salt, an organic bases or the like in order to promote the reaction. In addition, when an acidic substance is released due the reaction, a basic salt, an organic base and the like can be used in order to remove it from the reaction system. While the reaction time varies depending on the reagent or solvent to be used, it is generally 10 min-72 hr. The reaction temperature is preferably 0-100° C.

[Production Method B]

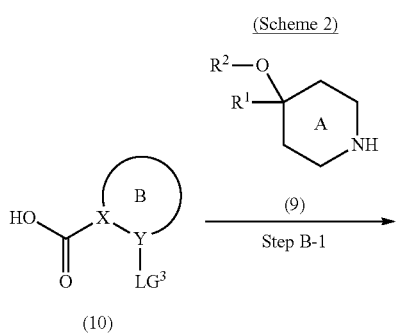

(Scheme 2)

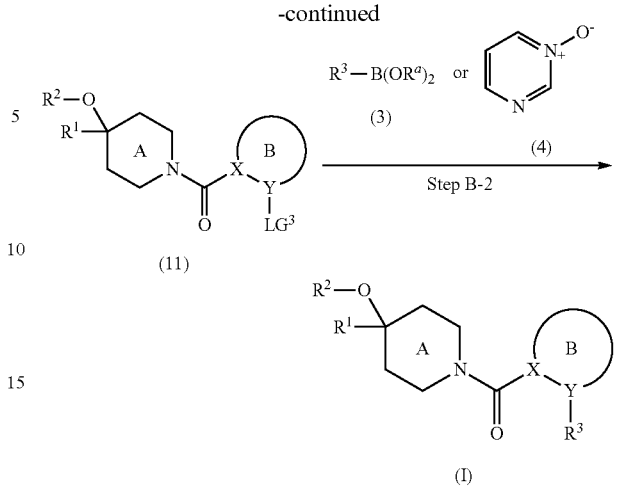

wherein each symbol is as defined above.

Compound (I) can also be produced by a sequence of reaction steps of Step B-1 to Step B-2.

(Step B-1)

Compound (11) can be produced by reacting carboxylic acid (10) or a reactive derivative thereof with compound (9). The reaction can be carried out in the same manner as in Step A-4.

(Step B-2)

Compound (I) can be produced by reacting compound (11) with compound (3) or compound (4) ($R^3$=4-pyrimidinyl). The reaction can be carried out in the same manner as in Step A-1.

[Production Method C]

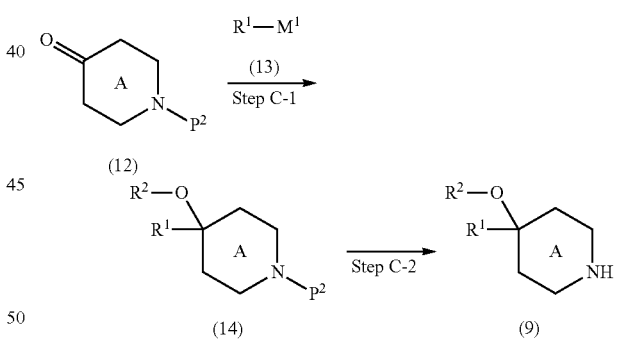

(Scheme 3)

wherein $M^1$ is a magnesium atom and halogen atom moiety derived from the Grignard reagent, or a lithium atom moiety derived from the organic lithium reagent; and the other each symbols are as defined above.

Compound (9) may be a commercially available product, or can be produced by a sequence of reaction steps of Step C-1 to Step C-2. Alternatively, compound (9) can also be produced according to a method known per se or a method analogous thereto.

(Step C-1)

Compound (14) wherein $R^2$ is a hydrogen atom can be produced by reacting compound (12) with an organic metal reagent (13). Examples of the organic metal reagent include the Grignard reagents, organic lithium reagents and the like. The amount of the organic metal reagent to be used is about 1-10 mol per 1 mol of compound (12). This reaction is advantageously carried out in a solvent inert to the reaction. While the solvent is not particularly limited as long as the reaction proceeds, preferable examples thereof include ethers, aromatic hydrocarbons, saturated hydrocarbons, amides, halogenated hydrocarbons, nitriles, sulfoxides, mixed solvents thereof and the like. While the reaction time varies depending on the reagent or solvent to be used, it is generally 10 min-100 hr. The reaction temperature is preferably −78-50° C.

When desired, the obtained compound can be subjected to an alkylation step. For example, the obtained compound can be reacted with a compound represented by $R^{2a}LG^4$ wherein $R^{2a}$ is an optionally substituted $C_{1-6}$ alkyl group, in the presence of a base.

(Step C-2)

Compound (9) can be produced by removing the protecting group $P^2$ of compound (14). The removal of the protecting group can be carried out according to a method known per se, for example, the method described in "Protective Groups in Organic Synthesis, 3rd Ed", John Wiley and Sons, Inc. (1999) (Theodora W. Greene, Peter G. M. Wuts), or the like.

The starting compound and/or the production intermediate for the aforementioned compound (I) may form a salt, which is not particularly limited as long as the reaction can be performed and, for example, those similar to the salts optionally formed by the aforementioned compound (I) and the like, and the like are used.

As for the configuration isomers (E, Z forms) of compound (I), they can be isolated and purified when isomerization occurs by, for example, a general separation means such as extraction, recrystallization, distillation, chromatography and the like, and a pure compound can be produced. In addition, it is also possible to isomerize a double bond by the methods described in Jikken Kagaku Kouza (Courses in Experimental Chemistry) 14 (The Chemical Society of Japan ed.), pages 251 to 253, 4th Edition Jikken Kagaku Kouza 19 (The Chemical Society of Japan ed.), pages 273 to 274 or a method according thereto, using heating, an acid catalyst, a transition metal complex, a metal catalyst, a radical catalyst, light irradiation or a strong base catalyst and the like, and obtain the corresponding pure isomer.

When desired, compound (I) can be synthesized by performing deprotection, acylation reaction, alkylation reaction, hydrogenation reaction, oxidation reaction, reduction reaction, carbon chain extension reaction, and substituent exchange reaction singly or two or more thereof in combination.

In each of the above-mentioned reactions, when the compound has a functional group such as an amino group, a carboxyl group or a hydroxy group, the reaction can be carried out after a protecting group generally used in peptide chemistry and the like is introduced into these groups. By removing the protecting group as necessary after the reaction, the objective compound can be obtained.

Examples of the protecting group include formyl; $C_{1-6}$ alkyl-carbonyl (e.g., acetyl, propionyl etc.), phenylcarbonyl, $C_{1-6}$ alkoxy-carbonyl (e.g., methoxycarbonyl, ethoxycarbonyl etc.), phenyloxycarbonyl, $C_{7-10}$ aralkyloxy-carbonyl (e.g., benzyloxycarbonyl etc.), trityl, phthaloyl and the like, each of which is optionally substituted. Examples of the substituent include a halogen atom (e.g., fluorine, chlorine, bromine, iodine etc.), $C_{1-6}$ alkyl-carbonyl (e.g., acetyl, propionyl, valeryl etc.), nitro and the like. The number of substituents is, for example, 1 to 3.

The removal method of the protecting group can be carried out according to a method known per se, and for example, a method using acid, base, ultraviolet rays, hydrazine, phenylhydrazine, sodium N-methyldithiocarbamate, tetrabutylammonium fluoride, palladium acetate and the like, a reduction method, and the like can be employed.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced by a method known per se. For example, when compound (I) is a basic compound, it can be produced by adding an inorganic acid or organic acid, or when compound (I) is an acidic compound, by adding an organic base or inorganic base.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include
(1) a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl) methoxycarbonylation, tetrahydrofurylation, pyrrolidylmethylation, pivaloyloxymethylation, tert-butylation, ethoxycarbonylation, tert-butoxycarbonylation, acetylation, cyclopropylcarbonylation);
(2) a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation);
(3) a compound obtained by subjecting a carboxyl group in compound (I) to esterification or amidation (e.g., a compound obtained by subjecting a carboxyl group in compound (I) to ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl)methylesterification, cyclohexyloxycarbonylethylesterification or methylamidation) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I), and a prodrug thereof are sometimes collectively abbreviated as "the compound of the present invention".

When compound (I) has isomers such as optical isomer, stereoisomer, positional isomer, rotamer and the like, such isomers and a mixture thereof are also encompassed in compound (I). For example, when compound (I) has optical isomers, an optical isomer resolved from this compound is also encompassed in compound (I). These isomers can be obtained as a single product according to synthesis methods or separation methods known per se (e.g., concentration, solvent extraction, column chromatography, recrystallization, etc.).

Compound (I) may be a crystal, and a single crystal form and a mixture of crystal forms are both encompassed in compound (I). The crystal can be produced by crystallizing according to a crystallization method known per se.

Compound (I) may be a hydrate, a non-hydrate, a solvate or a non-solvate.

Compound (I) may be labeled with an isotope (e.g., $^3$H, $^{11}$C, $^{14}$C, $^{18}$F, $^{35}$S, $^{125}$I etc.) and the like.

Compound (I) also encompasses a deuterium conversion form wherein $^1$H is converted to $^2$H(D).

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET tracer.

The compound of the present invention has low toxicity, and can be used as it is or in the form of a pharmaceutical composition by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations, or solvent, solubilizing agent, suspending agent, isotonicity agent, buffer and soothing agent for liquid preparations, and the like, and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthesis aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agents include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include p-oxybenzoates, chlorobutanol, benzyl alcohol, phenethyl alcohol, dehydroacetic acid and sorbic acid.

Preferable examples of the antioxidant include sulfite and ascorbate.

Preferable examples of the colorant include aqueous water-soluble food tar colors (e.g., food colors such as Food Color Red Nos. 2 and 3, Food Color Yellow Nos. 4 and 5, Food Color Blue Nos. 1 and 2 and the like food colors), water insoluble lake dyes (e.g., aluminum salt of the aforementioned water-soluble food tar color) and natural dyes (e.g., β-carotene, chlorophyll, ferric oxide red).

Preferable examples of the sweetening agent include saccharin sodium, dipotassium glycyrrhizinate, aspartame and *stevia*.

Examples of the dosage form of the pharmaceutical composition include oral preparations such as tablet (including sugar-coated tablet, film-coated tablet, sublingual tablet, orally disintegrating tablet), capsules (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparations (e.g., dermal preparation, ointment), suppository (e.g., rectal suppository, vaginal suppository), pellet, nasal preparation, pulmonary preparation (inhalant), eye drop and the like.

These can be respectively safely administered orally or parenterally (e.g., topically, rectally, intravenously administered).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition varies depending on the dosage form, dose of the compound of the present invention and the like, it is, for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity) and a few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior CH24H inhibitory action and can suppress nerve cell death, Aβ increase, intracerebral inflammation and the like.

Accordingly, the compound of the present invention is useful for the prophylaxis, improvement of symptoms, suppression of progression or treatment of diseases involving enhanced function of CH24H, for example, neurodegenerative disease.

In the present specification, the "neurodegenerative disease" means a disease associated with denaturation of neural tissues.

Specific examples of the neurodegenerative disease include Alzheimer's disease, mild cognitive impairment, Huntington's disease, Parkinson's disease, amyotrophic lateral sclerosis, traumatic brain injury, cerebral infarction, glaucoma, multiple sclerosis and the like.

In addition, the compound of the present invention is useful for the prophylaxis, improvement of symptoms, suppression of progression or treatment of diseases involving enhanced function of CH24H, for example, epilepsy, schizophrenia and the like.

Moreover, the compound of the present invention is useful for the prophylaxis, improvement of symptoms, suppression of progression or treatment of diseases involving enhanced function of CH24H, for example, spasm and the like.

The dose of the compound of the present invention varies depending on the administration subject, route of administration, target disease, symptoms, etc. For example, when it is administered orally to an adult patient (body weight 60 kg), its dose is about 0.01 to 100 mg/kg body weight per dose, preferably 0.05 to 30 mg/kg body weight per dose, more preferably 0.1 to 10 mg/kg body weight per dose and this amount is desirably administered in 1 to 3 portions daily.

When the compound of the present invention is applied to each of the above-mentioned diseases, it can be used in an appropriate combination with a medicament or a treatment method generally employed for the disease.

Examples of the medicament (hereinafter to be abbreviated as "concomitant drug") to be used in combination with the compound of the present invention include acetylcholine esterase inhibitors (e.g., donepezil, rivastigmine, galanthamine, zanapezil etc.), antidementian agents (e.g., memantine), inhibitors of β amyloid β rotein production, secretion, accumulation, coagulation and/or deposition, β secretase inhibitors (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl) methoxytetralin, 6-(4-biphenylyl)methoxy-2-[2-(N,N-diethylamino)ethyl]tetralin, 2-[2-(N,N-dimethylamino) ethyl]-6-(4'-methylbiphenyl-4-yl)methoxytetralin, 2-[2-(N, N-dimethylamino)ethyl]-6-(4'-methoxybiphenyl-4-yl) methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitory agent, β amyloid β rotein coagulation inhibitory agent (e.g., PTI-00703, ALZHEMED (NC-531), PPI-368 (JP-A-11-514333), PPI-558 (JP-A-2001-500852), SKF-74652 (Biochem. J. (1999), 340(1), 283-289)), β amyloid vaccine, β amyloid degrading enzyme and the like, cerebral function activators (e.g., aniracetam, nicergoline), other therapeutic drug for Parkinson's disease [(e.g., dopamine receptor agonists (e.g., L-DOPA, bromocriptine, pergolide, talipexole, pramipexole, Cabergoline, adamantadine), a monoamine oxidase (MAO) inhibitors (e.g., deprenyl, Selgiline (selegiline), remacemide, riluzole), anticholinergic agents (e.g., trihexyphenidyl, biperiden), COMT inhibitors (e.g., entacapone)], therapeutic drug for amyotropic lateral sclerosis (e.g., riluzole etc., neurotrophic factor), therapeutic drug for abnormal behavior, wandering and the like due to the progress of dementia (e.g., sedative drug, antianxiety drug), apoptosis inhibitors (e.g., CPI-1189, IDN-6556, CEP-1347), neuronal differentiation or regeneration promoters (e.g., leteprinim, xaliproden (SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl] isoindoline, 5,6-dimethoxy-2-[3-(4-isopropylphenyl)-2,2,4, 6,7-pentamethyl-2,3-dihydro-1-benzofuran-5-yl] isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and optically active forms, salts and hydrates thereof), antidepressants (e.g., desipramine, amitriptyline, imipramine, tramadol), antiepilepsy drug (e.g., lamotrigine), antianxiety drugs (e.g., benzodiazepine), non-steroidal anti-inflammatory drugs (e.g., meloxicam, tenoxicam, indomethacin, ibuprofen, celecoxib, rofecoxib, aspirin, indomethacin), disease-modifying anti-rheumatic drugs (DMARDs), anti-cytokine drugs (e.g., TNF inhibitor, MAP kinase inhibitor), steroidal drugs (e.g., dexamethasone, hexestrol, cortisone acetate), therapeutic agents for incontinence or frequent urination (e.g., flavoxate hydrochloride, oxybutynin hydrochloride, propiverine hydrochloride), phosphodiesterase inhibitors (e.g., sildenafil (citrate)), dopamine agonists (e.g., apomorphine etc.), antiarrhythmics (e.g., mexiletine), sex hormones or derivatives thereof (e.g., progesterone, estradiol, estradiol benzoate), therapeutic agents for osteoporosis (e.g., alfacalcidol, calcitriol, elcatonin, calcitonin salmon, estriol, ipriflavone, disodium pamidronate, sodium alendronate hydrate, disodium incadronate), parathyroid hormone (PTH), calcium receptor antagonists, therapeutic drugs for insomnia (e.g., benzodiazepine medicament, non-benzodiazepine medicament, melatonin agonist), therapeutic drugs for schizophrenia (e.g., typical antipsychotic agents such as haloperidol and the like; atypical antipsychotic agents such as clozapine, olanzapine, risperidone, aripiprazole and the like; medicament acted on metabotropic glutamate receptor or ionic channel-conjugated glutamate receptor; phosphodiesterase inhibitor) and the like.

In addition, a combined use with a transplantation method of neural stem cell or neural precursor cell prepared from embryonic stem cell or nervous tissue, or fetal neural tissue, and a combined use with a pharmaceutical agent such as an immunosuppressant after the transplantation and the like.

Furthermore, the compound of the present invention may be used in combination with the following concomitant drugs.

(1) Therapeutic Agent for Diabetes

For example, insulin preparations (e.g., animal insulin preparation extracted from the pancreas of bovine, swine; human insulin preparation genetically synthesized using *Escherichia coli*, yeast; zinc insulin; protamine zinc insulin; insulin fragment or derivatives (e.g., INS-1), oral insulin preparation), insulin sensitizer (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitor (e.g., voglibose, acarbose, miglitol, emiglitate), biguanide (e.g., metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof, glucose-dependent insulin secretagogue (e.g., [(3S)-6-({2',6'-dimethyl-4'-[3-(methylsulfonyl)propoxy]biphenyl-3-yl}methoxy)-2,3-dihydro-1-benzofuran-3-yl]acetic acid or a salt thereof)], dipeptidyl peptidase IV inhibitor (e.g., Alogliptin, Vildagliptin, Sitagliptin, Saxagliptin, T-6666, TS-021), β3 agonist (e.g., AJ-9677), GPR$^{40}$ agonist, GLP-1 receptor agonist [e.g., GLP-1, GLP-1MR agent, NN-2211, AC-2993 (exendin-4), BIM-51077, Aib(8,35)hGLP-1(7,37)NH$_2$, CJC-1131], amylin agonist (e.g., pramlintide), phosphotyrosine phosphatase inhibitors (e.g., sodium vanadate), gluconeogenesis inhibitor (e.g., glycogen phosphorylase inhibitor, glucose-6-phosphatase inhibitors, glucagon antagonists), SGLUT (sodium-glucose cotransporter) inhibitor (e.g., T-1095), 11β-hydroxysteroid dehydrogenase inhibitor (e.g., BVT-3498), adiponectin or an agonist thereof, IKK inhibitor (e.g., AS-2868), leptin resistance improving drugs, somatostatin receptor agonists, glucokinase activators (e.g., Ro-28-1675), GIP (Glucose-dependent insulinotropic peptide) and the like.

(2) Therapeutic Agents for Diabetic Complications

For example, aldose reductase inhibitors (e.g., tolrestat, epalrestat, zenarestat, zopolrestat, minalrestat, fidarestat, CT-112), neurotrophic factor and an increasing agent thereof (e.g., NGF, NT-3, BDNF, neurotrophic factors and increasing drugs described in WO01/14372 (e.g., 4-(4-chlorophenyl)-2-(2-methyl-1-imidazolyl)-5-[3-(2-methylphenoxyl) propyl]oxazole)), nerve regeneration promoting agent (e.g., Y-128), PKC inhibitor (e.g., ruboxistaurin mesylate), AGE inhibitor (e.g., ALT946, pimagedine, pyratoxanthine, N-phenacylthiazolium bromide (ALT766), ALT-711, EXO-226, Pyridorin, pyridoxamine), active oxygen scavengers (e.g., thioctic acid), cerebral vasodilator (e.g., tiapuride, mexiletine), somatostatin receptor agonists (e.g., BIM23190), apoptosis signal regulating kinase-1(ASK-1) inhibitor and the like can be mentioned.

(3) Therapeutic Agent for Hyperlipidemia

For example, statin compound (e.g., pravastatin, simvastatin, lovastatin, atorvastatin, fluvastatin, rosuvastatin, pitavastatin, or a salt thereof (e.g., sodium salt, calcium salt)), squalene synthase inhibitors (e.g., lapaquistat acetate or a salt thereof), fibrate compound (e.g., bezafibrate, clofibrate, simfibrate, clinofibrate), ACAT inhibitor (e.g., Avasimibe, Eflucimibe), anion exchange resin (e.g., colestyramine), probucol, nicotinic acid drug (e.g., nicomol, niceritrol), ethyl icosapentate, phytosterol (e.g., soysterol, gamma oryzanol) and the like.

(4) Antihypertensive Agent

For example, angiotensin converting enzyme inhibitor (e.g., captopril, enalapril, delapril), angiotensin II antagonist (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, Azilsartan, Azilsartan medoxomil), calcium antagonist (e.g., manidipine, nifedipine, amlodipine, efonidipine, nicardipine), potassium channel opener (e.g., levcromakalim, L-27152, AL 0671, NIP-121), clonidine and the like.

(5) Antiobesity Agent

For example, central-acting antiobesity agent (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonist (e.g., CP-422935); cannabinoid receptor antagonists (e.g., SR-141716, SR-147778); ghrelin antagonist; 11β-hydroxysteroid dehydrogenase inhibitor (e.g., BVT-3498)), pancreatic lipase inhibitors (e.g., orlistat, cetilistat), β3 agonist (e.g., AJ-9677, AZ40140), anorectic peptides (e.g., leptin, CNTF (ciliary neurotrophic factor)), cholecystokinin agonist (e.g., lintitript, FPL-15849), anorexigenic agent (e.g., P-57) and the like.

(6) Diuretic

For example, xanthine derivative (e.g., theobromine sodium salicylate, theobromine calcium salicylate), thiazide preparation (e.g., ethiazide, cyclopenthiazide, trichloromethyazide, hydrochlorothiazide, hydroflumethiazide, benzylhydrochlorothiazide, penflutizide, polythiazide, methyclothiazide), antialdosterone preparation (e.g., spironolactone, triamterene), carbonic anhydrase inhibitors (e.g., acetazolamide), chlorobenzenesulfonamide agent (e.g., chlortalidone, mefruside, indapamide), azosemide, isosorbide, ethacrynic acid, piretanide, bumetanide, furosemide and the like.

(7) Chemotherapeutic Agent

For example, alkylating agents (e.g., cyclophosphamide, ifosfamide), metabolic antagonists (e.g., methotrexate, 5-fluorouracil or derivative thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon and Neo-Furtulon, which are 5-fluorouracil derivatives, and the like are preferable.

(8) Immunotherapeutic Agent

For example, microorganism or bacterial components (e.g., muramyl dipeptide derivative, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

(9) Antithrombotic Agent

For example, heparin (e.g., heparin sodium, heparin calcium, dalteparin sodium), warfarin (e.g., warfarin potassium), anti-thrombin drug (e.g., argatroban), thrombolytic agent (e.g., urokinase, tisokinase, alteplase, nateplase, monteplase, pamiteplase), platelet aggregation inhibitor (e.g., ticlopidine hydrochloride, cilostazol, ethyl icosapentate, beraprost sodium, sarpogrelate hydrochloride) and the like.

(10) Cachexia Improving Medicament

For example, cyclooxygenase inhibitors (e.g., indomethacin etc.) [Cancer Research, Vol. 49, pages 5935-5939, 1989], progesterone derivatives (e.g., megestrol acetate) [Journal of Clinical Oncology, Vol. 12, pages 213-225, 1994], glucosteroids (e.g., dexamethasone etc.), metoclopramide agents, tetrahydrocannabinol agents (publications are all as mentioned aboe), fat metabolism improving agents (e.g., eicosapentanoic acid etc.) [British Journal of Cancer, Vol. 68, pages 314-318, 1993], growth hormones, IGF-1, or antibodies to a cachexia-inducing factor such as TNF-α, LIF, IL-6, oncostatin M and the like.

Two or more kinds of the above-mentioned concomitant drugs may be used in combination at an appropriate ratio.

It is also possible to apply compound of the present invention to each of the above-mentioned diseases in combination with a biologic (e.g., antibody, vaccine preparation and the like), or as a combination therapy in combination with gene therapy method and the like.

Examples of the antibody and vaccine preparation include vaccine preparation to angiotensin II, vaccine preparation to CETP, CETP antibody, TNFα antibody and antibody to other cytokine, amyloid β vaccine preparation, type 1 diabetes vaccine (e.g., DIAPEP-277 manufactured by Peptor Ltd.), anti-HIV antibody, HIV vaccine preparation and the like, antibody or vaccine preparation to cytokine, renin-angiotensin enzyme and a product thereof, antibody or vaccine preparation to enzyme or protein involved in blood lipid metabolism, antibody or vaccine to enzyme or protein involved in blood coagulation or fibrinolytic system, antibody or vaccine preparation to protein involved in saccharometabolism or insulin resistance and the like.

In addition, a combined use with a biological preparation involved in a growth factor such as GH, IGF and the like is possible.

Examples of the gene therapy method include a treatment method using a gene relating to cytokine, renin-angiotensin enzyme and a product thereof, G protein, G protein conjugated receptor and its phosphorylation enzyme, a treatment method using a DNA decoy such as NFκB decoy and the like, a treatment method using an antisense, a treatment method using a gene relating to an enzyme or protein involved in blood lipid metabolism (e.g., gene relating to metabolism, excretion or absorption of cholesterol or triglyceride or HDL-cholesterol or blood phospholipid), a treatment method using a gene relating to an enzyme or protein involved in angiogenesis therapy targeting obstruction of peripheral vessel and the like (e.g., growth factors such as HGF, VEGF etc.), a treatment method using a gene relating to a protein involved in saccharometabolism or insulin resistance, an antisense to cytokine such as TNF and the like, and the like.

In addition, it is possible to use in combination with various organ regeneration methods such as heart regeneration, kidney regeneration, pancreas regeneration, blood vessel regeneration and the like or cell transplantation therapy utilizing bone marrow cell (myelomonocytic cell, myeloid stem cell) or an artificial organ utilizing tissue engineering (e.g., artificial blood vessel and cardiac muscle cell sheet).

The time of administration of the compound of the present invention and that of the concomitant drug are not limited, and they may be administered simultaneously or in a staggered manner to the administration subject. Furthermore, the compound of the present invention and the concomitant drug may be administered as two kinds of preparations containing each active ingredient, or a single preparation containing both active ingredients.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like. When the subject of administration is human, for example, a concomitant drug can be used in 0.01-100 parts by weight relative to 1 part by weight of the compound of the present invention.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

The abbreviations used in the specification mean the following.
THF: tetrahydrofuran
DME: 1,2-dimethoxyethane
DMF: N,N-dimethylformamide
DMA: N,N-dimethylacetamide
DMSO: dimethyl sulfoxide
ESI: electrospray method
APCI: atmospheric chemical ionization
$[M+H]^+$: molecular ion peak M: mol concentration
N: N concentration
IPE: diisopropyl ether
HATU: 2-(1H-7-azabenzotriazol-1-yl)-1,1,3,3-tetramethyl uranium hexafluorophosphate
DMTMM: dimethoxy[1.3.5]triazin-2-yl)-4-methylmorpholinium chloride
HPLC: high performance liquid chromatography
TFA: trifluoroacetic acid
mp: melting point $^1$H NMR (protone nuclear magnetic resonance spectrum) was measured by Fourier-transform type NMR. For the analysis, ACD/SpecManager (trade name) and the like were used. Peaks with very mild protons such as a hydroxy group, an amino group and the like are note described.

MS (mass spectrum) was measured by LC/MS (liquid chromatography mass spectrometer). As the ionization method, ESI (ElectroSpray Ionization) method, or APCI (Atomospheric Pressure Chemical Ionization) method was used. The data indicates those found. Generally, a molecular ion peak is observed. In the case of a compound having a tert-butoxycarbonyl group (-Boc), a peak after elimination of a tert-butoxycarbonyl group or tert-butyl group may be observed as a fragment ion. In the case of a compound having a hydroxy group (—OH), a peak after elimination of $H_2O$ may be observed as a fragment ion. In the case of a salt, a molecular ion peak or fragment ion peak of free form is generally observed.

The elemental analysis value (Anal.) shows Calculated value (Calcd) and Found value (Found).

Example 1

(4-benzyl-4-hydroxypiperidin-1-yl)(5-methyl-2-(pyridin-4-yl)phenyl)methanone

A) methyl 5-methyl-2-(pyridin-4-yl)benzoate

A mixture of methyl 2-bromo-5-methylbenzoate (5.2 g), pyridine-4-boronic acid (4.2 g), sodium carbonate (4.8 g), tetrakis(triphenylphosphine)palladium(0) (1.3 g), water (10 mL) and DME (50 mL) was heated under reflux overnight under a nitrogen atmosphere. The reaction mixture was diluted with ethyl acetate, and filtered through silica gel. The filtrate was concentrated under reduced pressure, and the residue was purified by silica gel column chromatography (ethyl acetate/hexane) to give the title compound (2.5 g).

$^1$H NMR (300 MHz, $CDCl_3$) δ 2.45 (3H, s), 3.65 (3H, s), 7.18-7.25 (3H, m), 7.39 (1H, d, J=7.9 Hz), 7.73 (1H, s), 8.59-8.64 (2H, m).

B) 5-methyl-2-(pyridin-4-yl)benzoic acid hydrochloride

A mixture of methyl 5-methyl-2-(pyridin-4-yl)benzoate (8.8 g), 6 N hydrochloric acid (65 mL) and acetic acid (100 mL) was heated under reflux overnight. The solvent was evaporated under reduced pressure, and the obtained solid was washed with ethyl acetate to give the title compound (6.6 g).

MS (APCI+): [M+H]$^+$ 214.3.

C) (4-benzyl-4-hydroxypiperidin-1-yl)(5-methyl-2-(pyridin-4-yl)phenyl)methanone

A suspension of 5-methyl-2-(pyridin-4-yl)benzoic acid hydrochloride (0.33 g), 4-benzyl-4-hydroxypiperidine (0.38 g), HATU (0.75 g) and triethylamine (0.92 mL) in DMF (5.0 mL) was stirred overnight at room temperature. The reaction mixture was diluted with water, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane), and then purified by preparative HPLC (C18, mobile phase: water/acetonitrile (containing 0.1% TFA)), the obtained fraction was concentrated under reduced pressure. To the residue was added saturated aqueous sodium hydrogen carbonate solution, and the mixture was extracted with ethyl acetate. The extract was dried over anhydrous sodium sulfate. The solvent was evaporated under reduced pressure. The obtained solid was recrystallized from ethyl acetate/hexane to give the title compound (0.33 g).

$^1$H NMR (400 MHz, DMSO-$d_6$) δ 0.01-1.13 (2H, m), 1.22-1.49 (2H, m), 2.20-2.47 (4H, m), 2.56-2.78 (2H, m), 2.82-3.09 (2H, m), 4.09-4.29 (1H, m), 4.31-4.39 (1H, m), 6.99-7.28 (6H, m), 7.29-7.49 (4H, m), 8.52-8.66 (2H, m).

Example 2

(4-benzyl-4-hydroxypiperidin-1-yl)(3-methyl-5-(pyridin-4-yl)-1,2-oxazol-4-yl)methanone A) ethyl 3-methyl-5-(pyridin-4-yl)-1,2-oxazole-4-carboxylate To a mixture of ethyl acetoacetate (7.1 mL) and 2 M methylamine THF solution (28 mL) was added iodine (2.2 g) under water bath, and the mixture was stirred at room temperature for 3 hr. The reaction mixture was diluted with saturated brine, and extracted with ethyl acetate/THF. The extract was dried over anhydrous sodium sulfate, and the solvent was evaporated under reduced pressure.

To a solution of the obtained residue in toluene (60 mL) were added triethylamine (12 mL) and isonicotinoyl chloride (5.2 g), and the mixture was stirred overnight at room temperature. The insoluble material was filtered off, and the filtrate was concentrated under reduced pressure. The residue was diluted with saturated brine, and the mixture was extracted with ethyl acetate. The extract was dried over anhydrous sodium sulfate, and the solvent was evaporated under reduced pressure.

A suspension of the obtained residue and hydroxylamine hydrochloride (2.6 g) in acetic acid (50 mL) was heated under reflux for 3 hr, and the solvent was evaporated under reduced pressure. To the residue was added saturated aqueous sodium hydrogen carbonate solution, and the mixture was extracted with ethyl acetate. The extract was dried over anhydrous sodium sulfate, and the solvent was evaporated under reduced pressure. The residue was purified by silica gel column chromatography (ethyl acetate/hexane) to give the title compound (0.95 g).

MS (APCI+): [M+H] 233.2.

B) 3-methyl-5-(pyridin-4-yl)-1,2-oxazole-4-carboxylic acid

To a solution of ethyl 3-methyl-5-(pyridin-4-yl)-1,2-oxazole-4-carboxylate (0.95 g) in a mixed solvent of THF (20 mL)/methanol (10 mL) was added 1N aqueous sodium hydroxide solution (5.0 mL), and the mixture was stirred at room temperature for 4 hr. To the reaction mixture was added water, and the mixture was washed with ethyl acetate.

The obtained aqueous layer was acidified with 1N hydrochloric acid, sodium chloride was added thereto until the mixture became saturated, and the mixture was extracted with ethyl acetate. The extract was dried over anhydrous sodium sulfate, and the solvent was evaporated under reduced pressure to give the title compound (0.48 g).
MS (ESI+): [M+H]$^+$ 204.9.

C) (4-benzyl-4-hydroxypiperidin-1-yl)(3-methyl-5-(pyridin-4-yl)-1,2-oxazol-4-yl)methanone A suspension of 3-methyl-5-(pyridin-4-yl)-1,2-oxazole-4-carboxylic acid (0.25 g), 4-benzyl-4-hydroxypiperidine (0.35 g), HATU (0.70 g) and triethylamine (0.85 mL) in DMF (5.0 mL) was stirred at room temperature for 3 hr. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane), and then purified by preparative HPLC (C18, mobile phase: water/acetonitrile (containing 0.1% TFA)), and the obtained fraction was concentrated under reduced pressure. To the residue was added saturated aqueous sodium hydrogen carbonate solution, and the mixture was extracted with ethyl acetate. The extract was dried over anhydrous sodium sulfate, and the solvent was evaporated under reduced pressure to give the title compound (0.29 g).
$^1$H NMR (400 MHz, DMSO-d$_6$) δ 1.12-1.37 (2H, m), 1.41-1.60 (2H, m), 2.23 (3H, s), 2.65 (2H, brs), 3.05-3.31 (3H, m), 4.21-4.37 (1H, m), 4.54 (1H, s), 7.03-7.34 (5H, m), 7.50-7.60 (2H, m), 8.73 (2H, d, J=5.3 Hz).

Example 4

4-((4-hydroxy-1-(5-methyl-2-(pyridin-4-yl)benzoyl)piperidin-4-yl)methyl)benzonitrile A) tert-butyl 4-(4-bromobenzyl)-4-hydroxypiperidine-1-carboxylate To a suspension of magnesium (2.9 g) in diethyl ether (50 mL) was added dropwise 1,2-dibromoethane (0.90 mL) at room temperature, and the reaction mixture was vigorously stirred at room temperature for 20 min. To the reaction mixture was added dropwise a solution of 4-bromobenzyl bromide (25 g) in diethyl ether (150 mL) over 30 min or more at 0° C., and then added dropwise a solution of tert-butyl 4-oxopiperidine-1-carboxylate (16 g) in diethyl ether (200 mL) over 30 min or more 0° C. The reaction mixture was allowed to warm to room temperature, and stirred at room temperature for 3 hr. To the reaction mixture was added saturated aqueous ammonium chloride solution (200 mL), and the mixture was extracted with ethyl acetate. The extract was dried over anhydrous sodium sulfate, and the solvent was evaporated under reduced pressure. The residue was purified by silica gel column chromatography (ethyl acetate/hexane) to give the title compound (12 g).
$^1$H NMR (400 MHz, CDCl$_3$) δ 1.45 (9H, s), 1.47 (2H, brs), 1.55 (2H, dd, J=12.0, 3.6 Hz), 2.71 (2H, s), 3.08 (2H, t, J 11.6 Hz), 3.85 (2H, brs), 7.07 (2H, d, J=8.4 Hz), 7.44 (2H, d, J=8.4 Hz).

B) tert-butyl 4-(4-cyanobenzyl)-4-hydroxypiperidine-1-carboxylate

A mixture of tert-butyl 4-(4-bromobenzyl)-4-hydroxypiperidine-1-carboxylate (35 g), K$_4$Fe(CN)$_6$ (12 g), palladium (II) acetate (1.1 g), sodium carbonate (11 g), 2-propanol (7.5 mL) and DMA (150 mL) was stirred at 120° C. for 12 hr. The reaction mixture was allowed to cool to room temperature, diluted with dichloromethane, and filtered through celite. The filtrate was washed with water and saturated brine, dried over anhydrous magnesium sulfate, and the solvent was evaporated under reduced pressure. The residue was purified by silica gel column chromatography (ethyl acetate/hexane) to give the title compound (17 g).
$^1$H NMR (400 MHz, CDCl$_3$) δ 1.46 (9H, s), 1.47 (2H, brs), 1.55-1.56 (2H, m), 2.82 (2H, s), 3.09 (2H, t, J=11.6 Hz), 3.87 (2H, brs), 7.33 (2H, d, J=8.4 Hz), 7.62 (2H, d, J=8.4 Hz).

C) 4-(4-cyanobenzyl)-4-hydroxypiperidine hydrochloride

To a solution of tert-butyl 4-(4-cyanobenzyl)-4-hydroxypiperidine-1-carboxylate (19 g) in 1,4-dioxane (50 mL) was added 4.0 M HCl/1,4-dioxane solution (76 mL) at 0° C., and the mixture was stirred at room temperature for 10 hr. The resulting solid was collected by filtration, washed with ethyl acetate (100 mL) and diethyl ether (200 mL), and dried under reduced pressure to give the title compound (9.3 g).
$^1$H NMR (400 MHz, DMSO-d$_6$) δ 1.52 (2H, d, J=13.2 Hz), 1.72 (2H, td, J=13.2, 4.8 Hz), 2.83 (2H, s), 2.93-3.07 (4H, m), 5.00 (1H, s), 7.45 (2H, d, J=8.0 Hz), 7.76 (2H, d, J=8.0 Hz), 8.86 (1H, brs), 9.15 (1H, brs).

D) 4-((4-hydroxy-1-(5-methyl-2-(pyridin-4-yl)benzoyl)piperidin-4-yl)methyl)benzonitrile By a method similar to that in Example 1, the title compound was obtained.
$^1$H NMR (400 MHz, DMSO-d$_6$) δ −0.07-0.93 (1H, m), 0.96-1.14 (1H, m), 1.21-1.54 (2H, m), 2.28-2.48 (4H, m), 2.55-3.08 (4H, m), 4.08-4.30 (1H, m), 4.49 (1H, d, J=10.6 Hz), 7.12-7.50 (7H, m), 7.65-7.76 (2H, m), 8.60 (2H, dd, J=16.2, 5.3 Hz).

Example 8

(4-hydroxy-4-methylpiperidin-1-yl)(5-methyl-2-(pyridin-4-yl)phenyl)methanone

A) 1-(5-methyl-2-(pyridin-4-yl)benzoyl)piperidin-4-one

A suspension of 5-methyl-2-(pyridin-4-yl)benzoic acid hydrochloride (2.0 g), piperidin-4-one hydrochloride (1.2 g), DMTMM (3.3 g) and N-methylmorpholine (2.6 mL) in DMF (30 mL) was stirred at room temperature for 5 hr, and then overnight at 100° C. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane) to give the title compound (0.73 g).
MS (APCI+): [M+H]$^+$ 295.1.

B) (4-hydroxy-4-methylpiperidin-1-yl)(5-methyl-2-(pyridin-4-yl)phenyl)methanone

3 M methylmagnesium bromide-diethyl ether solution (0.84 mL) was added to a solution of 1-(5-methyl-2-(pyridin-4-yl)benzoyl)piperidin-4-one (0.37 g) in THF (10 mL) at 0° C., and the mixture was stirred overnight at room temperature. To the reaction mixture was added water at 0° C., and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane) to give the title compound (0.19 g).

$^1$H NMR (300 MHz, CDCl$_3$) δ 0.09-1.64 (8H, m), 2.42 (3H, s), 2.58-3.27 (3H, m), 4.18-4.39 (1H, m), 7.09-7.56 (5H, m), 8.61 (2H, d, J=4.5 Hz).

Example 9

(4-benzyl-4-hydroxypiperidin-1-yl)(5-(pyridin-4-yl)-1,3-benzodioxol-4-yl)methanone A) (4-benzyl-4-hydroxypiperidin-1-yl)(5-bromo-1,3-benzodioxol-4-yl)methanone A suspension of 5-bromo-1,3-benzodioxole-4-carboxylic acid (0.50 g), 4-benzyl-4-hydroxypiperidine (0.59 g), HATU (1.2 g) and triethylamine (1.4 mL) in DMF (5.0 mL) was stirred overnight at room temperature. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane) to give the title compound (0.85 g).

MS (APCI+): [M+H]$^+$ 418.1.

B) (4-benzyl-4-hydroxypiperidin-1-yl)(5-(pyridin-4-yl)-1,3-benzodioxol-4-yl)methanone A mixture of (4-benzyl-4-hydroxypiperidin-1-yl)(5-bromo-1,3-benzodioxol-4-yl)methanone (0.50 g), pyridine-4-boronic acid (0.22 g), sodium carbonate (0.38 g), tetrakis(triphenylphosphine)palladium(0) (0.069 g), water (0.50 mL) and DME (2.5 mL) was stirred at 150° C. for 1 hr under microwave irradiation. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane) to give the title compound (0.85 g).

$^1$H NMR (300 MHz, CDCl$_3$) δ 0.18-0.32 (1H×½, m), 1.03-1.12 (1H×½, m), 1.15-1.36 (2H, m), 1.42-1.74 (2H, m), 2.38-2.52 (1H, m), 2.72 (1H, s), 2.75-2.88 (1H, m), 2.97-3.25 (2H, m), 4.40-4.54 (1H, m), 6.10 (2H, s), 6.87-6.98 (2H, m), 7.02-7.16 (2H, m), 7.22-7.34 (4H, m), 7.43-7.47 (1H, m), 8.53-8.67 (2H, m).

Example 14

(4-benzyl-4-hydroxypiperidin-1-yl)(2-(pyrimidin-4-yl)phenyl)methanone

A) methyl 2-(6-chloropyrimidin-4-yl)benzoate

A mixture of methyl 2-(4,4,5,5-tetramethyl-1,3,2-dioxaborolan-2-yl)benzoate (2.0 g), 2,6-dichloropyrimidine (1.4 g), sodium carbonate (2.4 g), tetrakis(triphenylphosphine)palladium(0) (0.44 g), water (2.0 mL) and DME (10 mL) was stirred at 150° C. for 1 hr under microwave irradiation. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane) to give the title compound (0.60 g).

$^1$H NMR (300 MHz, CDCl$_3$) δ 3.75 (3H, s), 7.49-7.67 (4H, m), 7.90 (1H, dd, J=7.3, 1.3 Hz), 9.01 (1H, d, J=1.3 Hz).

B) methyl 2-(pyrimidin-4-yl)benzoate

A suspension of methyl 2-(6-chloropyrimidin-4-yl)benzoate (0.60 g), triethylamine (1.7 mL) and 10% palladium carbon (containing water (50%), 0.26 g) in methanol (20 mL) was stirred at room temperature for 1 hr under a hydrogen atmosphere. The reaction mixture was filtered, and the filtrate was concentrated under reduced pressure. To the residue was added ethyl acetate, and the mixture was washed with saturated brine. The extract was dried over anhydrous sodium sulfate, and the solvent was evaporated under reduced pressure to give the title compound (0.49 g).

MS (APCI+): [M+H]$^+$ 215.2.

C) 2-(pyrimidin-4-yl)benzoic acid hydrochloride

A mixture of methyl 2-(pyrimidin-4-yl)benzoate (0.49 g), acetic acid (2.0 mL) and 6 N hydrochloric acid (10 mL) was heated under reflux for 5 hr. The solvent was evaporated under reduced pressure, and the obtained residue was washed with ethyl acetate to give the title compound (0.45 g).

MS (APCI+): [M+H]$^+$ 201.2.

D) (4-benzyl-4-hydroxypiperidin-1-yl)(2-(pyrimidin-4-yl)phenyl)methanone

A suspension of 2-(pyrimidin-4-yl)benzoic acid hydrochloride (0.20 g), 4-benzyl-4-hydroxypiperidine (0.24 g), HATU (0.48 g) and triethylamine (0.59 mL) in DMF (3.0 mL) was stirred overnight at room temperature. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane) to give the title compound (0.11 g).

$^1$H NMR (300 MHz, CDCl$_3$) δ 1.29-1.42 (2H, m), 1.50-1.78 (3H, m), 2.61-2.82 (2H, m), 2.86-3.40 (3H, m), 4.37-4.60 (1H, m), 7.06-7.46 (6H, m), 7.47-7.84 (4H, m), 8.66-8.81 (1H, m), 8.85-9.27 (1H, m).

Example 16

(4-benzyl-4-hydroxypiperidin-1-yl)(5-methyl-3-(pyridin-4-yl)-1H-pyrazol-4-yl)methanone A) ethyl 2-isonicotinoyl-3-oxobutanoate A mixture of isonicotinic acid (10 g) and thionyl chloride (18 mL) was stirred at 70° C. for 2 hr. The reaction mixture was concentrated under reduced pressure, to the residue was added dichloromethane (280 mL), and the magnesium chloride (II) (5.1 g), pyridine (8.5 g) and ethyl 3-oxobutanoate (14 g) were added thereto at 0° C. The reaction mixture was stirred at room temperature for 3 hr, and poured into water, and the mixture was extracted with dichloromethane. The extract was washed with saturated brine, and dried over anhydrous sodium sulfate. The solvent was evaporated under reduced pressure to give the title compound (11 g).

$^1$H NMR (400 MHz, CDCl$_3$) δ 0.88 (3H, t, J=7.2 Hz), 2.46 (3H, s), 3.96 (2H, q, J=6.8 Hz), 7.36 (2H, m), 8.75 (2H, brs).

B) ethyl 5-methyl-3-(pyridin-4-yl)-1H-pyrazole-4-carboxylate

To a solution of ethyl 2-isonicotinoyl-3-oxobutanoate (8.0 g) in ethanol (80 mL) was added hydrazine (1.7 g), and the mixture was stirred at room temperature for 1 hr, and poured into saturated aqueous sodium hydrogen carbonate solution. The mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane) to give the title compound (6.4 g).

$^1$H NMR (400 MHz, CDCl$_3$) δ 1.26 (3H, t, J=7.2 Hz), 2.51 (3H, s), 4.25 (2H, q, J=6.8 Hz), 7.63 (2H, dd, J=1.6, 4.8 Hz), 8.66 (2H, dd, J=1.6, 4.8 Hz), 11.84 (1H, brs).

C) 5-methyl-3-(pyridin-4-yl)-1H-pyrazole-4-carboxylic acid

To a solution of ethyl 5-methyl-3-(pyridin-4-yl)-1H-pyrazole-4-carboxylate (3.1 g) in ethanol (20 mL) were added sodium hydroxide (8.0 g) and water (10 mL), and the mixture was heated under reflux overnight. The solvent was evaporated under reduced pressure, the pH of the mixture was adjusted to with 2 N hydrochloric acid, and mixture was concentrated under reduced pressure. The obtained solid was collected by filtration and washed with water to give the title compound (2.4 g).

$^1$H NMR (400 MHz, DMSO-d$_6$) δ 2.49 (3H, s), 7.68 (2H, d, J=6.0 Hz), 8.61 (2H, d, J=6.0 Hz), 12.5 (1H, brs), 13.5 (1H, brs).

D) (4-benzyl-4-hydroxypiperidin-1-yl)(5-methyl-3-(pyridin-4-yl)-1H-pyrazol-4-yl)methanone A mixture of 5-methyl-3-(pyridin-4-yl)-1H-pyrazole-4-carboxylic acid (0.47 g) and thionyl chloride (5 mL) was stirred at 70° C. for 2 hr. The reaction mixture was concentrated under reduced pressure, and to the residue were added dichloromethane (5.0 mL) and triethylamine (0.29 g). The mixture was added to a solution of 4-benzyl-4-hydroxypiperidine (0.36 g) in dichloromethane (5 mL), and the mixture heated under reflux for 3 hr. The reaction mixture was poured into water, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane), and then purified again by silica gel column chromatography (NH, ethyl acetate/hexane) to give the title compound (0.070 g).

$^1$H NMR (300 MHz, CDCl$_3$) δ 1.25 (2H, s), 1.63 (2H, s), 2.31 (3H, s), 2.67 (2H, s), 3.07-3.16 (1H, m), 3.30-3.34 (1H, m), 3.49 (2H, s), 4.59 (1H, d, J=12.4 Hz), 7.11 (2H, s), 7.28-7.33 (3H, m), 7.56 (2H, s), 8.61 (2H, d, J=4.8 Hz).

Example 30

(4-fluoro-2-(pyridin-4-yl)phenyl)(4-hydroxy-4-(pyridin-2-ylmethyl)piperidin-1-yl)methanone

A) methyl 4-fluoro-2-(pyridin-4-yl)benzoate

A mixture of methyl 2-bromo-4-fluorobenzoate (1.5 g), pyridine-4-boronic acid (0.95 g), sodium carbonate (1.0 g), tetrakis(triphenylphosphine)palladium(0) (0.22 g), water (1.5 mL) and DME (9.0 mL) was stirred at 120° C. for 1 hr under microwave irradiation. The reaction mixture was diluted with water, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (0.89 g).

MS (APCI+): [M+H]$^+$ 232.1.

B) 4-fluoro-2-(pyridin-4-yl)benzoic acid hydrochloride

A mixture of methyl 4-fluoro-2-(pyridin-4-yl)benzoate (0.88 g) and 6 N hydrochloric acid (13 mL) was stirred at 90° C. for 18 hr. The solvent was evaporated under reduced pressure to give the title compound (0.96 g).

$^1$H NMR (300 MHz, DMSO-d$_6$) δ 7.27-7.65 (2H, m), 7.82-8.26 (3H, m), 8.95 (2H, d, J=6.4 Hz), 13.25 (1H, brs).

C) (4-fluoro-2-(pyridin-4-yl)phenyl)(4-hydroxy-4-(pyridin-2-ylmethyl)piperidin-1-yl)methanone A suspension of 4-fluoro-2-(pyridin-4-yl)benzoic acid hydrochloride (0.15 g), 4-(pyridin-2-ylmethyl)piperidin-4-ol (0.17 g), HATU (0.34 g) and triethylamine (0.41 mL) in DMF (2.0 mL) was stirred at room temperature for 2 hr. The reaction mixture was diluted with water, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (0.16 g).

$^1$H NMR (300 MHz, CDCl$_3$) δ 0.97-1.12 (1H, m), 1.20-1.34 (1H, m), 1.39-1.60 (2H, m), 2.55 (1H, s), 2.74-3.29 (4H, m), 4.40 (1H, d, J=13.2 Hz), 7.01-7.23 (4H, m), 7.31-7.54 (3H, m), 7.63 (1H, t, J=7.6 Hz), 8.44 (1H, brs), 8.58-8.76 (2H, m).

Example 37

(4-(4-fluorobenzyl)-4-hydroxypiperidin-1-yl)(5-methyl-2-(pyridin-4-yl)phenyl)methanone

A) tert-butyl 4-(4-fluorobenzyl)-4-hydroxypiperidine-1-carboxylate

To a suspension of magnesium (1.2 g) and 1,2-dibromoethane (0.11 mL) in THF (30 mL) was added a solution of 4-fluorobenzyl chloride (6.3 mL) in THF (10 mL) at room temperature under a nitrogen atmosphere, and the mixture was stirred for 1 hr at the same temperature. The reaction mixture was cooled to −78° C., a solution of tert-butyl 4-oxopiperidine-1-carboxylate (5.0 g) in THF (10 mL) was added thereto, and the mixture was allowed to warm to room temperature, and stirred for 2 days. To the reaction mixture was added water at 0° C., and then saturated aqueous potassium sodium tartrate solution, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane), and recrystallized from ethyl acetate/hexane to give the title compound (4.8 g).
$^1$H NMR (300 MHz, CDCl$_3$) δ 1.34-1.72 (13H, m), 2.73 (2H, s), 3.09 (2H, t, J=11.3 Hz), 3.85 (2H, d, J=9.8 Hz), 6.95-7.06 (2H, m), 7.10-7.20 (2H, m).

B) 4-(4-fluorobenzyl)-4-hydroxypiperidine hydrochloride

To a solution of tert-butyl 4-(4-fluorobenzyl)-4-hydroxypiperidine-1-carboxylate (2.0 g) in ethanol (10 mL) was added 2.0 M HCl/ethanol solution (20 mL), and the mixture was stirred at room temperature for 3 hr. The solvent was evaporated under reduced pressure, and the obtained solid was recrystallized from ethanol/hexane to give the title compound (1.4 g).
$^1$H NMR (400 MHz, DMSO-d$_6$) δ1.40-1.77 (4H, m), 2.71 (2H, s), 2.86-3.16 (4H, m), 4.79 (1H, s), 7.02-7.33 (4H, m), 8.83 (2H, brs).

C) (4-(4-fluorobenzyl)-4-hydroxypiperidin-1-yl)(5-methyl-2-(pyridin-4-yl)phenyl)methanone By a method similar to that in Example 1, the title compound was obtained.
$^1$H NMR (300 MHz, CDCl$_3$) δ 0.08-1.56 (5H, m), 2.28-2.47 (4H, m), 2.51-2.82 (2H, m), 2.87-3.15 (2H, m), 4.33-4.59 (1H, m), 6.88-7.57 (9H, m), 8.52-8.75 (2H, m).

Example 44

(4-benzyl-4-hydroxypiperidin-1-yl)(2,4'-bipyridin-3-yl)methanone

A) ethyl 2,4'-bipyridine-3-carboxylate

A mixture of ethyl 2-chloronicotinate (16.2 g), pyridine-4-boronic acid (12.9 g), sodium carbonate (27.8 g), tetrakis(triphenylphosphine)palladium(0) (5.04 g), water (50.0 mL) and DME (250 mL) was stirred overnight at 100° C. under a nitrogen atmosphere. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane) to give the title compound (14.1 g).
$^1$H NMR (300 MHz, CDCl$_3$) δ 1.09 (3H, t, J=7.0 Hz), 4.19 (2H, q, J=7.0 Hz), 7.39-7.48 (3H, m), 8.21 (1H, dd, J=7.8, 1.7 Hz), 8.66-8.74 (2H, m), 8.81 (1H, dd, J=4.7, 1.7 Hz).

B) 2,4'-bipyridine-3-carboxylic acid dihydrochloride

A solution of ethyl 2,4'-bipyridine-3-carboxylate (14.1 g) in 6 N hydrochloric acid (200 mL) was heated under reflux overnight. The solvent was evaporated under reduced pressure, to the obtained residue was added toluene, and the solvent was again evaporated under reduced pressure to give the title compound (16.4 g).
MS (APCI+): [M+H]$^+$ 201.1.

C) (4-benzyl-4-hydroxypiperidin-1-yl)(2,4'-bipyridin-3-yl)methanone

A suspension of 2,4'-bipyridine-3-carboxylic acid dihydrochloride (5.0 g), 4-benzyl-4-hydroxypiperidine (3.9 g), HATU (10 g) and triethylamine (13 mL) in DMF (50 mL) was stirred overnight at room temperature. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane), and recrystallized from ethyl acetate/hexane to give the title compound (3.2 g).
$^1$H NMR (300 MHz, CDCl$_3$) δ 0.06-1.74 (5H, m), 2.34-3.18 (5H, m), 4.42-4.60 (1H, m), 6.98-7.15 (2H, m), 7.21-7.34 (3H, m), 7.41 (1H, dd, J=7.6, 4.9 Hz), 7.61 (1H, d, J=5.3 Hz), 7.70-7.83 (2H, m), 8.62-8.81 (3H, m).
mp 150-152° C.

Example 54

(4-benzyl-4-hydroxypiperidin-1-yl) (2-(pyrimidin-4-yl)pyridin-3-yl)methanone

A) methyl 2-(3-oxidepyrimidin-4-yl)nicotinate

A mixture of methyl 2-chloronicotinate (2.0 g), pyrimidine 1-oxide (0.95 g), potassium carbonate (3.2 g), palladium(II) acetate (0.13 g), tri-tert-butylphosphine tetrafluoroborate (0.51 g), copper(I) cyanide (0.10 g) and 1,4-dioxane (20 mL) was stirred at 150° C. for 2 hr under microwave irradiation. The reaction mixture was diluted with ethyl acetate, and filtered through celite. The filtrate was concentrated under reduced pressure, and the residue was purified by silica gel column chromatography (ethyl acetate/hexane) to give the title compound (0.48 g).
MS (APCI+): [M+H]$^+$ 232.1.

B) methyl 2-(pyrimidin-4-yl)nicotinate

A suspension of methyl 2-(3-oxidepyrimidin-4-yl)nicotinate (0.28 g), triethylamine (0.84 mL) and 10% palladium carbon (containing water (50%), 0.20 g) in methanol (10 mL) was stirred at room temperature for 5 hr under a hydrogen atmosphere. The reaction mixture was filtered, and the filtrate was concentrated under reduced pressure. The residue was purified by silica gel column chromatography (ethyl acetate/hexane) to give the title compound (0.20 g).
MS (APCI+): [M+H]$^+$ 216.0.

C) 2-(pyrimidin-4-yl)nicotinic acid dihydrochloride

A mixture of methyl 2-(pyrimidin-4-yl)nicotinate (0.19 g), acetic acid (1.0 mL) and 6 N hydrochloric acid (5 mL) was heated under reflux for 5 hr. The solvent was evaporated under reduced pressure to give the title compound (0.26 g).
MS (APCI+): [M+H]$^+$ 202.1.

D) (4-benzyl-4-hydroxypiperidin-1-yl)(2-(pyrimidin-4-yl)pyridin-3-yl)methanone

A suspension of 2-(pyrimidin-4-yl)nicotinic acid dihydrochloride (0.24 g), 4-benzyl-4-hydroxypiperidine (0.20 g), HATU (0.50 g) and triethylamine (0.74 mL) in DMF (6 mL)

was stirred overnight at room temperature. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane), and recrystallized from ethyl acetate/hexane to give the title compound (0.085 g).

$^1$H NMR (300 MHz, CDCl$_3$) δ 1.27-2.00 (5H, m), 2.80 (2H, s), 3.09-3.52 (3H, m), 4.43-4.67 (1H, m), 7.12-7.22 (2H, m), 7.28-7.50 (4H, m), 7.61-7.75 (1H, m), 8.16-8.27 (1H, m), 8.73-9.23 (3H, m).

Example 67

2,4'-bipyridin-3-yl(4-(4-fluorobenzyl)-4-hydroxypiperidin-1-yl)methanone

A suspension of 2-chloronicotinic acid (0.15 g), 4-(4-fluorobenzyl)-4-hydroxypiperidine hydrochloride (0.26 g), HATU (0.43 g) and triethylamine (0.66 mL) in DMF (5 mL) was stirred at room temperature for 4 hr. The reaction mixture was diluted with water, and the mixture was extracted with ethyl acetate. The extract was washed with saturated brine, and dried over anhydrous sodium sulfate. The solvent was evaporated under reduced pressure. The residue was dissolved in DME (5.0 mL), and pyridine-4-boronic acid (0.13 g), sodium carbonate (0.20 g), tetrakis (triphenylphosphine)palladium(0) (0.055 g) and water (1.0 mL) were added thereto, and the mixture was stirred at 140° C. for 1 hr under microwave irradiation. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane), and then purified by preparative HPLC (C18, mobile phase: water/acetonitrile (containing 0.1% TFA)), and the obtained fraction was concentrated under reduced pressure. To the residue was added saturated aqueous sodium hydrogen carbonate solution, and the mixture was extracted with ethyl acetate. The extract was dried over anhydrous sodium sulfate, and the solvent was evaporated under reduced pressure to give the title compound (0.21 g).

$^1$H NMR (300 MHz, CDCl$_3$) b 0.83-1.58 (5H, m), 2.31-2.50 (1H, m), 2.56-3.18 (4H, m), 4.39-4.62 (1H, m), 6.89-7.18 (4H, m), 7.42 (1H, dd, J=7.5, 4.9 Hz), 7.61 (1H, d, J=4.9 Hz), 7.69-7.86 (2H, m), 8.67 (1H, d, J=4.5 Hz), 8.71-8.83 (2H, m).

Example 70

4-((1-(2,4'-bipyridin-3-ylcarbonyl)-4-hydroxypiperidin-4-yl)methyl)benzonitrile

A) 4-(1-((2-chloropyridin-3-yl)carbonyl)-4-hydroxypiperidin-4-yl)methyl)benzonitrile A suspension of 2-chloronicotinic acid (0.20 g), 4-(4-cyanobenzyl)-4-hydroxypiperidine hydrochloride (0.32 g), HATU (0.72 g) and triethylamine (0.89 mL) in DMF (4.0 mL) was stirred overnight at room temperature. The reaction mixture was diluted with water, and the mixture was extracted with ethyl acetate. The extract was washed with saturated brine, and dried over anhydrous sodium sulfate, and filtered through basic silica gel. The filtrate was concentrated under reduced pressure to give the title compound (0.45 g).

MS (APCI+): [M+H]$^+$ 356.0.

B) 4-((1-(2,4'-bipyridin-3-ylcarbonyl)-4-hydroxypiperidin-4-yl)methyl)benzonitrile A mixture of 4-(1-((2-chloropyridin-3-yl)carbonyl)-4-hydroxypiperidin-4-yl)benzonitrile (0.45 g), pyridine-4-boronic acid (0.19 g), sodium carbonate (0.40 g), tetrakis (triphenylphosphine)palladium(0) (0.073 g), water (0.60 mL) and DME (3.0 mL) was stirred at 150° C. for 1 hr under microwave irradiation. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane) to give the title compound (0.27 g).

$^1$H NMR (300 MHz, CDCl$_3$) δ 0.00-1.62 (5H, m), 2.35-3.17 (5H, m), 4.41-4.63 (1H, m), 7.16-7.45 (3H, m), 7.50-7.85 (5H, m), 8.65 (1H, d, J=4.9 Hz), 8.71-8.84 (2H, m).

Example 82

(4-benzyl-4-hydroxypiperidin-1-yl)(2-(1,3-oxazol-5-yl)phenyl)methanone

A) methyl 2-(1,3-oxazol-5-yl)benzoate

To a solution of methyl 2-formylbenzoate (15 g) and tosylmethyl isocyanide (18 g) in methanol (250 mL) was added potassium carbonate (15 g), and the mixture was heated under reflux for 16 hr. The reaction mixture was concentrated under reduced pressure, the residue was diluted with ethyl acetate, and the mixture was washed with water and saturated brine. The extract was dried over anhydrous sodium sulfate, and the solvent was evaporated under reduced pressure. The residue was purified by silica gel column chromatography (ethyl acetate/petroleum ether) to give the title compound (4.0 g).

$^1$H NMR (300 MHz, CDCl$_3$) δ 3.85 (3H, s), 7.30 (1H, s), 7.40-7.50 (1H, m), 7.50-7.65 (2H, m), 7.75-7.85 (1H, m), 7.94 (1H, s).

B) 2-(1,3-oxazol-5-yl)benzoic acid

To a solution of methyl 2-(1,3-oxazol-5-yl)benzoate (4.0 g) in THF (40 mL) was added 2 N aqueous sodium hydroxide solution (20 mL), and the mixture was stirred at room temperature stirred for 2 days. To the reaction mixture was added water, and the mixture was washed with tert-butyl methyl ether. The pH of the obtained aqueous layer was adjusted to 2 with 2N hydrochloric acid, and the mixture was extracted with ethyl acetate. The extract was washed with saturated brine, and dried over anhydrous sodium sulfate. The solvent was evaporated under reduced pressure. The residue was washed with ethyl acetate/petroleum ether to give the title compound (3.3 g)

$^1$H NMR (400 MHz, DMSO-d$_6$) δ 7.45 (1H, s), 7.50-7.60 (1H, m), 7.60-7.70 (2H, m), 7.70-7.80 (1H, m), 8.46 (1H, s), 13.19 (1H, brs).

C) (4-benzyl-4-hydroxypiperidin-1-yl)(2-(1,3-oxazol-5-yl)phenyl)methanone

A suspension of 2-(1,3-oxazol-5-yl)benzoic acid (0.30 g), 4-benzyl-4-hydroxypiperidine (0.36 g), 1-(3-dimethylaminopropyl)-3-ethylcarbodiimide hydrochloride (0.46 g), 1-hydroxybenzotriazole (0.40 g) and triethylamine (0.40 g) in DMF (3 mL) was stirred at room temperature for 16 hr. The reaction mixture was diluted with water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/petroleum ether) to give the title compound (0.28 g).

MS (APCI+): [M+H]+ 363.2.

$^1$H NMR (400 MHz, CDCl$_3$) δ 0.90-1.05 (0.5H, m), 1.20-1.40 (2H, m), 1.40-1.55 (0.5H, m), 1.55-1.65 (1.5H, m), 1.70-1.80 (0.5H, m), 2.60-2.83 (2H, m), 3.00-3.30 (3H, m), 4.50-4.70 (1H, m), 7.10-7.20 (2H, m), 7.20-7.25 (0.5H, m), 7.30-7.40 (4H, m), 7.40-7.50 (2.5H, m), 7.65-7.75 (1H, m), 7.79 (0.5H, s), 7.89 (0.5H, s).

Example 86

2,4'-bipyridin-3-yl(4-(3,4-difluorobenzyl)-4-hydroxypiperidin-1-yl)methanone

A) tert-butyl 4-(3,4-difluorobenzyl)-4-hydroxypiperidine-1-carboxylate

To a suspension of magnesium (1.2 g) and 1,2-dibromoethane (0.11 mL) in diethyl ether (30 mL) was added a solution of 3,4-difluorobenzyl bromide (10 g) in diethyl ether (10 mL) at room temperature under a nitrogen atmosphere, and the mixture was stirred at the same temperature for 1 hr. The reaction mixture was diluted with THF (30 mL), and cooled to −78° C. A solution of tert-butyl 4-oxopiperidine-1-carboxylate (5.0 g) in THF (10 mL) was added thereto, and the mixture was allowed to warm to room temperature, and was stirred overnight. To the reaction mixture was added a small amount of 1N hydrochloric acid at 0° C. to quench the reaction. Saturated aqueous potassium sodium tartrate solution was added thereto, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane), and recrystallized from ethyl acetate/hexane to give the title compound (4.9 g).

$^1$H NMR (300 MHz, CDCl$_3$) δ 1.37-1.68 (14H, m), 2.71 (2H, s), 3.09 (2H, t, J=11.5 Hz), 3.86 (2H, d, J=9.8 Hz), 6.90 (1H, ddd, J=6.1, 4.1, 2.3 Hz), 6.97-7.18 (2H, m).

B) 4-(3,4-difluorobenzyl)-4-hydroxypiperidine hydrochloride

To a solution of tert-butyl 4-(3,4-difluorobenzyl)-4-hydroxypiperidine-1-carboxylate (4.7 g) in ethanol (30 mL) was added 2.0 M HCl/ethanol solution (36 mL), and the mixture was stirred overnight at room temperature. The solvent was evaporated under reduced pressure, and the obtained solid was recrystallized from ethyl acetate/diisopropyl ether to give the title compound (3.5 g).

$^1$H NMR (400 MHz, DMSO-d$_6$) b 1.38-1.81 (4H, m), 2.72 (2H, s), 2.88-3.14 (4H, m), 4.91 (1H, s), 6.97-7.16 (1H, m), 7.23-7.43 (2H, m), 8.98 (2H, brs).

C) 2,4'-bipyridin-3-yl(4-(3,4-difluorobenzyl)-4-hydroxypiperidin-1-yl)methanone

A suspension of 2,4'-bipyridine-3-carboxylic acid dihydrochloride (0.30 g), 4-(3,4-difluorobenzyl)-4-hydroxypiperidine hydrochloride (0.38 g), HATU (0.63 g) and triethylamine (0.77 mL) in DMF (4.0 mL) was stirred at room temperature for 18 hr. The reaction mixture was diluted with water, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, ethyl acetate/hexane) to give the title compound (0.32 g).

$^1$H NMR (300 MHz, CDCl$_3$) δ 0.84-1.00 (1H, m), 1.11-1.38 (2H, m), 1.43-1.60 (1H, m), 2.28-2.49 (1H, m), 2.55-2.75 (1H, m), 2.78-3.17 (3H, m), 4.41-4.62 (1H, m), 6.67-7.01 (2H, m), 7.01-7.17 (1H, m), 7.43 (1H, dd, J=7.5, 4.9 Hz), 7.62 (1H, d, J=4.5 Hz), 7.71-7.86 (2H, m), 8.67 (1H, d, J=4.9 Hz), 8.72-8.84 (2H, m).

Example 87

2,4'-bipyridin-3-yl(4-(2,4-difluorobenzyl)-4-hydroxypiperidin-1-yl)methanone

A) tert-butyl 4-(2,4-difluorobenzyl)-4-hydroxypiperidine-1-carboxylate

To a suspension of magnesium (1.2 g) and 1,2-dibromoethane (0.11 mL) in diethyl ether (30 mL) was added a solution of 2,4-difluorobenzyl bromide (10 g) in diethyl ether (10 mL) at room temperature under a nitrogen atmosphere, and the mixture was stirred at the same temperature for 1 hr. The reaction mixture was diluted with THF (30 mL), and cooled to −78° C., and a solution of tert-butyl 4-oxopiperidine-1-carboxylate (5.0 g) in THF (10 mL) was added thereto. The mixture was allowed to warm to room temperature, and stirred overnight. To the reaction mixture was added a small amount of 1N hydrochloric acid at 0° C. to quench the reaction. Saturated aqueous potassium sodium tartrate solution was added thereto, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane), and recrystallized from ethyl acetate/hexane to give the title compound (3.9 g).

$^1$H NMR (300 MHz, CDCl$_3$) δ 1.38-1.52 (11H, m), 1.56-1.73 (2H, m), 2.78 (2H, d, J=1.1 Hz), 3.10 (2H, t, J=11.5 Hz), 3.86 (2H, d, J=10.2 Hz), 6.76-6.90 (2H, m), 7.19 (1H, td, J=8.6, 6.6 Hz).

B) 4-(2,4-difluorobenzyl)-4-hydroxypiperidine hydrochloride

To a solution of tert-butyl 4-(2,4-difluorobenzyl)-4-hydroxypiperidine-1-carboxylate (3.7 g) in ethanol (30 mL) was added 2.0 M HCl/ethanol solution (28 mL), and the mixture was stirred overnight at room temperature. The solvent was evaporated under reduced pressure, and the obtained solid was recrystallized from ethyl acetate/diisopropyl ether to give the title compound (2.9 g).

$^1$H NMR (400 MHz, DMSO-d$_6$) δ 1.39-1.87 (4H, m), 2.73 (2H, s), 2.87-3.16 (4H, m), 4.92 (1H, s), 7.04 (1H, td, J=8.5, 2.6 Hz), 7.18 (1H, td, J=9.9, 2.4 Hz), 7.30-7.50 (1H, m), 8.76 (1H, brs), 9.10 (1H, brs).

C) 2,4'-bipyridin-3-yl(4-(2,4-difluorobenzyl)-4-hydroxypiperidin-1-yl)methanone

A suspension of 2,4'-bipyridine-3-carboxylic acid dihydrochloride (0.30 g), 4-(2,4-difluorobenzyl)-4-hydroxypiperidine hydrochloride (0.38 g), HATU (0.63 g) and triethylamine (0.77 mL) in DMF (4.0 mL) was stirred at room temperature for 18 hr. The reaction mixture was diluted with water, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, ethyl acetate/hexane) to give the title compound (0.30 g).

$^1$H NMR (300 MHz, CDCl$_3$) δ 0.81-1.62 (4H, m), 2.36-2.57 (1H, m), 2.60-3.20 (4H, m), 4.39-4.62 (1H, m), 6.71-6.90 (2H, m), 6.95-7.20 (1H, m), 7.36-7.49 (1H, m), 7.63 (1H, brs), 7.74 (2H, brs), 8.53-8.88 (3H, m).

Example 92

(4-(4-fluorobenzyl)-4-hydroxypiperidin-1-yl)(2-(pyrimidin-4-yl)pyridin-3-yl)methanone A suspension of 2-(pyrimidin-4-yl)nicotinic acid dihydrochloride (0.25 g), 4-(4-fluorobenzyl)-4-hydroxypiperidine hydrochloride (0.22 g), HATU (0.52 g) and triethylamine (0.76 mL) in DMF (3 mL) was stirred overnight at room temperature. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane), and recrystallized from ethyl acetate/hexane to give the title compound (0.050 g).

$^1$H NMR (300 MHz, CDCl$_3$) δ 1.21-1.98 (5H, m), 2.76 (2H, 3), 3.10-3.50 (3H, m), 4.44-4.67 (1H, m), 6.96-7.07 (2H, m), 7.09-7.20 (2H, m), 7.40-7.50 (1H, m), 7.62-7.76 (1H, m), 8.23 (1H, d, J=4.9 Hz), 8.74 (1H, dd, J=4.5, 1.5 Hz), 8.81-9.23 (2H, m).

mp 171-173° C.

Example 44

(4-benzyl-4-hydroxypiperidin-1-yl)(2,4'-bipyridin-3-yl)methanone

A) (4-benzyl-4-hydroxypiperidin-1-yl)(2-chloropyridin-3-yl)methanone

To a mixture of 2-chloronicotinic acid (1.0 g), toluene (15 mL) and DME (5 mL) was added thionyl chloride (0.51 mL), and the mixture was stirred at 90° C. for 4 hr under a nitrogen atmosphere. The reaction mixture was concentrated under reduced pressure, the residue was dissolved in THF (15 mL), and triethylamine (0.97 mL) and 4-benzyl-4-hydroxypiperidine (1.1 g) were added thereto. The reaction mixture was stirred overnight at room temperature under a nitrogen atmosphere, saturated aqueous sodium hydrogen carbonate solution was added thereto, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane) to give the title compound (1.9 g).

MS (APCI+): [M+H] +331.1.

B) (4-benzyl-4-hydroxypiperidin-1-yl)(2,4'-bipyridin-3-yl)methanone

A mixture of (4-benzyl-4-hydroxypiperidin-1-yl) (2-chloropyridin-3-yl)methanone (5.0 g), tetrakis(triphenylphosphine)palladium(0) (0.87 g), pyridine-4-boronic acid (2.2 g), sodium carbonate (4.8 g), DMF (50 mL) and water (10 ml) was stirred overnight at 100° C. under a nitrogen atmosphere. To the reaction mixture was added saturated brine, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane) to give the title compound (3.4 g). The compound was crystallized from ethyl acetate/heptane to give the title compound as crystals.

$^1$H NMR (300 MHz, CDCl$_3$) δ 0.05-1.73 (5H, m), 2.34-2.53 (1H, m), 2.61-3.25 (4H, m), 4.37-4.64 (1H, m), 6.96-7.16 (2H, m), 7.19-7.34 (3H, m), 7.42 (1H, dd, J=7.6, 4.9 Hz), 7.54-7.85 (3H, m), 8.60-8.83 (3H, m). mp 150° C.

Example 92

(4-(4-fluorobenzyl)-4-hydroxypiperidin-1-yl) (2-(pyrimidin-4-yl)pyridin-3-yl)methanone A) ethyl 2-(1-ethoxyvinyl)nicotinate To a mixture of ethyl 2-chloronicotinate (23 g), tributyl (1-ethoxyvinyl)tin (64 mL) and toluene (400 mL) was added tetrakis(triphenylphosphine)palladium(0) (7.3 g), and the mixture was stirred overnight at 80° C. under an argon atmosphere. The solvent was evaporated under reduced pressure, and the residue was purified by silica gel column chromatography (NH, ethyl acetate/hexane), and then purified by silica gel column chromatography (ethyl acetate/hexane) to give the title compound (27 g).

$^1$H NMR (300 MHz, CDCl$_3$) δ 1.31-1.42 (6H, m), 3.91 (2H, q, J=7.2 Hz), 4.34 (2H, q, J=7.2 Hz), 4.43 (1H, d, J=2.3 Hz), 4.95 (1H, d, J=2.3 Hz), 7.29 (1H, dd, J=7.9, 4.9 Hz), 7.89 (1H, dd, J=7.7, 1.7 Hz), 8.64 (1H, dd, J=4.9, 1.9 Hz).

B) ethyl 2-acetylnicotinate

To a mixture of ethyl 2-(1-ethoxyvinyl)nicotinate (27 g) and acetone (300 mL) was added 2M hydrochloric acid (370 mL), and the mixture was stirred overnight at room temperature. The solvent was evaporated under reduced pressure, to the residue were added ethyl acetate and saturated aqueous sodium hydrogen carbonate solution, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane) to give the title compound (15 g).

$^1$H NMR (300 MHz, CDCl$_3$) δ 1.37 (3H, t, J=7.2 Hz), 2.69 (3H, s), 4.39 (2H, q, J=7.2 Hz), 7.47 (1H, dd, J=7.7, 4.7 Hz), 8.02 (1H, dd, J=7.9, 1.5 Hz), 8.71 (1H, dd, J=4.9, 1.5 Hz).

C) (4-(4-fluorobenzyl)-4-hydroxypiperidin-1-yl)(2-(pyrimidin-4-yl)pyridin-3-yl)methanone A mixture of ethyl 2-acetylnicotinate (15 g), dimethylformamide dimethyl acetal (150 mL) and acetonitrile (150 mL) was heated under reflux overnight. The reaction mixture was concentrated under reduced pressure. The obtained solid was washed with a mixed solvent of ethyl acetate and hexane, and dissolved in n-butanol (150 mL) and N,N-diisopropylethylamine (150 mL). Formamidine acetate (48 g) was added thereto, and the mixture was heated under reflux for 3 days, and concentrated under reduced pressure. To the residue was added ethyl acetate, and the mixture was washed with water and saturated brine. To the aqueous layer was added potassium carbonate, and the mixture was extracted with ethyl acetate. The combined organic layers were dried over anhydrous sodium sulfate, and the solvent was evaporated under reduced pressure. The residue was purified by silica gel column chromatography (ethyl acetate/hexane) to give ethyl 2-(pyrimidin-4-yl)nicotinate (5.8 g) and butyl 2-(pyrimidin-4-yl)nicotinate (1.8 g), respectively. A mixture thereof was dissolved in a mixed solvent of ethanol (100 mL) and water (20 mL), 4M aqueous lithium hydroxide solution (13 mL) was added thereto, and the mixture was stirred overnight at room temperature. The reaction mixture was concentrated under reduced pressure, and the obtained residue was dissolved in water. The pH of the solution was adjusted to 4 with 1M hydrochloric acid, and reaction mixture was concentrated under reduced pressure. To the obtained residue were added DMF (100 mL), triethylamine (15 mL), 4-(4-fluorobenzyl)-4-hydroxypiperidine hydrochloride (6.5 g) and HATU (13 g), and the mixture was stirred overnight at room temperature. To the reaction mixture was added water, the insoluble material was removed by filtration, and the filtrate was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane), and then purified by silica gel column chromatography (methanol/ethyl acetate), and crystallized from ethyl acetate/hexane to give the title compound (2.5 g) as crystals.

$^1$H NMR (300 MHz, CDCl$_3$) δ 1.18-2.09 (5H, m), 2.77 (2H, brs), 3.08-3.63 (3H, m), 4.61 (1H, d, J=12.1 Hz), 6.91-7.86 (6H, m), 8.25 (1H, brs), 8.68-9.36 (3H, m).

mp 174° C.

Example 102

(4-(2,4-difluorobenzyl)-4-hydroxypiperidin-1-yl) (2-(1,3-oxazol-5-yl)phenyl)methanone A suspension of 2-(1,3-oxazol-5-yl)benzoic acid (0.15 g), 4-(2,4-difluorobenzyl)-4-hydroxypiperidine hydrochloride (0.16 g), HATU (0.36 g) and triethylamine (1.1 mL) in DMF (5.0 mL) was stirred overnight at room temperature. The reaction mixture was diluted with water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (0.26 g).

$^1$H NMR (300 MHz, CDCl$_3$) δ 0.81-1.86 (5H, m), 2.67 (1H, s), 2.79 (1H, s), 2.99-3.36 (3H, m), 4.60 (1H, m), 6.74-6.90 (2H, m), 7.04-7.23 (1H, m), 7.27-7.52 (4H, m), 7.71 (1H, m), 7.90 (1H, s).

Example 105

(4-(2,4-difluorobenzyl)-4-hydroxypiperidin-1-yl)(2-(pyrimidin-4-yl)pyridin-3-yl)methanone A suspension of 2-(pyrimidin-4-yl)nicotinic acid dihydrochloride (0.36 g), 4-(2,4-difluorobenzyl)-4-hydroxypiperidine hydrochloride (0.42 g), HATU (0.75 g) and triethylamine (1.1 mL) in DMF (5 mL) was stirred overnight at room temperature. The reaction mixture was diluted with water, and the mixture was extracted with ethyl acetate. The extract was washed with saturated brine, and dried over anhydrous sodium sulfate. The solvent was evaporated under reduced pressure. The residue was purified by silica gel column chromatography (NH, ethyl acetate/hexane), and recrystallized from ethyl acetate/hexane to give the title compound (0.18 g).

$^1$H NMR (300 MHz, CDCl$_3$) δ 1.29-2.01 (5H, m), 2.80 (2H, s), 3.09-3.49 (3H, m), 4.40-4.66 (1H, m), 6.76-6.91 (2H, m), 7.10-7.24 (1H, m), 7.38-7.51 (1H, m), 7.60-7.76 (1H, m), 8.17-8.29 (1H, m), 8.70-8.78 (1H, m), 8.79-8.90 (1H, m), 8.91-9.23 (1H, m).

The compounds of the examples produced according to the above-mentioned method or a method analogous thereto are shown in the following tables. MS in the tables means those found.

TABLE 1

| Example No. | IUPAC Name | Chemical Structure | MS |
|---|---|---|---|
| 1 | (4-benzyl-4-hydroxypiperidin-1-yl) (5-methyl-2-(pyridin-4-yl)phenyl)methanone | 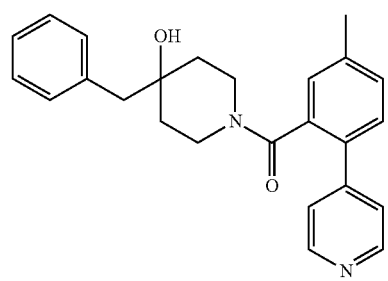 [SMILES: Cc1ccc(-c2ccncc2)c(C(=O)N2CCC(O)(Cc3ccccc3)CC2)c1] | 387.2 |

TABLE 1-continued

| Example No. | IUPAC Name | Chemical Structure | MS |
|---|---|---|---|
| 2 | (4-benzyl-4-hydroxypiperidin-1-yl) (3-methyl-5-(pyridin-4-yl)-1,2-oxazol-4-yl)methanone | 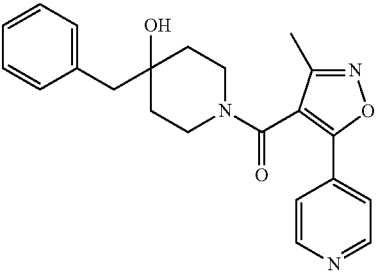 [SMILES: Cc1noc(-c2ccncc2)c1C(=O)N1CCC(O)(Cc2ccccc2)CC1] | 378.1 |
| 3 | (4-hydroxy-4-(pyridin-2-ylmethyl)piperidin-1-yl) (5-methyl-2-(pyridin-4-yl)phenyl)methanone | 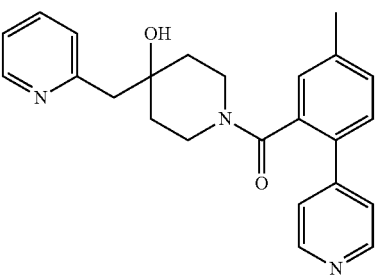 [SMILES: Cc1ccc(-c2ccncc2)c(C(=O)N2CCC(O)(Cc3ccccn3)CC2)c1] | 388.2 |
| 4 | 4-((4-hydroxy-1-(5-methyl-2-(pyridin-4-yl)benzoyl)piperidin-4-yl)methyl)benzonitrile | 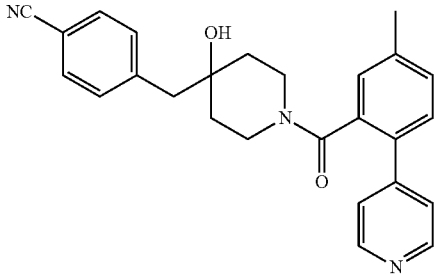 [SMILES: Cc1ccc(-c2ccncc2)c(C(=O)N2CCC(O)(Cc3ccc(C#N)cc3)CC2)c1] | 412.3 |
| 5 | (4-hydroxy-4-isopropylpiperidin-1-yl) (5-methyl-2-(pyridin-4-yl)phenyl)methanone | 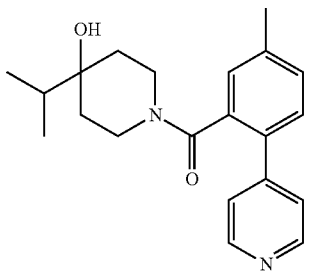 [SMILES: Cc1ccc(-c2ccncc2)c(C(=O)N2CCC(O)(C(C)C)CC2)c1] | 339.2 |
| 6 | (4-benzyl-4-hydroxypiperidin-1-yl) (5-fluoro-2-(pyridin-4-yl)phenyl)methanone | 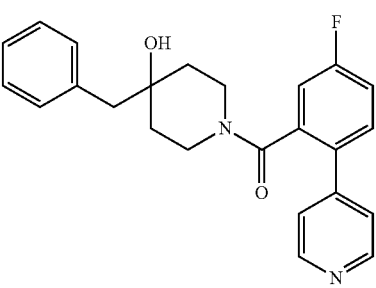 [SMILES: O=C(c1cc(F)ccc1-c1ccncc1)N1CCC(O)(Cc2ccccc2)CC1] | 391.2 |

TABLE 1-continued

| Example No. | IUPAC Name | Chemical Structure | MS |
|---|---|---|---|
| 7 | (4-benzyl-4-hydroxypiperidin-1-yl) (5-chloro-2-(pyridin-4-yl)phenyl)methanone | 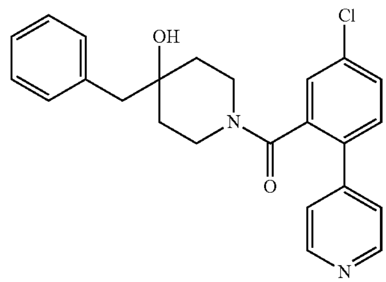 [SMILES: O=C(c1cc(Cl)ccc1-c1ccncc1)N1CCC(O)(Cc2ccccc2)CC1] | 407.1 |
| 8 | (4-hydroxy-4-methylpiperidin-1-yl) (5-methyl-2-(pyridin-4-yl)phenyl)methanone | 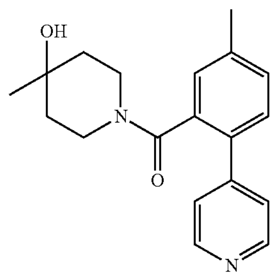 [SMILES: Cc1ccc(-c2ccncc2)c(C(=O)N2CCC(C)(O)CC2)c1] | 311.2 |

TABLE 2

| Example No. | IUPAC Name | Chemical Structure | MS |
|---|---|---|---|
| 9 | (4-benzyl-4-hydroxypiperidin-1-yl) (5-pyridin-4-yl)-1,3-benzodioxol-4-yl)methanone | 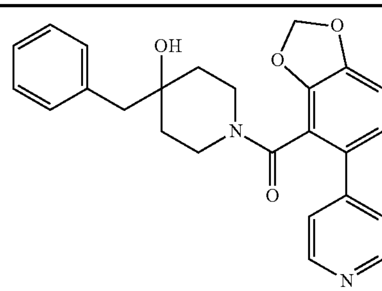 | 417.1 |
| 10 | (4-benzyl-4-hydroxypiperidin-1-yl) (5-methoxy-2-(pyridin-4-yl)phenyl)methanone | 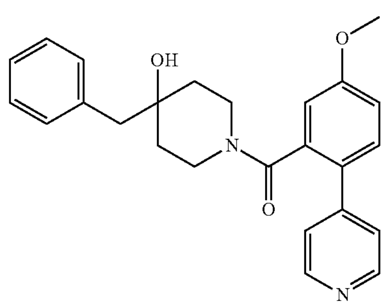 [SMILES: COc1ccc(-c2ccncc2)c(C(=O)N2CCC(O)(Cc3ccccc3)CC2)c1] | 403.2 |
| 11 | (4-benzyl-4-hydroxypiperidin-1-yl) (2-(pyridin-4-yl)phenyl)methanone | 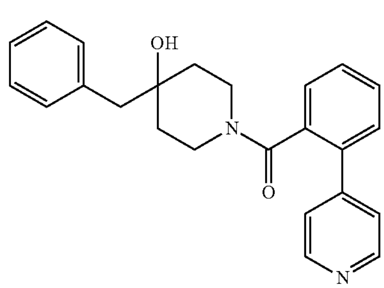 [SMILES: O=C(c1ccccc1-c1ccncc1)N1CCC(O)(Cc2ccccc2)CC1] | 373.2 |

TABLE 2-continued

| Example No. | IUPAC Name | Chemical Structure | MS |
|---|---|---|---|
| 12 | (4-benzyl-4-hydroxypiperidin-1-yl) (4-methyl-2-(pyridin-4-yl)phenyl)methanone | 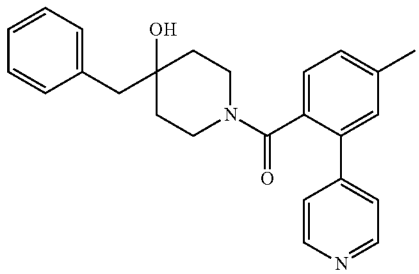 [SMILES: Cc1ccc(C(=O)N2CCC(O)(Cc3ccccc3)CC2)c(-c2ccncc2)c1] | 387.2 |
| 13 | (4-benzyl-4-hydroxypiperidin-1-yl) (4-fluoro-2-(pyridin-4-yl)phenyl)methanone | 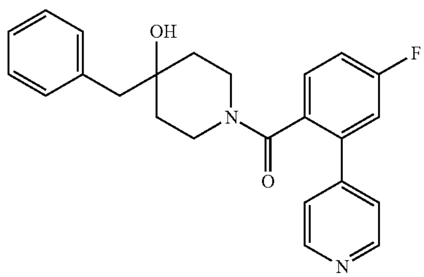 [SMILES: O=C(c1ccc(F)cc1-c1ccncc1)N1CCC(O)(Cc2ccccc2)CC1] | 391.3 |
| 14 | (4-benzyl-4-hydroxypiperidin-1-yl) (2-(pyrimidin-4-yl)phenyl)methanone | 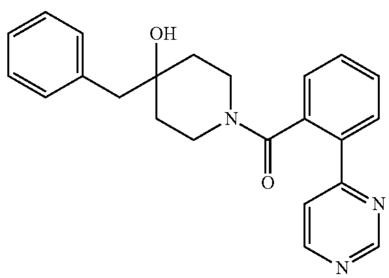 [SMILES: O=C(c1ccccc1-c1ccncn1)N1CCC(O)(Cc2ccccc2)CC1] | 374.2 |
| 15 | (4-benzyl-4-hydroxypiperidin-1-yl) (5-methyl-2-(pyrimidin-4-yl)phenyl)methanone | 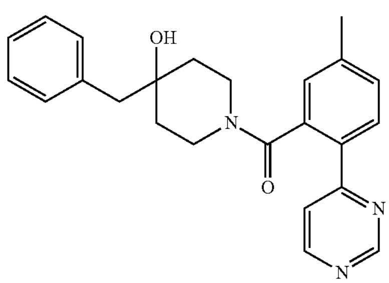 [SMILES: Cc1ccc(-c2ccncn2)c(C(=O)N2CCC(O)(Cc3ccccc3)CC2)c1] | 388.2 |
| 16 | (4-benzyl-4-hydroxypiperidin-1-yl) (5-methyl-3-(pyridin-4-yl)-1H-pyrazol-4-yl)methanone | 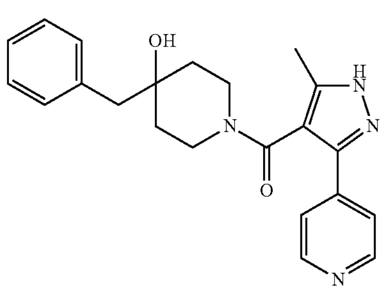 [SMILES: Cc1[nH]nc(-c2ccncc2)c1C(=O)N1CCC(O)(Cc2ccccc2)CC1] | 377.2 |

TABLE 3

| Example No. | IUPAC Name | Chemical Structure | MS |
|---|---|---|---|
| 17 | (4-benzyl-4-hydroxypiperidin-1-yl) (1,5-dimethyl-3-(pyridin-4-yl)-1H-pyrazol-4-yl)methanone | 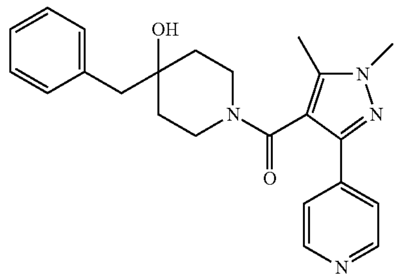 [SMILES: Cc1c(C(=O)N2CCC(O)(Cc3ccccc3)CC2)c(-c2ccncc2)nn1C] | 391.2 |
| 18 | (4-benzyl-4-hydroxypiperidin-1-yl) (3-fluoro-2-(pyridin-4-yl)phenyl)methanone | 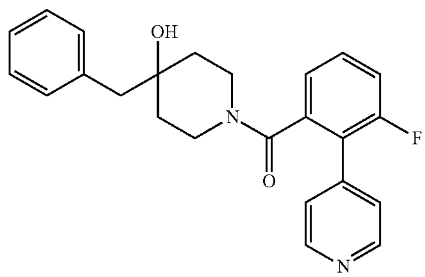 [SMILES: O=C(c1cccc(F)c1-c1ccncc1)N1CCC(O)(Cc2ccccc2)CC1] | 391.2 |
| 19 | (4-benzyl-4-hydroxypiperidin-1-yl) (2-fluoro-6-(pyridin-4-yl)phenyl)methanone | 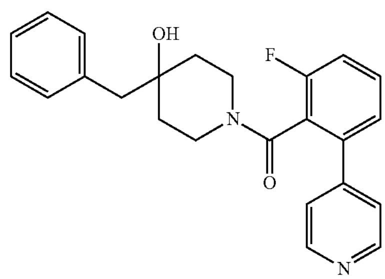 [SMILES: O=C(c1c(F)cccc1-c1ccncc1)N1CCC(O)(Cc2ccccc2)CC1] | 391.2 |
| 20 | (5-fluoro-2-(pyridin-4-yl)phenyl) (4-hydroxy-4-(pyridin-2-ylmethyl)piperidin-1-yl)methanone | 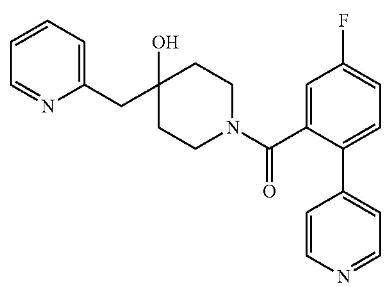 [SMILES: O=C(c1cc(F)ccc1-c1ccncc1)N1CCC(O)(Cc2ccccn2)CC1] | 392.2 |
| 21 | (4-ethyl-4-hydroxypiperidin-1-yl) (5-methyl-2-(pyridin-4-yl)phenyl)methanone | 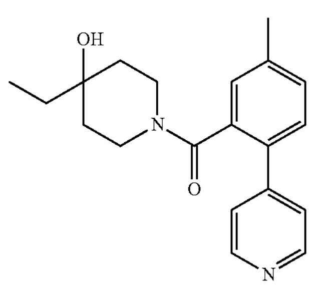 [SMILES: CCC1(O)CCN(C(=O)c2cc(C)ccc2-c2ccncc2)CC1] | 325.2 |

TABLE 3-continued

| Example No. | IUPAC Name | Chemical Structure | MS |
|---|---|---|---|
| 22 | (4-hydroxy-4-propylpiperidin-1-yl) (5-methyl-2-(pyridin-4-yl)phenyl)methanone | 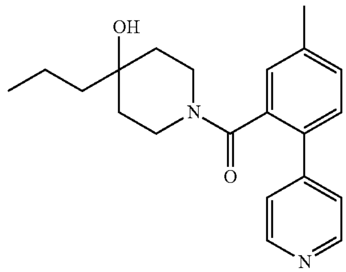 [SMILES: CCCC1(O)CCN(C(=O)c2cc(C)ccc2-c2ccncc2)CC1] | 339.3 |
| 23 | (4-hydroxy-4-(pyridin-2-ylmethyl)piperidin-1-yl) (2-(pyridin-4-yl)phenyl)methanone | 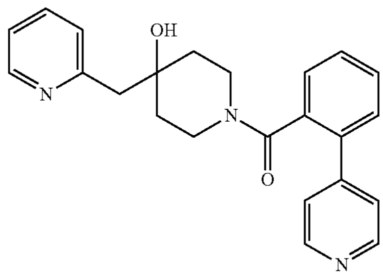 [SMILES: O=C(c1ccccc1-c1ccncc1)N1CCC(O)(Cc2ccccn2)CC1] | 374.2 |
| 24 | (4-hydroxy-4-(pyridin-2-ylmethyl)piperidin-1-yl) (5-(pyridin-4-yl)-1,3-thiazol-4-yl)methanone | 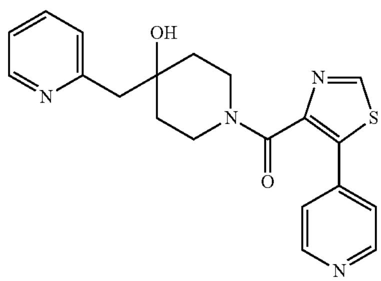 [SMILES: O=C(c1ncsc1-c1ccncc1)N1CCC(O)(Cc2ccccn2)CC1] | 381.1 |

TABLE 4

| Example No. | IUPAC Name | Chemical Structure | MS |
|---|---|---|---|
| 25 | (4-benzyl-4-hydroxypiperidin-1-yl) (5-(pyridin-4-yl)-1,3-thiazol-4-yl)methanone | 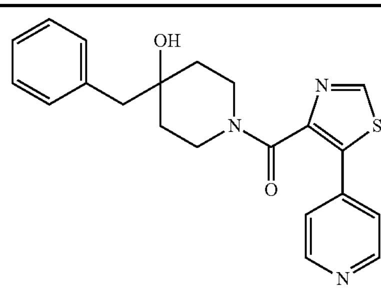 | 380.2 |
| 26 | (4-benzyl-4-hydroxypiperidin-1-yl) (4-(pyridin-4-yl)-1,3-thiazol-5-yl)methanone | 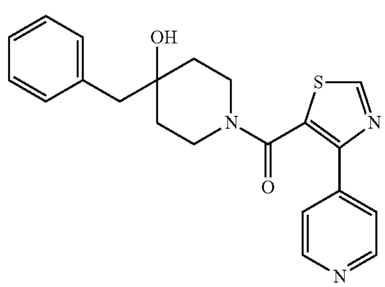 [SMILES: O=C(c1scnc1-c1ccncc1)N1CCC(O)(Cc2ccccc2)CC1] | 380.2 |

TABLE 4-continued

| Example No. | IUPAC Name | Chemical Structure | MS |
|---|---|---|---|
| 27 | (4-benzyl-4-hydroxypiperidin-1-yl) (3-methyl-2-(pyridin-4-yl)phenyl)methanone | 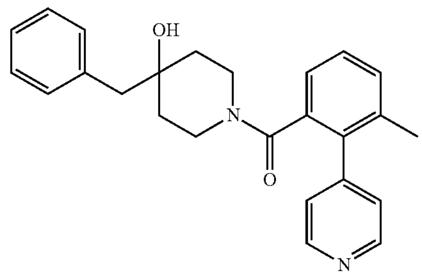 [SMILES: Cc1cccc(C(=O)N2CCC(O)(Cc3ccccc3)CC2)c1-c1ccncc1] | 387.2 |
| 28 | (4-benzyl-4-hydroxypiperidin-1-yl) (2-(3-fluoropyridin-4-yl)phenyl)methanone | 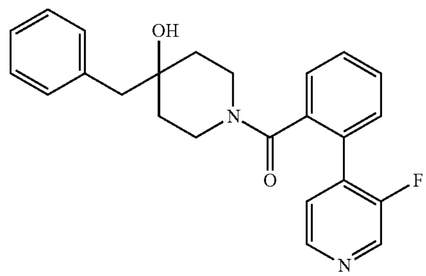 [SMILES: O=C(c1ccccc1-c1ccncc1F)N1CCC(O)(Cc2ccccc2)CC1] | 391.2 |
| 29 | (2-(3-fluoropyridin-4-yl)phenyl) (4-hydroxy-4-(pyridin-2-ylmethyl)piperidin-1-yl)methanone | 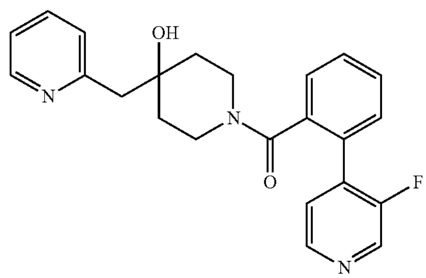 [SMILES: O=C(c1ccccc1-c1ccncc1F)N1CCC(O)(Cc2ccccn2)CC1] | 392.1 |
| 30 | (4-fluoro-2-(pyridin-4-yl)phenyl) (4-hydroxy-4-(pyridin-2-ylmethyl)piperidin-1-yl)methanone | 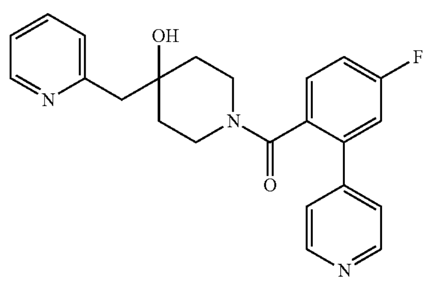 [SMILES: O=C(c1ccc(F)cc1-c1ccncc1)N1CCC(O)(Cc2ccccn2)CC1] | 392.1 |
| 31 | (4-benzyl-4-hydroxypiperidin-1-yl) (2-methyl-5-(pyridin-4-yl)-1,3-thiazol-4-yl)methanone | 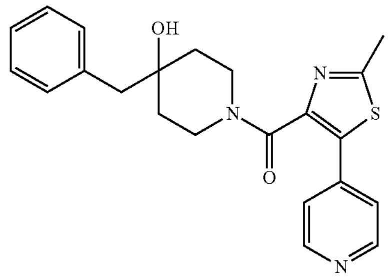 [SMILES: Cc1nc(C(=O)N2CCC(O)(Cc3ccccc3)CC2)c(-c2ccncc2)s1] | 394.2 |

TABLE 4-continued

| Example No. | IUPAC Name | Chemical Structure | MS |
|---|---|---|---|
| 32 | (4-benzyl-4-hydroxypiperidin-1-yl) (1-methyl-4-(pyridin-4-yl)-1H-pyrazol-5-yl)methanone | 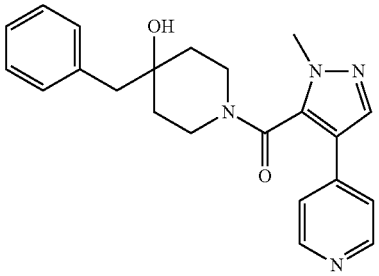 [SMILES: Cn1ncc(-c2ccncc2)c1C(=O)N1CCC(O)(Cc2ccccc2)CC1] | 377.2 |

TABLE 5

| Example No. | IUPAC Name | Chemical Structure | MS |
|---|---|---|---|
| 33 | (4-hydroxy-4-(pyridin-2-ylmethyl)piperidin-1-yl) (1-methyl-4-(pyridin-4-yl)-1H-pyrazol-5-yl)methanone | 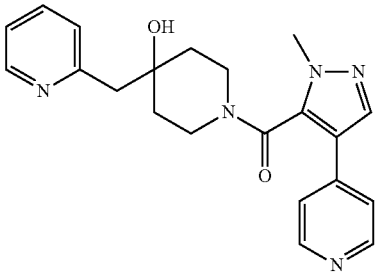 [SMILES: Cn1ncc(-c2ccncc2)c1C(=O)N1CCC(O)(Cc2ccccn2)CC1] | 378.2 |
| 34 | (4-hydroxy-4-(pyridin-2-ylmethyl)piperidin-1-yl) (2-(pyrimidin-4-yl)phenyl)methanone | 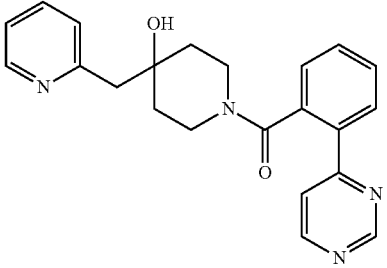 [SMILES: O=C(c1ccccc1-c1ccncn1)N1CCC(O)(Cc2ccccn2)CC1] | 375.2 |
| 35 | (4-hydroxy-4-(pyridin-2-ylmethyl)piperidin-1-yl) (2-methyl-5-(pyridin-4-yl)-1,3-thiazol-4-yl)methanone | 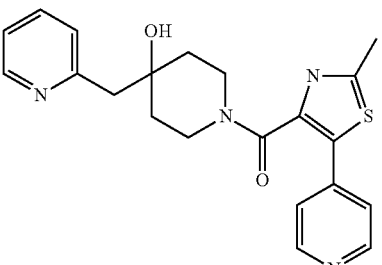 | 395.2 |
| 36 | (4-benzyl-4-hydroxypiperidin-1-yl) (2-methyl-6-(pyridin-4-yl)phenyl)methanone | 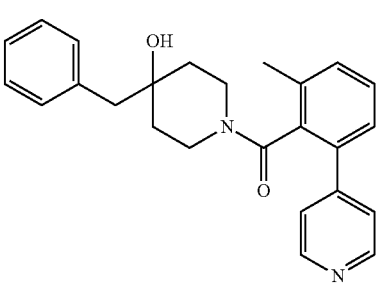 [SMILES: Cc1cccc(-c2ccncc2)c1C(=O)N1CCC(O)(Cc2ccccc2)CC1] | 387.2 |

TABLE 5-continued

| Example No. | IUPAC Name | Chemical Structure | MS |
|---|---|---|---|
| 37 | (4-(4-fluorobenzyl)-4-hydroxypiperidin-1-yl) (5-methyl-2-(pyridin-4-yl)phenyl)methanone | 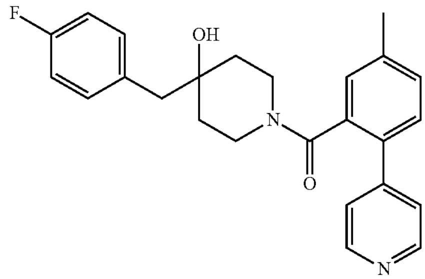 [SMILES: Cc1ccc(-c2ccncc2)c(C(=O)N2CCC(O)(Cc3ccc(F)cc3)CC2)c1] | 405.2 |
| 38 | (4-(4-fluorobenzyl)-4-hydroxypiperidin-1-yl) (2-(pyridin-4-yl)phenyl)methanone | 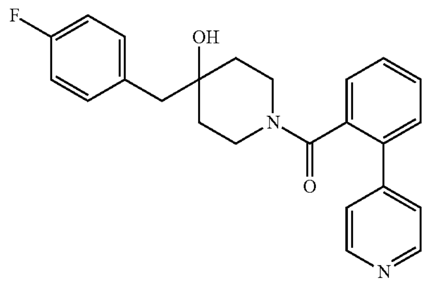 [SMILES: O=C(c1ccccc1-c1ccncc1)N1CCC(O)(Cc2ccc(F)cc2)CC1] | 391.2 |
| 39 | (4-(4,5-dihydro-1,3-thiazol-2-ylmethyl)-4-hydroxypiperidin-1-yl) (5-methyl-2-(pyridin-4-yl)phenyl)methanone | 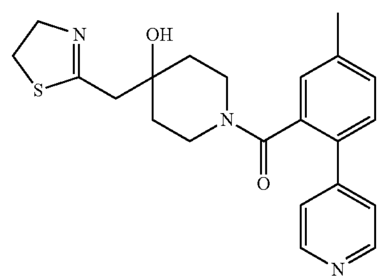 [SMILES: Cc1ccc(-c2ccncc2)c(C(=O)N2CCC(O)(CC3=NCCS3)CC2)c1] | 396.2 |
| 40 | (4-(4,5-dihydro-1,3-thiazol-2-ylmethyl)-4-hydroxypiperidin-1-yl) (2-(pyridin-4-yl)phenyl)methanone | 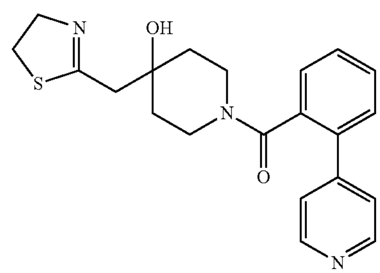 [SMILES: O=C(c1ccccc1-c1ccncc1)N1CCC(O)(CC2=NCCS2)CC1] | 382.1 |

TABLE 6

| Example No. | IUPAC Name | Chemical Structure | MS |
|---|---|---|---|
| 41 | (4-benzyl-4-hydroxypiperidin-1-yl) (5-(pyridin-4-yl)-3-(trifluoromethyl)-1H-pyrazol-4-yl)methanone | 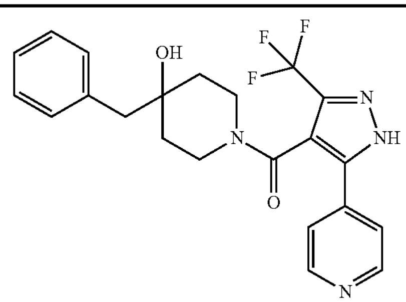 | 431.1 |

TABLE 6-continued

| Example No. | IUPAC Name | Chemical Structure | MS |
|---|---|---|---|
| 42 | (4-benzyl-4-hydroxypiperidin-1-yl) (1-tert-butyl-5-(pyridin-4-yl)-3-(trifluoromethyl)-1H-pyrazol-4-yl)methanone | 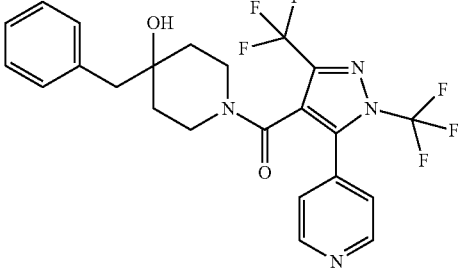 | 487.2 |
| 43 | (4-benzyl-4-hydroxypiperidin-1-yl) (2-methyl-4-(pyridin-4-yl)-1,3-thiazol-5-yl)methanone | 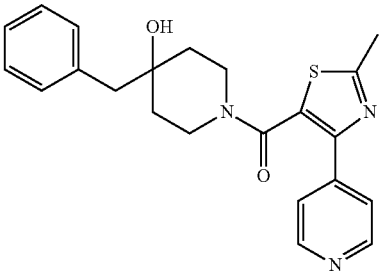 | 394.2 |
| 44 | (4-benzyl-4-hydroxypiperidin-1-yl) (2,4'-bipyridin-3-yl)methanone | 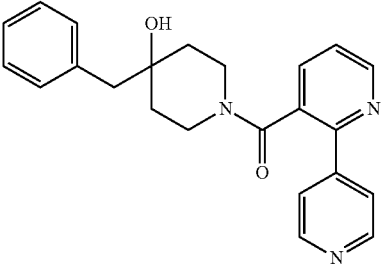 [SMILES: O=C(c1cccnc1-c1ccncc1)N1CCC(O)(Cc2ccccc2)CC1] | 374.2 |
| 45 | ((7-endo)-7-benzyl-7-hydroxy-3-oxa-9-azabicyclo[3.3.1]non-9-yl) (2-(pyridin-4-yl)phenyl)methanone | 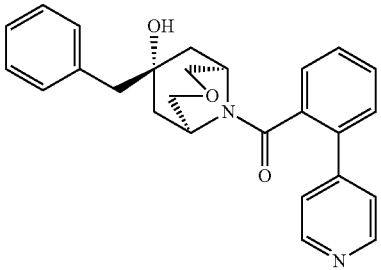 [SMILES: O=C(c1ccccc1-c1ccncc1)N1[C@@H]2COC[C@H]1C[C@](O)(Cc1ccccc1)C2] | 415.2 |
| 46 | (4-benzyl-4-hydroxypiperidin-1-yl) (4-fluoro-2-(pyrimidin-4-yl)phenyl)methanone | 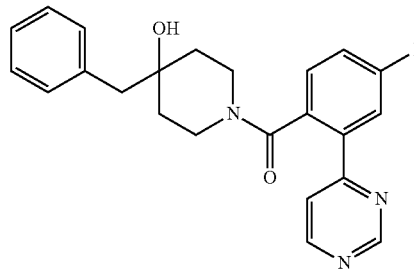 | 392.2 |

TABLE 6-continued

| Example No. | IUPAC Name | Chemical Structure | MS |
|---|---|---|---|
| 47 | (4-(4-fluorobenzyl)-4-hydroxypiperidin-1-yl) (4-fluoro-2-(pyrimidin-4-yl)phenyl)methanone | 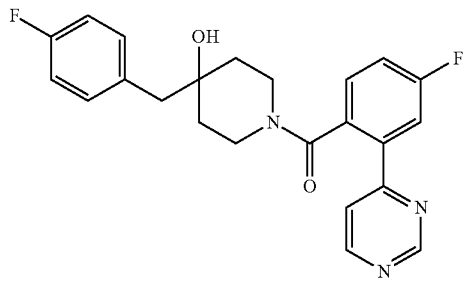 [SMILES: O=C(c1ccc(F)cc1-c1ccncn1)N1CCC(O)(Cc2ccc(F)cc2)CC1] | 410.2 |
| 48 | (4-(4-fluorobenzyl)-4-hydroxypiperidin-1-yl) (2-(pyrimidin-4-yl)phenyl)methanone | 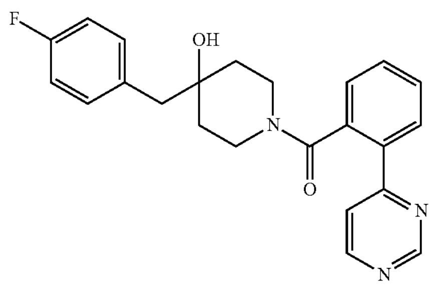 [SMILES: O=C(c1ccccc1-c1ccncn1)N1CCC(O)(Cc2ccc(F)cc2)CC1] | 392.2 |

TABLE 7

| Example No. | IUPAC Name | Chemical Structure | MS |
|---|---|---|---|
| 49 | (4-(2-fluorobenzyl)-4-hydroxypiperidin-1-yl) (2-(pyridin-4-yl)phenyl)methanone | 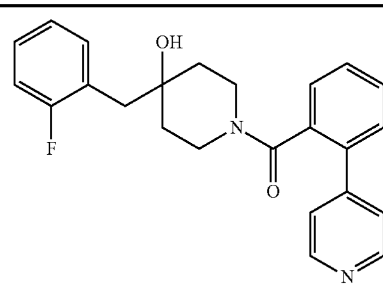 | 391.2 |
| 50 | (4-(3-fluorobenzyl)-4-hydroxypiperidin-1-yl) (2-(pyridin-4-yl)phenyl)methanone | 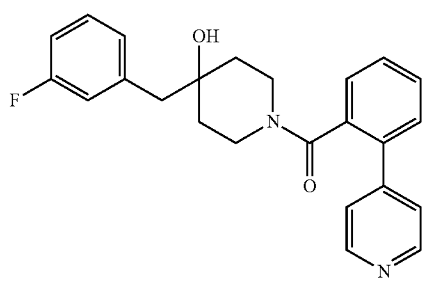 [SMILES: O=C(c1ccccc1-c1ccncc1)N1CCC(O)(Cc2cccc(F)c2)CC1] | 391.2 |
| 51 | (4-(3-fluorobenzyl)-4-hydroxypiperidin-1-yl) (2-(pyrimidin-4-yl)phenyl)methanone | 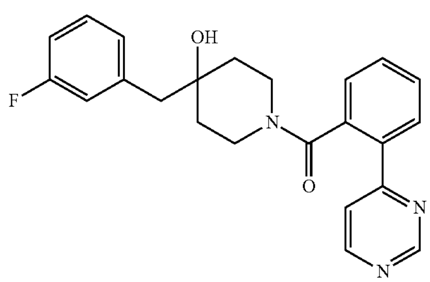 [SMILES: O=C(c1ccccc1-c1ccncn1)N1CCC(O)(Cc2cccc(F)c2)CC1] | 392.1 |

TABLE 7-continued

| Example No. | IUPAC Name | Chemical Structure | MS |
|---|---|---|---|
| 52 | (4-(2-fluorobenzyl)-4-hydroxypiperidin-1-yl) (2-(pyrimidin-4-yl)phenyl)methanone | 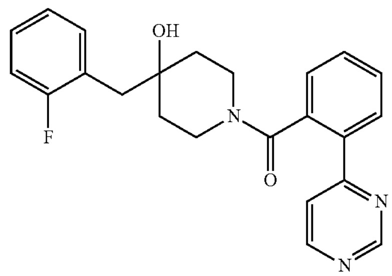 [SMILES: O=C(c1ccccc1-c1ccncn1)N1CCC(O)(Cc2ccccc2F)CC1] | 392.2 |
| 53 | (4-benzyl-4-hydroxypiperidin-1-yl) (4,5-difluoro-2-(pyridin-4-yl)phenyl)methanone | 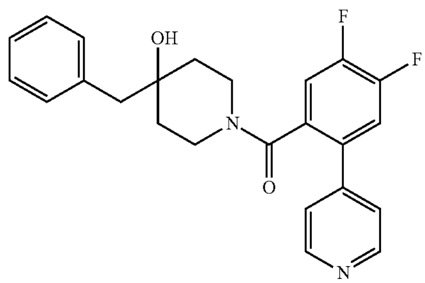 [SMILES: O=C(c1cc(F)c(F)cc1-c1ccncc1)N1CCC(O)(Cc2ccccc2)CC1] | 409.1 |
| 54 | (4-benzyl-4-hydroxypiperidin-1-yl) (2-(pyrimidin-4-yl)pyridin-3-yl)methanone | 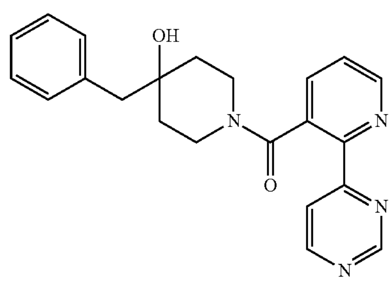 | 375.2 |
| 55 | (4-benzyl-4-hydroxypiperidin-1-yl) (4,5-difluoro-2-(pyrimidin-4-yl)phenyl)methanone | 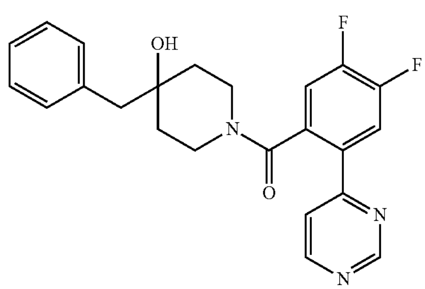 [SMILES: O=C(c1cc(F)c(F)cc1-c1ccncn1)N1CCC(O)(Cc2ccccc2)CC1] | 410.1 |
| 56 | (4,5-difluoro-2-(pyrimidin-4-yl)phenyl) (4-hydroxy-4-(pyridin-2-ylmethyl)piperidin-1-yl)methanone | 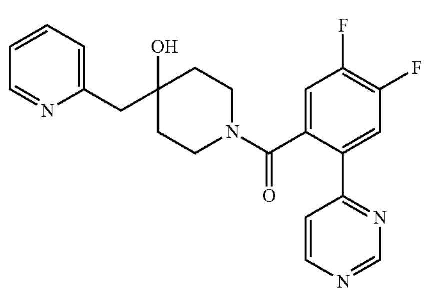 [SMILES: O=C(c1cc(F)c(F)cc1-c1ccncn1)N1CCC(O)(Cc2ccccn2)CC1] | 411.2 |

TABLE 8

| Example No. | IUPAC Name | Chemical Structure | MS |
|---|---|---|---|
| 57 | (4-benzyl-4-hydroxypiperidin-1-yl) (5-fluoro-2-(pyrimidin-4-yl)phenyl)methanone | 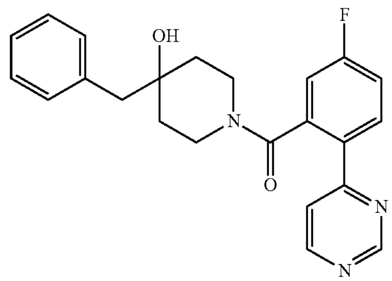 [SMILES: O=C(c1cc(F)ccc1-c1ccncn1)N1CCC(O)(Cc2ccccc2)CC1] | 392.1 |
| 58 | (5-fluoro-2-(pyrimidin-4-yl)phenyl) (4-hydroxy-4-(pyridin-2-ylmethyl)piperidin-1-yl)methanone | 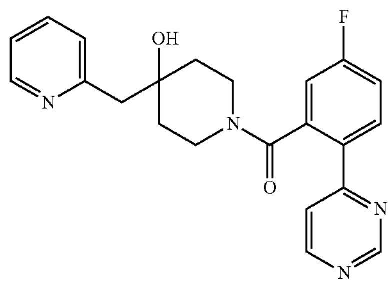 [SMILES: O=C(c1cc(F)ccc1-c1ccncn1)N1CCC(O)(Cc2ccccn2)CC1] | 393.2 |
| 59 | (4-benzyl-4-methoxypiperidin-1-yl) (5-methyl-2-(pyridin-4-yl)phenyl)methanone | 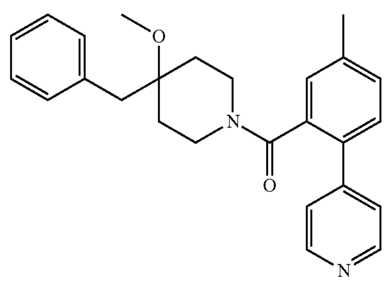 [SMILES: COC1(Cc2ccccc2)CCN(C(=O)c2cc(C)ccc2-c2ccncc2)CC1] | 401.2 |
| 60 | (4-benzyl-4-hydroxypiperidin-1-yl) (2-methyl-4-(pyrimidin-4-yl)-1,3-thiazol-5-yl)methanone | 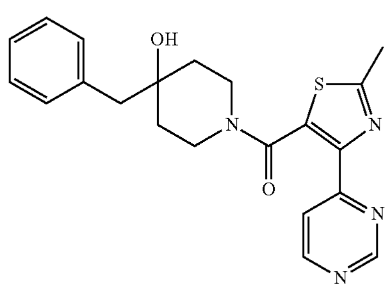 [SMILES: Cc1nc(-c2ccncn2)c(C(=O)N2CCC(O)(Cc3ccccc3)CC2)s1] | 395.2 |
| 61 | (4-hydroxy-4-(pyridin-2-ylmethyl)piperidin-1-yl) (2-methyl-4-(pyrimidin-4-yl)-1,3-thiazol-5-yl)methanone | 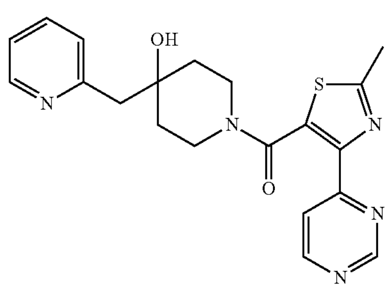 [SMILES: Cc1nc(-c2ccncn2)c(C(=O)N2CCC(O)(Cc3ccccn3)CC2)s1] | 396.2 |

TABLE 8-continued

| Example No. | IUPAC Name | Chemical Structure | MS |
|---|---|---|---|
| 62 | (4-(4-fluorobenzyl)-4-hydroxypiperidin-1-yl) (2-methyl-4-(pyrimidin-4-yl)-1,3-thiazol-5-yl)methanone | 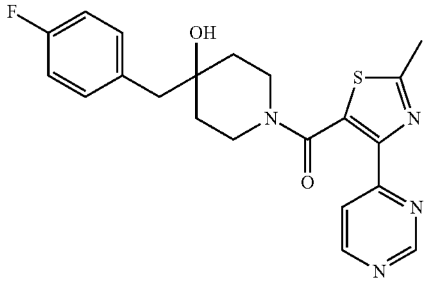 [SMILES: Cc1nc(-c2ccncn2)c(C(=O)N2CCC(O)(Cc3ccc(F)cc3)CC2)s1] | 413.1 |
| 63 | (4-fluoro-2-(pyrimidin-4-yl)phenyl) (4-hydroxy-4-(pyridin-2-ylmethyl)piperidin-1-yl)methanone | 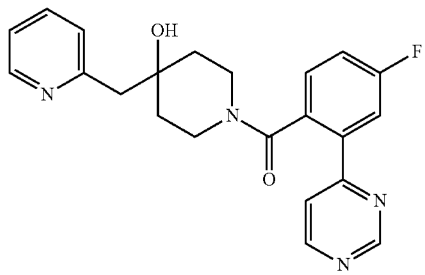 | 393.2 |
| 64 | 2,4'-bipyridin-3-yl (4-(2-fluorobenzyl)-4-hydroxypiperidin-1-yl)methanone | 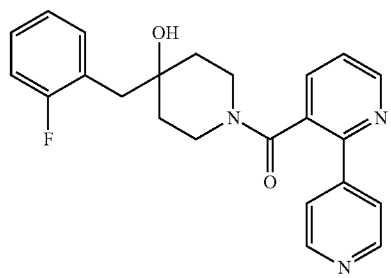 [SMILES: O=C(c1cccnc1-c1ccncc1)N1CCC(O)(Cc2ccccc2F)CC1] | 392.1 |

TABLE 9

| Example No. | IUPAC Name | Chemical Structure | MS |
|---|---|---|---|
| 65 | 2,4'-bipyridin-3-yl (4-(3-fluorobenzyl)-4-hydroxypiperidin-1-yl)methanone | 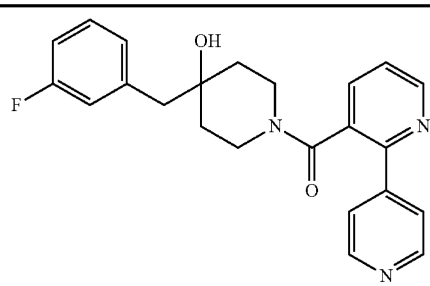 | 392.1 |
| 66 | 2,4'-bipyridin-3-yl (4-hydroxy-4-(pyridin-2-ylmethyl)piperidin-1-yl)methanone | 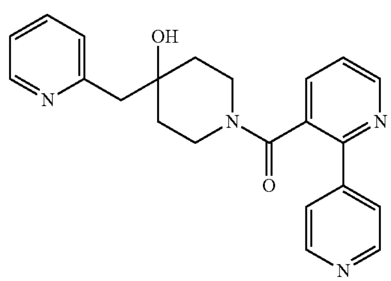 [SMILES: O=C(c1cccnc1-c1ccncc1)N1CCC(O)(Cc2ccccn2)CC1] | 375.2 |

TABLE 9-continued

| Example No. | IUPAC Name | Chemical Structure | MS |
|---|---|---|---|
| 67 | 2,4'-bipyridin-3-yl (4-(4-fluorobenzyl)-4-hydroxypiperidin-1-yl)methanone | 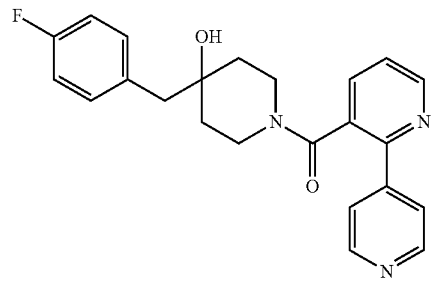 [SMILES: O=C(c1cccnc1-c1ccncc1)N1CCC(O)(Cc2ccc(F)cc2)CC1] | 392.1 |
| 68 | 4-((4-hydroxy-1-(2-(pyrimidin-4-yl)benzoyl)piperidin-4-yl)methyl)benzonitrile | 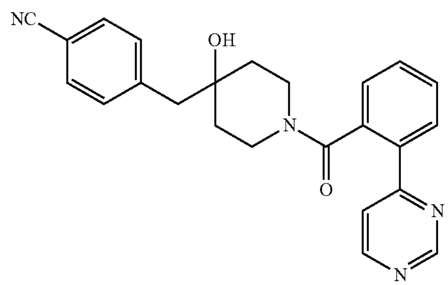 [SMILES: N#Cc1ccc(CC2(O)CCN(C(=O)c3ccccc3-c3ccncn3)CC2)cc1] | 399.2 |
| 69 | 4-((1-(4-fluoro-2-(pyrimidin-4-yl)benzoyl)-4-hydroxypiperidin-4-yl)methyl)benzonitrile | 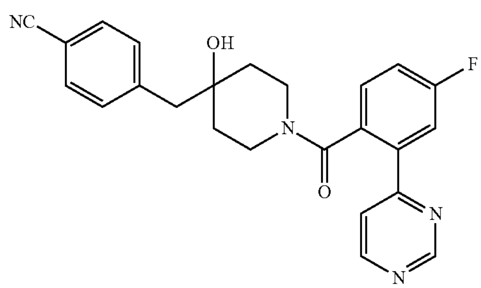 [SMILES: N#Cc1ccc(CC2(O)CCN(C(=O)c3ccc(F)cc3-c3ccncn3)CC2)cc1] | 417.1 |
| 70 | 4-((1-(2,4'-bipyridin-3-ylcarbonyl)-4-hydroxypiperidin-4-yl)methyl)benzonitrile | 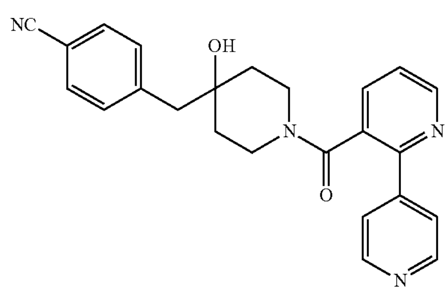 [SMILES: N#Cc1ccc(CC2(O)CCN(C(=O)c3cccnc3-c3ccncc3)CC2)cc1] | 399.1 |
| 71 | 2-((1-(2,4'-bipyridin-3-ylcarbonyl)-4-hydroxypiperidin-4-yl)methyl)benzonitrile | 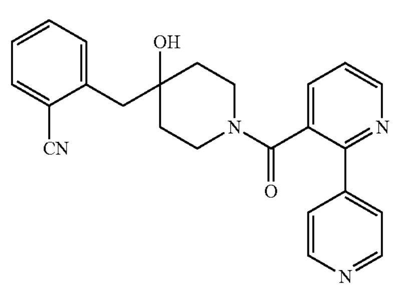 [SMILES: N#Cc1ccccc1CC1(O)CCN(C(=O)c2cccnc2-c2ccncc2)CC1] | 399.2 |

TABLE 9-continued

| Example No. | IUPAC Name | Chemical Structure | MS |
|---|---|---|---|
| 72 | 3-((1-(2,4'-bipyridin-3-ylcarbonyl)-4-hydroxypiperidin-4-yl)methyl)benzonitrile | 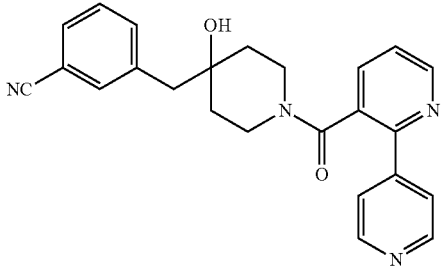 [SMILES: N#Cc1cccc(CC2(O)CCN(C(=O)c3cccnc3-c3ccncc3)CC2)c1] | 399.1 |

TABLE 10

| Example No. | IUPAC Name | Chemical Structure | MS |
|---|---|---|---|
| 73 | 4-((4-hydroxy-1-((2-methyl-4-(pyrimidin-4-yl)-1,3-thiazol-5-yl)carbonyl)piperidin-4-yl)methyl)benzonitrile | 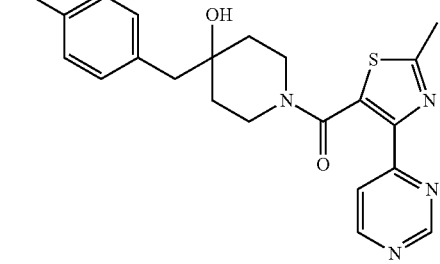 | 420.1 |
| 74 | 2-((1-(4-fluoro-2-(pyrimidin-4-yl)benzoyl)-4-hydroxypiperidin-4-yl)methyl)benzonitrile | 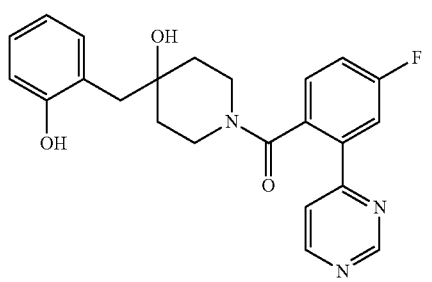 [SMILES: O=C(c1ccc(F)cc1-c1ccncn1)N1CCC(O)(Cc2ccccc2O)CC1] | 417.2 |
| 75 | 3-((1-(4-fluoro-2-(pyrimidin-4-yl)benzoyl)-4-hydroxypiperidin-4-yl)methyl)benzonitrile | 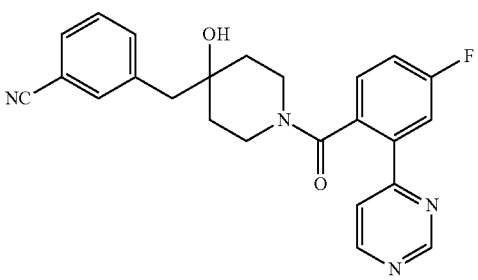 [SMILES: N#Cc1cccc(CC2(O)CCN(C(=O)c3ccc(F)cc3-c3ccncn3)CC2)c1] | 417.1 |
| 76 | (4-benzyl-4-hydroxypiperidin-1-yl) (3-(pyridin-4-yl)pyrazin-2-yl)methanone | 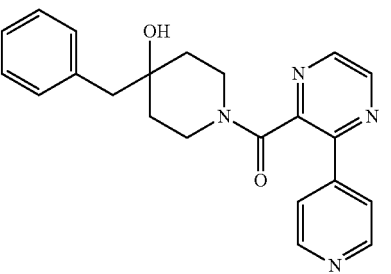 [SMILES: O=C(c1nccnc1-c1ccncc1)N1CCC(O)(Cc2ccccc2)CC1] | 375.2 |

TABLE 10-continued

| Example No. | IUPAC Name | Chemical Structure | MS |
|---|---|---|---|
| 77 | 2-((1-(5-fluoro-2-(pyrimidin-4-yl)benzoyl)-4-hydroxypiperidin-4-yl)methyl)benzonitrile | 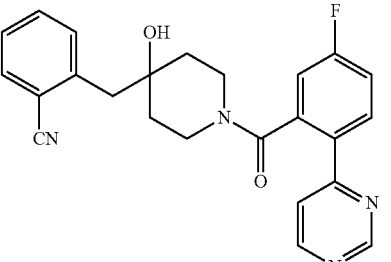 | 417.1 |
| 78 | 3-((1-(5-fluoro-2-(pyrimidin-4-yl)benzoyl)-4-hydroxypiperidin-4-yl)methyl)benzonitrile | 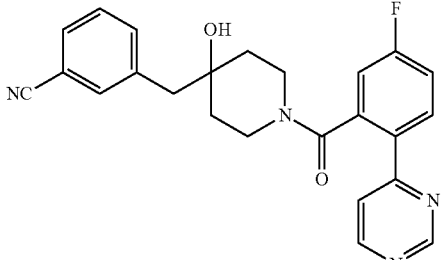 | 417.1 |
| 79 | 4-((1-(5-fluoro-2-(pyrimidin-4-yl)benzoyl)-4-hydroxypiperidin-4-yl)methyl)benzonitrile | 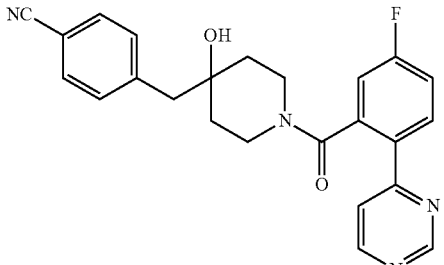 | 417.1 |
| 80 | (4-(4-fluorobenzyl)-4-hydroxypiperidin-1-yl) (5-fluoro-2-(pyrimidin-4-yl)phenyl)methanone | 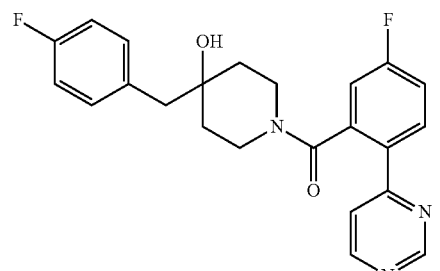 | 410.2 |

TABLE 11

| Example No. | IUPAC Name | Chemical Structure | MS |
|---|---|---|---|
| 81 | (4-(4-fluorobenzyl)-4-hydroxypiperdin-1-yl) (3-(pyridin-4-yl)pyrazin-2-yl)methanone | 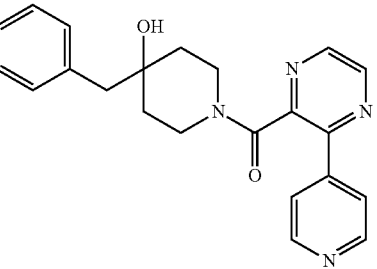 | 393.2 |

TABLE 11-continued

| Example No. | IUPAC Name | Chemical Structure | MS |
|---|---|---|---|
| 82 | (4-benzyl-4-hydroxypiperidin-1-yl) (2-(1,3-oxazol-5-yl)phenyl)methanone | 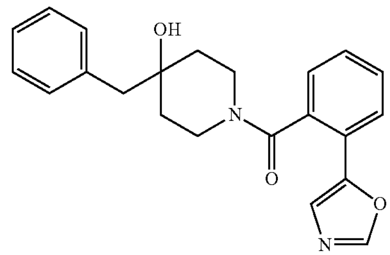 [SMILES: O=C(c1ccccc1-c1cnco1)N1CCC(O)(Cc2ccccc2)CC1] | 363.2 |
| 83 | (4-benzyl-4-hydroxypiperidin-1-yl) (4-(1-methyl-1H-pyrazol-4-yl)pyridin-3-yl)methanone | 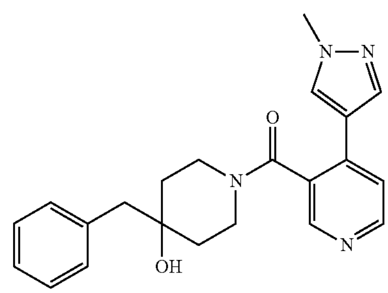 [SMILES: Cn1cc(-c2ccncc2C(=O)N2CCC(O)(Cc3ccccc3)CC2)cn1] | 377.2 |
| 84 | (4-benzyl-4-hydroxypiperidin-1-yl) (3,4'-bipyridin-3'-yl)methanone | 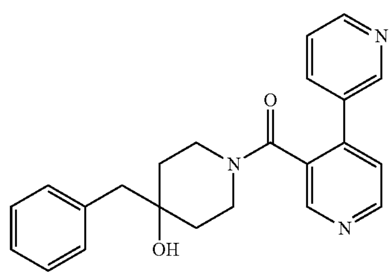 [SMILES: O=C(c1cnccc1-c1cccnc1)N1CCC(O)(Cc2ccccc2)CC1] | 374.2 |
| 85 | (4-benzyl-4-hydroxypiperidin-1-yl) (2-(pyridazin-4-yl)phenyl)methanone | 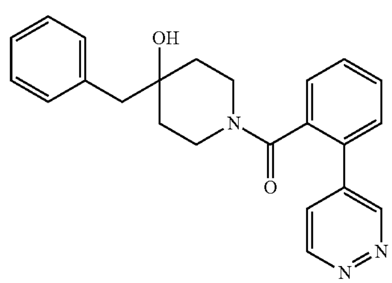 [SMILES: O=C(c1ccccc1-c1ccnnc1)N1CCC(O)(Cc2ccccc2)CC1] | 374.2 |
| 86 | 2,4'-bipyridin-3-yl (4-(3,4-difluorobenzyl)-4-hydroxypiperidin-1-yl)methanone | 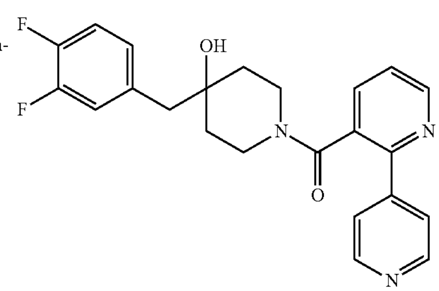 | 410.2 |

TABLE 11-continued

| Example No. | IUPAC Name | Chemical Structure | MS |
|---|---|---|---|
| 87 | 2,4'-bipyridin-3-yl (4-(2,4-difluorobenzyl)-4-hydroxypiperidin-1-yl)methanone | 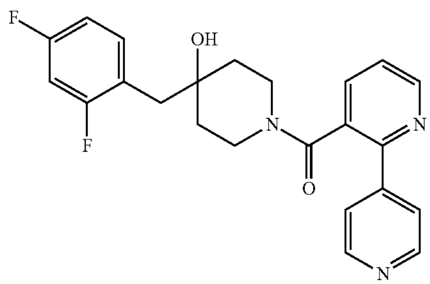 [SMILES: O=C(c1cccnc1-c1ccncc1)N1CCC(O)(Cc2ccc(F)cc2F)CC1] | 410.2 |
| 88 | (4-(3,4-difluorobenzyl)-4-hydroxypiperidin-1-yl) (2-methyl-4-(pyrimidin-4-yl)-1,3-thiazol-5-yl)methanone | 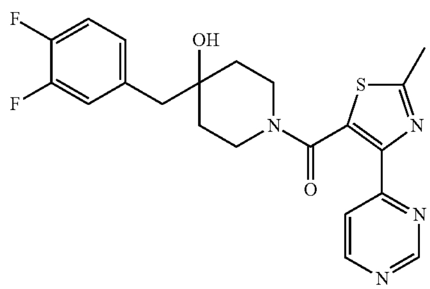 [SMILES: Cc1nc(-c2ccncn2)c(C(=O)N2CCC(O)(Cc3ccc(F)c(F)c3)CC2)s1] | 431.1 |

TABLE 12

| Example No. | IUPAC Name | Chemical Structure | MS |
|---|---|---|---|
| 89 | (4-(2,4-difluorobenzyl)-4-hydroxypiperidin-1-yl) (2-methyl-4-(pyrimidin-4-yl)-1,3-thiazol-5-yl)methanone | 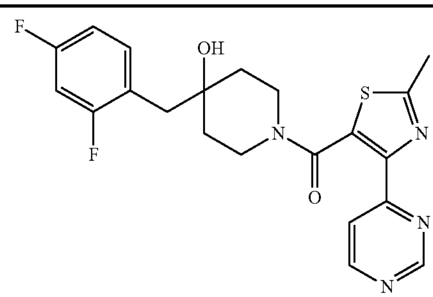 | 431.0 |
| 90 | (4-(2,3-difluorobenzyl)-4-hydroxypiperidin-1-yl) (2-methyl-4-(pyrimidin-4-yl)-1,3-thiazol-5-yl)methanone | 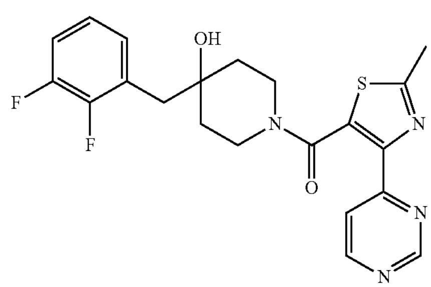 [SMILES: Cc1nc(-c2ccncn2)c(C(=O)N2CCC(O)(Cc3cccc(F)c3F)CC2)s1] | 431.0 |
| 91 | 4-((4-hydroxy-1-((2-(pyrimidin-4-yl)pyridin-3-yl)carbonyl)piperidin-4-yl)methyl)benzonitrile | 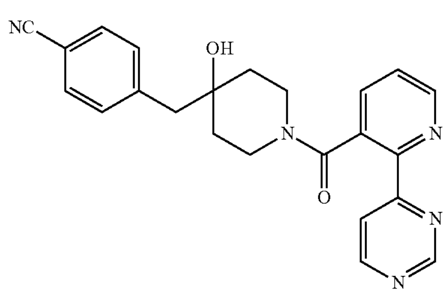 [SMILES: N#Cc1ccc(CC2(O)CCN(C(=O)c3cccnc3-c3ccncn3)CC2)cc1] | 400.2 |

TABLE 12-continued

| Example No. | IUPAC Name | Chemical Structure | MS |
|---|---|---|---|
| 92 | (4-(4-fluorobenzyl)-4-hydroxypiperidin-1-yl) (2-(pyrimidin-4-yl)pyridin-3-yl)methanone | 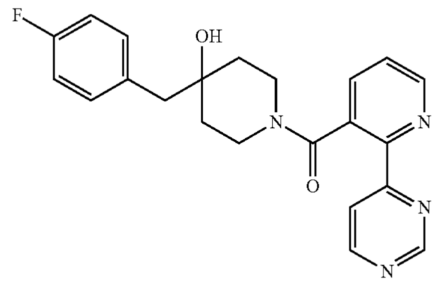 [SMILES: O=C(c1cccnc1-c1ccncn1)N1CCC(O)(Cc2ccc(F)cc2)CC1] | 393.2 |
| 93 | 2,4'-bipyridin-3-yl (4-(2,3-difluorobenzyl)-4-hydroxypiperidin-1-yl)methanone | 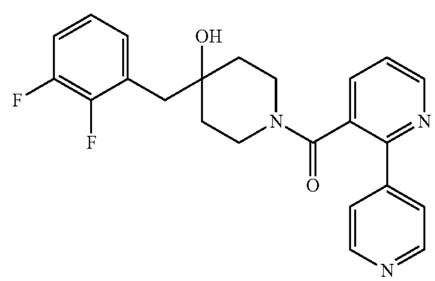 [SMILES: O=C(c1cccnc1-c1ccncc1)N1CCC(O)(Cc2cccc(F)c2F)CC1] | 410.1 |
| 94 | 4-((4-hydroxy-1-(2-(pyridin-4-yl)benzoyl)piperidin-4-yl)methyl)benzonitrile | 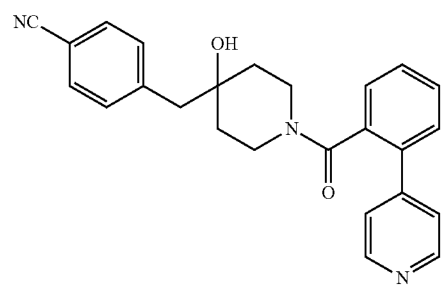 [SMILES: N#Cc1ccc(CC2(O)CCN(C(=O)c3ccccc3-c3ccncc3)CC2)cc1] | 398.2 |
| 95 | 4-((1-(5-fluoro-2-(pyridin-4-yl)benzoyl)-4-hydroxypiperidin-4-yl)methyl)benzonitrile | 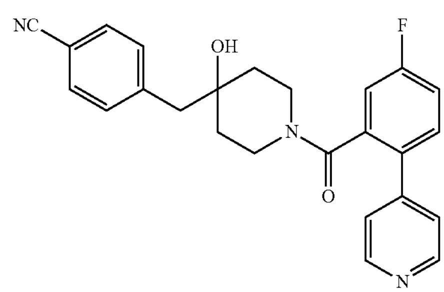 | 416.1 |
| 96 | 4-((1-(4-fluroro-2-(pyridin-4-yl)benzoyl)-4-hydroxypiperidin-4-yl)methyl)benzonitrile | 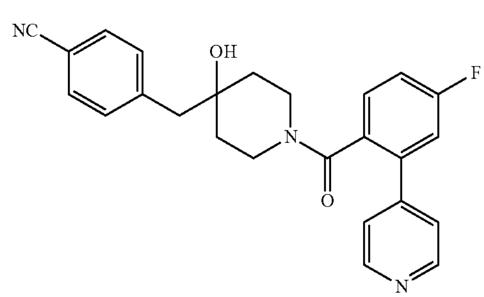 [SMILES: N#Cc1ccc(CC2(O)CCN(C(=O)c3ccc(F)cc3-c3ccncc3)CC2)cc1] | 416.1 |

TABLE 13

| Example No. | IUPAC Name | Chemical Structure | MS |
|---|---|---|---|
| 97 | 2,4'-bipyridin-3-yl (4-hydroxy-4-(4-methoxybenzyl)piperidin-1-yl)methanone | 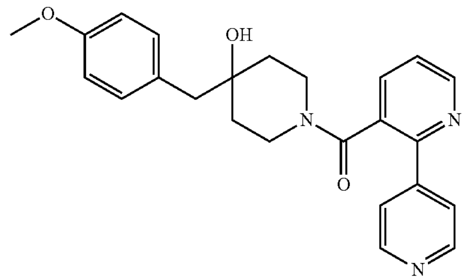 [SMILES: COc1ccc(CC2(O)CCN(C(=O)c3cccnc3-c3ccncc3)CC2)cc1] | 404.1 |
| 98 | 2,4'-bipyridin-3-yl (4-hydroxy-4-(4-(trifluoromethoxy)benzyl)piperidin-1-yl)methanone | 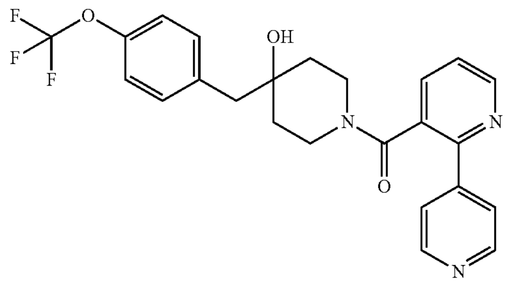 [SMILES: O=C(c1cccnc1-c1ccncc1)N1CCC(O)(Cc2ccc(OC(F)(F)F)cc2)CC1] | 458.1 |
| 99 | (4-(4-fluorobenzyl)-4-hydroxypiperidin-1-yl) (1-methyl-4-(pyridin-4-yl)-1H-pyrazol-5-yl)methanone | 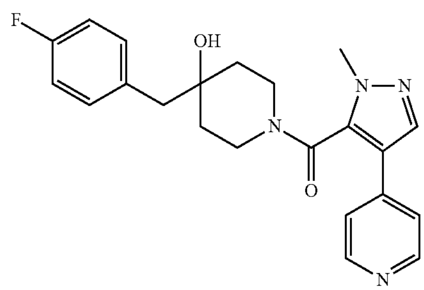 [SMILES: Cn1ncc(-c2ccncc2)c1C(=O)N1CCC(O)(Cc2ccc(F)cc2)CC1] | 395.2 |

TABLE 14

| Example No. | IUPAC Name | Chemical Structure | MS |
|---|---|---|---|
| 100 | (4-(4-fluorobenzyl)-4-hydroxypiperidin-1-yl) (2-(1,3-oxazol-5-yl)phenyl)methanone | 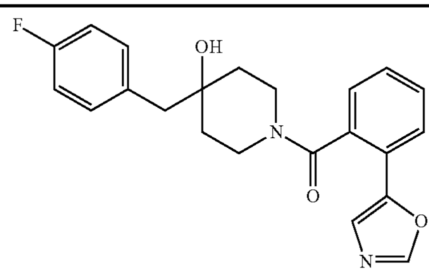 | 381.1 |
| 101 | (4-(3,4-difluorobenzyl)-4-hydroxypiperidin-1-yl) (2-(1,3-oxazol-5-yl)phenyl)methanone | 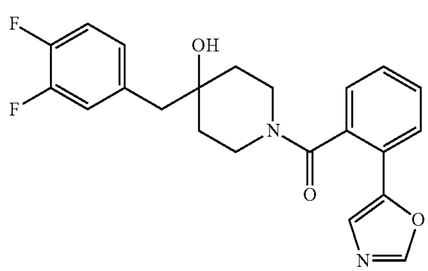 [SMILES: O=C(c1ccccc1-c1cnco1)N1CCC(O)(Cc2ccc(F)c(F)c2)CC1] | 399.1 |

TABLE 14-continued

| Example No. | IUPAC Name | Chemical Structure | MS |
|---|---|---|---|
| 102 | (4-(2,4-difluorobenzyl)-4-hydroxypiperidin-1-yl) (2-(1,3-oxazol-5-yl)phenyl)methanone | 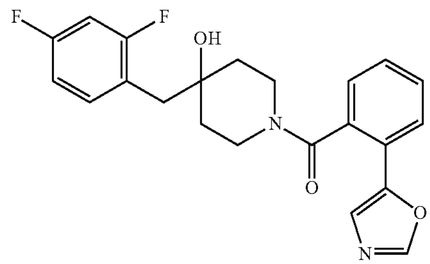 [SMILES: O=C(c1ccccc1-c1cnco1)N1CCC(O)(Cc2ccc(F)cc2F)CC1] | 399.1 |
| 103 | 4-((4-hydroxy-1-(2-(1,3-oxazol-5-yl)benzoyl)piperidin-4-yl)methyl)benzonitrile | 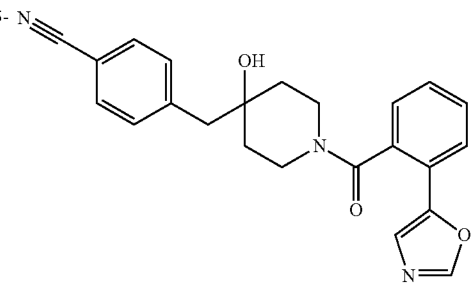 | 388.1 |
| 104 | (4-hydroxy-4-(pyridin-2-ylmethyl)piperidin-1-yl) (2-(1,3-oxazol-5-yl)phenyl)methanone | 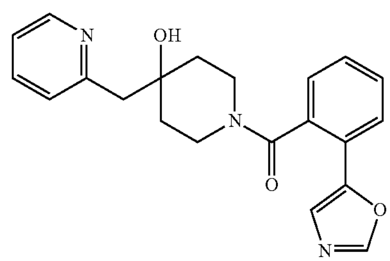 [SMILES: O=C(c1ccccc1-c1cnco1)N1CCC(O)(Cc2ccccn2)CC1] | 364.2 |
| 105 | (4-(2,4-difluorobenzyl)-4-hydroxypiperidin-1-yl) (2-(pyrimidin-4-yl)pyridin-3-yl)methanone | 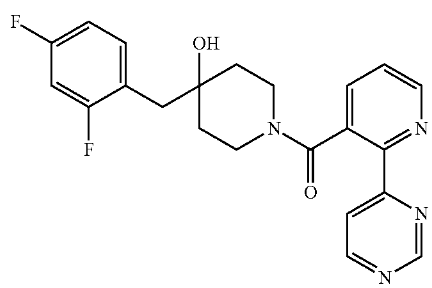 [SMILES: O=C(c1cccnc1-c1ccncn1)N1CCC(O)(Cc2ccc(F)cc2F)CC1] | 411.1 |
| 106 | (4-(3,4-difluorobenzyl)-4-hydroxypiperidin-1-yl) (2-(pyrimidin-4-yl)pyridin-3-yl)methanone | 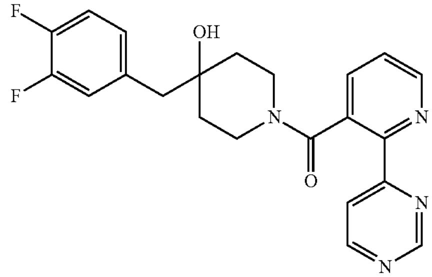 [SMILES: O=C(c1cccnc1-c1ccncn1)N1CCC(O)(Cc2ccc(F)c(F)c2)CC1] | 411.1 |

Formulation Example 1

Production of Capsule

| | |
|---|---|
| 1) compound of Example 1 | 30 mg |
| 2) finely divided powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2

Production of Tablet

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

Experimental Example 1

Construction of Human CH24H (CYP46) Expression Vector

A plasmid DNA for expressing human CH24H in FreeStyle 293 cell was produced as follows. Using Full-Length Mammalian Gene Collection No. 4819975 (Invitrogen) as a template, and the following two kinds of synthesis DNAs:

```
                                      (SEQ ID NO: 1)
5'-GCCCCGGAGCCATGAGCCCCGGGCTG-3'
and (SEQ ID NO: 2)
5'-GTCCTGCCTGGAGGCCCCCTCAGCAG-3',
```

PCR was performed to amplify 91-1625 bp region of human CH24H (BCO22539). The obtained fragment was cloned using TOPO TA Cloning Kit (Invitrogen). The obtained fragment was subcloned to pcDNA3.1(+) digested with BamHI and XhoI to give a plasmid DNA (pcDNA3.1(+)/hCH24H) for human CH24H expression.

Experimental Example 2

Expression of Human CH24H and Preparation of Human CH24H Lysate

The expression of human CH24H was performed using FreeStyle 293 Expression System (Invitrogen). According to the manual attached to FreeStyle 293 Expression System and using the plasmid DNA (pcDNA3.1(+)/hCH24H) for human CH24H expression constructed in Experimental Example 1, a transient expression using FreeStyle 293-F cell was performed. After transfection, the cells were cultured with shaking at 37° C., 8% $CO_2$, 125 rpm for 2 days. The cells were collected by centrifugation, and suspended in a buffer for suspension (100 mM potassium phosphate (pH 7.4), 0.1 mM EDTA, 1 mM DTT, 20% Glycerol). The suspended product was disrupted by a polytron homogenizer (manufactured by Kinematica), and centrifuged at 9000×g for 10 min, and the supernatant was collected. The collected supernatant was cryopreserved (−80° C.) as a human CH24H lysate standard product.

Experimental Example 3

Measurement of CH24H Inhibitory Activity

For the measurement of CH24H inhibitory activity, using the human CH24H lysate prepared in Experimental Example 2, the amount of 24-HC produced from cholesterol by catalysis of CH24H was measured in the presence of a test compound, and the amount was compared with that in the absence of the test compound. That is, a test compound solution at various concentrations were mixed with a reaction buffer (50 mM potassium phosphate containing 0.1% BSA and Complete, EDTA-free protease inhibitor cocktail, pH 7.4) and human CH24H lysate. Then, [$^{14}$C] cholesterol (53 mCi/mmol specific activity, 15 μM) was added, and CH24H reaction was performed at 37° C. for 5 hr. After completion of the reaction, a quenching solution consisting of chloroform/methanol/distillation water (2:2:1 v/v) was added, and the resulting 24-HC was extracted by shaking. The extract was applied to silica gel thin layer chromatography (ethyl acetate:toluene=4:6), and the obtained $^{14}$C-24HC fraction was measured with BAS2500 (Fujifilm Corporation).

The inhibitory rate (%) was calculated from the ratio of radioactivity in the presence of a test compound relative to the radioactivity in the absence of the test compound. The results are shown in the following Tables 15 and 16.

TABLE 15

| Test compound | Inhibitory rate (%) at 1 μM |
|---|---|
| Example 1 | 92 |
| Example 2 | 90 |
| Example 5 | 70 |
| Example 9 | 87 |
| Example 14 | 92 |
| Example 25 | 94 |
| Example 26 | 92 |
| Example 30 | 91 |
| Example 32 | 92 |
| Example 34 | 90 |
| Example 39 | 90 |
| Example 41 | 93 |
| Example 44 | 95 |
| Example 54 | 90 |
| Example 56 | 90 |
| Example 58 | 84 |
| Example 59 | 83 |
| Example 60 | 82 |
| Example 63 | 82 |
| Example 67 | 89 |
| Example 70 | 89 |
| Example 82 | 87 |
| Example 86 | 89 |
| Example 87 | 89 |
| Example 92 | 88 |
| Example 97 | 87 |

TABLE 16

| Test compound | Inhibitory rate (%) at 1 μM |
|---|---|
| Example 102 | 89 |
| Example 105 | 95 |

Experimental Example 4

Quantification Test of 24-HC

Animals used were 6-week-old female C57BL/6N mice (3 mice/group). A test compound was suspended in a 0.5% aqueous methylcellulose [133-14255 WAKO] solution (1 mg/mL). The body weight of the mice was measured, and the solution was forcibly administered orally and repeatedly once a day for 3 days. At 16 hours after the third administration, half of the brain was recovered, and the amount of 24-HC was measured.

The wet weight of the brain was measured, and the brain was homogenized with about 4-fold amount (0.5 mL) of saline. This solution was used as a brain extract. 24-HC in the brain extract was extracted with an acetonitrile solution (98% acetonitrile, 1.98% methanol, 0.02% formic acid), and quantified by HPLC. The average value of 24-HC amount was calculated and the results are shown in relative values with the control group as 100%. The results are shown in the following Table 17.

TABLE 17

| Test compound | decrease rate (%) at 10 mg/kg |
|---|---|
| Example 14 | 67 |
| Example 30 | 87 |
| Example 44 | 55 |
| Example 54 | 64 |
| Example 62 | 71 |
| Example 67 | 43 |
| Example 70 | 60 |
| Example 87 | 37 |
| Example 92 | 60 |
| Example 105 | 40 |

Experimental Example 5

Y-Maze Test Using APP/PS1 Double Transgenic Mouse

Animals used were 3-month-old female APP/PS1 double transgenic mice (10-15 mice/group). A test compound was suspended in a 0.5% aqueous methylcellulose [133-14255 WAKO] solution (1 mg/mL). The body weight of the mice was measured, and the solution was forcibly administered orally and repeatedly once a day for 14 days. At 16 hours after the 13th administration, spontaneous alternation behavior in Y-maze test was evaluated. Using a particular arm of a Y-shaped test apparatus as the starting point, the frequency of moving to a different arm was counted for 5 min. The first two times of entry were excluded from the total number of entry. In addition, the mice that entered less than 10 times in total were excluded. Movement to an arm different from the arm into which the mouse entered last but one was considered an alternation behavior, and the ratio to the total number of moving was calculated as a spontaneous alternation behavior rate. As comparison subjects, a control group (test compound-non treatment group) and a control group in wild-type mice were used. The results are shown in the following Table 18.

TABLE 18

| | Spontaneous alternation behavior rate (%) | | | |
|---|---|---|---|---|
| | wild-type mice | APP/PS1 double transgenic mouse | | |
| Test compound | control group | control group | 10 mg/kg | 30 mg/kg |
| Example 44 | 68 | 56 | 71 | 71 |
| Example 92 | 71 | 57 | 62 | 72 |

INDUSTRIAL APPLICABILITY

The compound of the present invention has a superior CH24H inhibitory action, which is useful as an agent for the prophylaxis or treatment of neurodegenerative disease (e.g., Alzheimer's disease, mild cognitive impairment, Huntington's disease, Parkinson's disease, amyotrophic lateral sclerosis, traumatic brain injury, cerebral infarction, glaucoma, multiple sclerosis and the like), epilepsy, schizophrenia and the like.

This application is based on patent application No. 2011-222741, filed in Japan, the contents of which are encompassed in full herein.

The invention claimed is:

1. A method for the treatment of amyotrophic lateral sclerosis, traumatic brain injury, cerebral infarction, glaucoma, epilepsy, schizophrenia or spasm in a mammal, which comprises administering an effective amount of a compound represented by the formula (I)

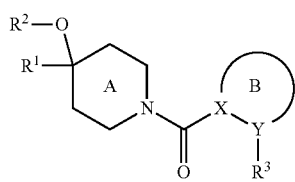

wherein
$R^1$ is an optionally substituted $C_{1-6}$ alkyl group;
$R^2$ is a hydrogen atom of an optionally substituted $C_{1-6}$ alkyl group;
$R^3$ is an optionally substituted 5- or 6-membered aromatic heterocyclic group;
ring A is a further optionally substituted piperidine ring (the piperidine ring is optionally bridged); and
ring B is a further optionally substituted 5- or 6-membered aromatic ring (X and Y are independently a carbon atom or a nitrogen atom),
or a salt thereof,
to the mammal.

2. The method of claim 1, wherein $R^3$ is an optionally substituted 5- or 6-membered nitrogen-containing aromatic heterocyclic group.

3. The method of claim 1, wherein $R^3$ is a 5- or 6-membered nitrogen-containing aromatic heterocyclic group optionally substituted by 1 to 3 halogen atoms.

4. The method of claim 1, wherein $R^3$ is a group represented by

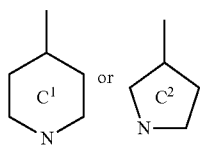

wherein
ring $C^1$ is an optionally substituted 6-membered nitrogen-containing aromatic heterocycle containing at least one nitrogen atom; and
ring $C^2$ is an optionally substituted 5-membered nitrogen-containing aromatic heterocycle containing at least one nitrogen atom,
each of which is optionally substituted by 1 to 3 halogen atoms.

5. The method of claim 1, wherein ring B is benzene, thiazole, isoxazole, pyrazole, pyridine or pyrazine (X and Y are independently a carbon atom or a nitrogen atom), each of which is, in addition to $R^3$ and —C(=O)-ring A, optionally substituted by 1 to 3 substituents selected from the group consisting of:
(1) a halogen atom,
(2) a $C_{1-6}$ alkyl group optionally substituted by 1 to 3 halogen atoms,
(3) a $C_{1-6}$ alkoxy group, and
(4) a $C_{1-6}$ alkylenedioxy group.

6. The method of claim 1, wherein ring B is

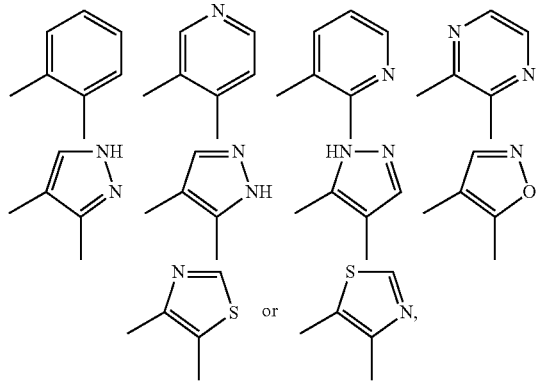

each of which is, in addition to $R^3$ and —C(=O)-ring A, optionally substituted by 1 to 3 substituents selected from the group consisting of:
(1) a halogen atom,
(2) a $C_{1-6}$ alkyl group optionally substituted by 1 to 3 halogen atoms,
(3) a $C_{1-6}$ alkoxy group, and
(4) a $C_{1-6}$ alkylenedioxy group.

7. The method of claim 1, wherein $R^2$ is a hydrogen atom.

8. The method of claim 1, wherein $R^1$ is a $C_{1-6}$ alkyl group optionally substituted by 1 to 3 substituents selected from the group consisting of:
(1) a $C_{6-14}$ aryl group optionally substituted by 1 to 3 substituents selected from the group consisting of:
(a) a halogen atom,
(b) a cyano group, and
(c) a $C_{1-6}$ alkoxy group optionally substituted by 1 to 3 halogen atoms,
(2) a 5- or 6-membered monocyclic aromatic heterocyclic group optionally substituted by 1 to 3 substituents selected from the group consisting of:
(a) a halogen atom,
(b) a cyano group, and
(c) a $C_{1-6}$ alkoxy group optionally substituted by 1 to 3 halogen atoms, and
(3) a 3- to 8-membered monocyclic non-aromatic heterocyclic group optionally substituted by 1 to 3 substituents selected from the group consisting of:
(a) a halogen atom, (b) a cyano group, and
(c) a $C_{1-6}$ alkoxy group optionally substituted by 1 to 3 halogen atoms;

$R^2$ is a hydrogen atom or a $C_{1-6}$ alkyl group;

$R^3$ is a 5- or 6-membered nitrogen-containing aromatic heterocyclic group optionally substituted by 1 to 3 halogen atoms;

ring A is a piperidine ring having no substituent other than $R^1$, $R^2$—O— and —C(=O)-ring B, or an oxa-9-azabicyclo [3.3.1]nonane ring having no substituent other than $R^1$, $R^2$—O— and —C(=O)-ring B; and ring B is a 5- or 6-membered aromatic ring which is, in addition to $R^3$ and —C(=O)-ring A, optionally substituted by 1 to 3 substituents selected from the group consisting of:
 (1) a halogen atom,
 (2) a $C_{1-6}$ alkyl group optionally substituted by 1 to 3 halogen atoms,
 (3) a $C_{1-6}$ alkoxy group, and
 (4) a $C_{1-6}$ alkylenedioxy group.

\* \* \* \* \*

UNITED STATES PATENT AND TRADEMARK OFFICE
CERTIFICATE OF CORRECTION

PATENT NO. : 9,440,990 B2
APPLICATION NO. : 14/847703
DATED : September 13, 2016
INVENTOR(S) : Tatsuki Koike Page 1 of 1

It is certified that error appears in the above-identified patent and that said Letters Patent is hereby corrected as shown below:

In the Claims

In Claim 1, Column 115, Lines 29-30:
"$R^2$ is a hydrogen atom of an optionally substituted $C_{1-6}$ alkyl group;"
Should read:
--$R^2$ is a hydrogen atom or an optionally substituted $C_{1-6}$ alkyl group;--.

In Claim 6, Column 116, Line 35:

"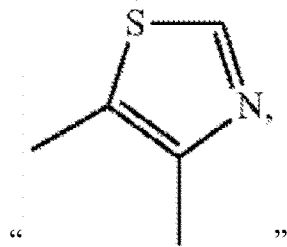,"

Should read:

--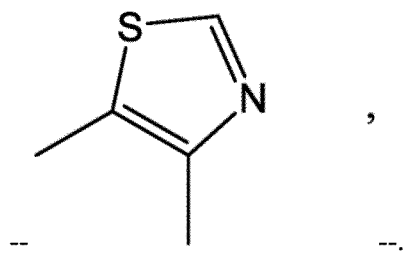,--.

Signed and Sealed this
Eighth Day of June, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 2

<210> SEQ ID NO 1
<211> LENGTH: 26
<212> TYPE: DNA
<213> ORGANISM: Artificial
<220> FEATURE:
<223> OTHER INFORMATION: PCR primer

<400> SEQUENCE: 1
gccccggagc catgagcccc gggctg                    26

<210> SEQ ID NO 2
<211> LENGTH: 26
<212> TYPE: DNA
<213> ORGANISM: Artificial

```
<220> FEATURE:
<223> OTHER INFORMATION: PCR primer

<400> SEQUENCE: 2
gtcctgcctg gaggcccct cagcag                                    26
```